(12) United States Patent
Liew et al.

(10) Patent No.: US 7,840,247 B2
(45) Date of Patent: Nov. 23, 2010

(54) METHODS OF PREDICTING MUSCULOSKELETAL DISEASE

(75) Inventors: Siau-Way Liew, Pinole, CA (US); Philipp Lang, Lexington, MA (US); Daniel Steines, Palo Alto, CA (US)

(73) Assignee: ImaTx, Inc., Burlington, MA (US)

( * ) Notice: Subject to any disclaimer, the term of this patent is extended or adjusted under 35 U.S.C. 154(b) by 799 days.

(21) Appl. No.: 10/753,976

(22) Filed: Jan. 7, 2004

(65) Prior Publication Data

US 2004/0242987 A1  Dec. 2, 2004

Related U.S. Application Data

(63) Continuation-in-part of application No. 10/665,725, filed on Sep. 16, 2003, application No. 10/753,976.

(60) Provisional application No. 60/411,413, filed on Sep. 16, 2002, provisional application No. 60/438,641, filed on Jan. 7, 2003.

(51) Int. Cl.
*G01B 15/02* (2006.01)
(52) U.S. Cl. .................. 600/407; 378/56; 378/54; 128/660.01
(58) Field of Classification Search .............. 378/54, 378/56; 128/660.01
See application file for complete search history.

(56) References Cited

U.S. PATENT DOCUMENTS

| 2,274,808 | A | 3/1942 | Rinn | 250/69 |
|---|---|---|---|---|
| 3,924,133 | A | 12/1975 | Reiss | 250/408 |
| 4,012,638 | A | 3/1977 | Altschuler et al. | 250/491 |
| 4,126,789 | A | 11/1978 | Vogl et al. | 250/505 |
| 4,233,507 | A | 11/1980 | Volz | 250/252 |
| 4,251,732 | A | 2/1981 | Fried | 250/479 |
| 4,298,800 | A | 11/1981 | Goldman | 250/445 T |
| 4,356,400 | A | 10/1982 | Polizzi et al. | 378/138 |
| 4,400,827 | A | 8/1983 | Spears | 378/207 |

(Continued)

FOREIGN PATENT DOCUMENTS

CA     2342344     3/2000

(Continued)

OTHER PUBLICATIONS

Active Contours; The Application of Techniques From Graphics, Vision, Control Theory and Statistics to Visual Tracking of Shapes in Motion, Editors Andrew Blake, Michael Isard, 1999 Springer Verlag, Title page and Table of Contents pages only (ISBN 3540762175).

(Continued)

*Primary Examiner*—Brian Casler
*Assistant Examiner*—John F Ramirez
(74) *Attorney, Agent, or Firm*—Sunstein Kann Murphy & Timbers LLP

(57) ABSTRACT

Methods of predicting bone or joint disease in a subject are presented. The method may include determining one or more micro-structural parameters, one or more macroanatomical parameters or biomechanical parameters of a joint in the subject. At least two of the parameters are combined to predict the risk of bone or articular disease. Additionally, methods of determining the effect of a candidate agent on any subject's risk of developing bone or joint disease are presented.

16 Claims, 35 Drawing Sheets

U.S. PATENT DOCUMENTS

| | | | |
|---|---|---|---|
| 4,593,400 A | 6/1986 | Mouyen | 378/99 |
| 4,649,561 A | 3/1987 | Arnold | 378/207 |
| 4,686,695 A | 8/1987 | Macovski | 378/146 |
| 4,721,112 A | 1/1988 | Hirano et al. | |
| 4,782,502 A | 11/1988 | Schulz | 378/18 |
| 4,922,915 A | 5/1990 | Arnold et al. | 128/653 R |
| 4,956,859 A | 9/1990 | Lanza et al. | 378/157 |
| 4,985,906 A | 1/1991 | Arnold | 378/18 |
| 5,001,738 A | 3/1991 | Brooks | 378/170 |
| 5,090,040 A | 2/1992 | Lanza et al. | 378/62 |
| 5,122,664 A | 6/1992 | Ito et al. | 250/327.2 |
| 5,127,032 A | 6/1992 | Lam et al. | 378/189 |
| 5,150,394 A | 9/1992 | Karellas | 378/62 |
| 5,172,695 A | 12/1992 | Cann et al. | 128/653.1 |
| 5,187,731 A | 2/1993 | Shimura | 378/207 |
| 5,200,993 A | 4/1993 | Wheeler et al. | 379/96 |
| 5,222,021 A | 6/1993 | Feldman et al. | 364/413.14 |
| 5,228,445 A * | 7/1993 | Pak et al. | 600/437 |
| 5,235,628 A | 8/1993 | Kalender | 378/207 |
| 5,247,934 A * | 9/1993 | Wehrli et al. | 600/410 |
| 5,270,651 A | 12/1993 | Wehrli | 324/308 |
| 5,271,401 A | 12/1993 | Fishman | 128/654 |
| 5,320,102 A | 6/1994 | Paul et al. | 128/653.2 |
| 5,335,260 A * | 8/1994 | Arnold | 378/207 |
| 5,384,643 A | 1/1995 | Inga et al. | 358/403 |
| 5,476,865 A | 12/1995 | Panetta et al. | 514/369 |
| 5,493,593 A | 2/1996 | Müller et al. | 378/19 |
| 5,493,601 A | 2/1996 | Fivez et al. | 378/207 |
| 5,513,240 A | 4/1996 | Hausmann et al. | 378/170 |
| 5,521,955 A | 5/1996 | Gohno et al. | 378/18 |
| 5,537,483 A | 7/1996 | Stapleton et al. | 382/309 |
| 5,562,448 A | 10/1996 | Mushabac | 433/215 |
| 5,565,678 A | 10/1996 | Manian | 250/252.1 |
| 5,592,943 A | 1/1997 | Buhler et al. | 128/661.03 |
| 5,600,574 A | 2/1997 | Reitan | 364/552 |
| 5,657,369 A | 8/1997 | Stein et al. | 378/208 |
| 5,673,298 A | 9/1997 | Mazess | 378/54 |
| 5,687,210 A | 11/1997 | Maitrejean et al. | 378/57 |
| 5,769,072 A | 6/1998 | Olsson et al. | 128/205.13 |
| 5,769,074 A | 6/1998 | Barnhill et al. | 128/630 |
| 5,772,592 A | 6/1998 | Cheng et al. | 600/407 |
| 5,852,647 A | 12/1998 | Schick et al. | 378/53 |
| 5,864,146 A | 1/1999 | Karellas | 250/581 |
| 5,886,353 A | 3/1999 | Spivey et al. | 250/370.09 |
| 5,915,036 A * | 6/1999 | Grunkin et al. | 382/132 |
| 5,917,877 A | 6/1999 | Chiabrera et al. | 378/5.3 |
| 5,931,780 A | 8/1999 | Giger et al. | 600/407 |
| 5,945,412 A | 8/1999 | Fuh et al. | 514/176 |
| 5,948,692 A | 9/1999 | Miyauti et al. | 436/501 |
| 6,029,078 A | 2/2000 | Weinstein et al. | 600/407 |
| 6,064,716 A | 5/2000 | Siffert et al. | 378/53 |
| 6,077,224 A | 6/2000 | Lang et al. | |
| 6,108,635 A | 8/2000 | Herren et al. | 705/2 |
| 6,156,799 A | 12/2000 | Hartke et al. | 514/573 |
| 6,178,225 B1 | 1/2001 | Zur et al. | 378/98.2 |
| 6,205,348 B1 | 3/2001 | Giger et al. | 600/407 |
| 6,215,846 B1 | 4/2001 | Mazess et al. | 378/62 |
| 6,226,393 B1 | 5/2001 | Grunkin et al. | 382/128 |
| 6,246,745 B1 * | 6/2001 | Bi et al. | 378/54 |
| 6,248,063 B1 | 6/2001 | Barnhill et al. | 600/300 |
| 6,249,692 B1 | 6/2001 | Cowin | 600/407 |
| 6,252,928 B1 | 6/2001 | MacKenzie | 378/54 |
| 6,285,901 B1 | 9/2001 | Taicher et al. | 600/410 |
| 6,289,115 B1 | 9/2001 | Takeo | 382/130 |
| 6,302,582 B1 | 10/2001 | Nord et al. | 378/207 |
| 6,306,822 B1 * | 10/2001 | Kumagai et al. | 514/7 |
| 6,315,553 B1 | 11/2001 | Sachdeva et al. | 433/24 |
| 6,320,931 B1 | 11/2001 | Arnold | 378/56 |
| 6,377,653 B1 | 4/2002 | Lee et al. | 378/54 |
| 6,411,729 B1 | 6/2002 | Grunkin | 382/132 |
| 6,430,427 B1 | 8/2002 | Lee et al. | 600/407 |
| 6,442,287 B1 * | 8/2002 | Jiang et al. | 382/128 |
| 6,449,502 B1 | 9/2002 | Ohkubo | 600/407 |
| 6,463,344 B1 | 10/2002 | Pavloskaia et al. | 700/98 |
| 6,501,827 B1 | 12/2002 | Takasawa | 378/116 |
| 6,556,698 B1 | 4/2003 | Diano et al. | 382/132 |
| 6,690,761 B2 | 2/2004 | Lang et al. | 378/56 |
| 6,694,047 B1 | 2/2004 | Farrokhnia et al. | 382/132 |
| 6,717,174 B2 | 4/2004 | Karellas | 250/582 |
| 6,799,066 B2 | 9/2004 | Steines et al. | 600/407 |
| 6,807,249 B2 | 10/2004 | Dinten et al. | 378/54 |
| 6,811,310 B2 | 11/2004 | Lang et al. | 378/169 |
| 6,824,309 B2 | 11/2004 | Robert-Coutant et al. | 378/207 |
| 6,829,378 B2 | 12/2004 | DiFilippo et al. | 382/128 |
| 6,835,377 B2 | 12/2004 | Goldberg et al. | 424/93.7 |
| 6,836,557 B2 | 12/2004 | Tamez-Pena et al. | 382/128 |
| 6,895,077 B2 | 5/2005 | Karellas et al. | 378/98.3 |
| 6,904,123 B2 | 6/2005 | Lang | 378/54 |
| 6,934,590 B2 | 8/2005 | Ogawa | 700/19 |
| 6,975,894 B2 | 12/2005 | Wehrli et al. | 600/407 |
| 7,050,534 B2 | 5/2006 | Lang | 378/54 |
| 7,058,159 B2 | 6/2006 | Lang et al. | 378/54 |
| 7,120,225 B2 | 10/2006 | Lang et al. | 378/54 |
| 7,184,814 B2 | 2/2007 | Lang et al. | 600/416 |
| 7,239,908 B1 | 7/2007 | Alexander et al. | 600/427 |
| 7,245,697 B2 | 7/2007 | Lang | 378/54 |
| 7,292,674 B2 | 11/2007 | Lang | 378/54 |
| 7,379,529 B2 | 5/2008 | Lang | 378/54 |
| 7,467,892 B2 | 12/2008 | Lang et al. | 378/207 |
| 7,545,964 B2 | 6/2009 | Lang et al. | 382/128 |
| 7,580,504 B2 | 8/2009 | Lang et al. | 378/56 |
| 7,660,453 B2 | 2/2010 | Lang | 382/132 |
| 7,664,298 B2 | 2/2010 | Lang et al. | 382/128 |
| 7,676,023 B2 | 3/2010 | Lang | 378/54 |
| 2002/0087274 A1 | 7/2002 | Alexander et al. | 702/19 |
| 2002/0159567 A1 | 10/2002 | Sako et al. | 378/117 |
| 2002/0186818 A1 | 12/2002 | Arnaud et al. | 378/165 |
| 2002/0194019 A1 | 12/2002 | Evertsz | 705/2 |
| 2002/0196966 A1 | 12/2002 | Jiang et al. | 382/132 |
| 2003/0015208 A1 | 1/2003 | Lang et al. | 128/922 |
| 2003/0198316 A1 | 10/2003 | Dewaele et al. | 378/54 |
| 2004/0106868 A1 | 6/2004 | Liew et al. | 600/442 |
| 2004/0242987 A1 | 12/2004 | Liew et al. | 600/407 |
| 2004/0247074 A1 | 12/2004 | Langton | 378/54 |
| 2005/0015002 A1 | 1/2005 | Dixon et al. | 600/407 |
| 2005/0148860 A1 | 7/2005 | Liew et al. | 600/410 |
| 2005/0240096 A1 | 10/2005 | Ackerman et al. | 600/410 |
| 2006/0062442 A1 | 3/2006 | Arnaud et al. | 382/128 |
| 2007/0047794 A1 | 3/2007 | Lang et al. | 382/132 |
| 2007/0274442 A1 | 11/2007 | Gregory et al. | 378/54 |
| 2008/0031412 A1 | 2/2008 | Lang et al. | 378/54 |
| 2008/0058613 A1 | 3/2008 | Lang et al. | 600/300 |
| 2008/0097794 A1 | 4/2008 | Arnaud et al. | 705/3 |
| 2008/0219412 A1 | 9/2008 | Lang | 378/207 |
| 2009/0207970 A1 | 8/2009 | Lang | 378/38 |
| 2009/0225958 A1 | 9/2009 | Lang | 378/207 |
| 2010/0014636 A1 | 1/2010 | Lang et al. | 378/56 |

FOREIGN PATENT DOCUMENTS

| | | |
|---|---|---|
| DE | 19853965 | 5/2000 |
| EP | 0314506 | 5/1989 |
| EP | 0797952 | 10/1997 |
| EP | 0570936 | 8/2000 |
| EP | 0678191 | 2/2001 |
| EP | 1230896 | 8/2002 |
| EP | 1283492 | 2/2003 |
| EP | 1349098 | 10/2003 |
| EP | 1357480 | 10/2003 |
| EP | 1424650 | 6/2004 |
| EP | 1598778 | 11/2005 |
| EP | 1069395 | 7/2006 |
| GB | 2023920 | 1/1980 |
| JP | 62 266053 | 11/1987 |

| | | |
|---|---|---|
| JP | 05 099829 | 4/1993 |
| JP | 08 186762 | 7/1996 |
| JP | 10 145396 | 5/1998 |
| JP | 10 262959 | 5/1998 |
| JP | 10 262959 | 10/1998 |
| JP | 11 069136 | 3/1999 |
| JP | 11 112877 | 4/1999 |
| JP | 2002 045722 | 2/2000 |
| JP | 2000 126168 | 5/2000 |
| JP | 2000 139889 | 5/2000 |
| JP | 2003 230557 | 8/2003 |
| WO | WO 94/12855 | 6/1994 |
| WO | WO 95/14431 | 6/1995 |
| WO | WO 99/08597 A1 | 2/1999 |
| WO | WO 99/45371 | 9/1999 |
| WO | WO 99/45845 A1 | 9/1999 |
| WO | WO 99/52331 | 10/1999 |
| WO | WO 00/33157 | 6/2000 |
| WO | WO 00/72216 | 11/2000 |
| WO | WO 01/38824 | 5/2001 |
| WO | WO 01/63488 | 8/2001 |
| WO | WO 01/65449 | 9/2001 |
| WO | WO 02/17789 | 3/2002 |
| WO | WO 02/22014 | 3/2002 |
| WO | WO 02/22014 A1 | 3/2002 |
| WO | WO 02/30283 A2 | 4/2002 |
| WO | WO 02/30283 A3 | 4/2002 |
| WO | WO 02/096284 | 12/2002 |
| WO | WO 03/071934 | 9/2003 |
| WO | WO 03/073232 | 9/2003 |
| WO | WO 03/088085 | 10/2003 |
| WO | WO 2004/019256 | 3/2004 |
| WO | WO 2004/025541 | 3/2004 |
| WO | WO 2004/062495 | 7/2004 |
| WO | WO 2004/086972 | 10/2004 |
| WO | WO 2004/096048 | 11/2004 |
| WO | WO 2005/027732 | 3/2005 |
| WO | WO 2006/033712 | 3/2006 |
| WO | WO 2006/034018 | 3/2006 |
| WO | WO 2008/034101 | 3/2008 |

OTHER PUBLICATIONS

Body CT: A Practical Approach, Editor Slone, 1999 McGraw-Hill publishers, Title page and Table of Contents page only (ISBN 007058219).
Cann CE, "Quantitative CT for Determination of Bone Mineral Density: A Review," Radiology 166:509-522, 1998.
Cheal., et al., "Role of Loads & Prosthesis Material Properties on the Mechanics of the Proximal Femur After Total Hip Arthroplasty," J. Orthop. Res., 10: 405-422, 1992.
Cummings SR, et al., "Bone Density at Various Sites for Prediction of Hip Fractures," Lancet 341:72-75, 1993.
Digital Image Processing, Editor Kenneth R. Castleman, 1996 Prentice Hall, publisher, Title page and Table of Contents pages only (ISBN 0132114674).
Eastell, R. "Treatment of Postmenopausal Osteoporosis," New Engl J Med 338 (11): 736-46, 1998.
Essential Physics of Medical Imaging, Editors Bushberg, Seibert, Leidholdt Jr. & Boone, 2002 Lippincott, Williams & Wilkins, Title page and Table of Contents pages only (ISBN 0683011405).
Faulkner KG. "Bone Densitometry: Choosing the Right Skeletal Site to Measure," J Clin Densitometry. 1:279-85, 1998.
Glüer C-C, et al., "Peripheral Measurement Techniques for the Assessment of Osteoporosis," Semin Nucl Med 27:229-247,1997.
Glüer C-C, "Quantitative Ultrasound Techniques for the Assessment of Osteoporosis—Expert Agreement on Current Status," J Bone Miner Res. 12:1280-1288, 1997.
Hosking D, et al., "Prevention of Bone Loss in Postmenopausal Women Under 60 Years of Age. Early Postmenopausal Intervention Cohort Study Group," N Engl J Med. 338:485-492, 1998.

Marshall D., et al., "Meta-Analysis of How Well Measures of Bone Mineral Density Predict Occurrence of Osteoporotic Fractures," Br Med J. 312:1254-1259, 1996.
Njeh CF, et al., "The Role of Ultrasound in the Assessment of Osteoporosis: A Review," Osteoporosis Int 7:7-22, 1997.
Njeh CF, et al., "Quantitative Ultrasound: Assessment of Osteoporosis and Bone Status," London, England: Martin Dunitz, 1999 Title page and Table of Contents pages only (ISBN 1853176796).
Patel R, et al., "Radiation Dose to the Patient and Operator From a Peripheral Dual X-Ray Absorptiometry System," J Clin Densitom 2:397-401, 1999.
Russ, John C. "The Image Processing Handbook," $3^{rd}$ Edition, pp. 494-501, 1998.
Ruttimann UE, et al., "Fractal Dimension From Radiographs of Periodontal Alveolar Bone. A Possible Diagnostic Indicator of Osteoporosis," Oral Surg Oral Med Oral Pathol 74:98-110, 1992.
Shrout, et al., "Comparison of Morphological Measurements Extracted From Digitized Dental Radiographs With Lumbar and Femoral Bone Mineral Density Measurements in Post," J. Periondontal 71:335-340, 2000.
Southard K A and Southard T E., "Quantitative Features of Digitized Radiographic Bone Profiles." Oral Surgery, Oral Medicine, and Oral Pathology. 73(6): 751-9, Jun. 1992.
Svendsen OL., et al., "Impact of Soft Tissue on In-Vivo Accuracy of Bone Mineral Measurements in the Spine, Hip, and Forearm: A Human Cadaver Study," J Bone Miner Res 10:868-873, 1995.
Tothill P., et al., "Errors Due to Non-Uniform Distribution of Fat in Dual X-Ray Absorptiometry of the Lumbar Spine," Br J Radiol. 65:807-813, 1992.
Verhoeven, et al., "Densitometric Measurements of the Mandible: Accuracy and Validity of Intraoral Versus Extraoral Radiographic Techniques in an In Vitro Study," Clin Oral Impl Res 9: 333-342, 1998.
White SC and Rudolph DJ, "Alterations of the Trabecular Pattern in the Jaws of Patients With Osteoporosis," Oral Surg. Oral Med. Oral Pathol. Oral Radiol. and Endod. 88:628-635, 1999.
X-Ray Structure Determination: A Practical Guide, 2nd Ed. Editors Stout and Jensen, 1989, John Wiley & Sons, Title page and Table of Contents pages only (ISBN 0471607118).
X-Ray Diagnosis: A Physician's Approach, Editor Lam, 1998, Springer-Verlag publishers, Title page and Table of Contents pages only (ISBN 9813083247).
B. Cortet, et al. "Bone Microarchitecture and Mechanical Resistance" Joint Bone Spine, vol. 68, pp. 297-305 (2001).
Barker, "Case Method: Entity Relationship Modeling" (Computer Aided Systems Engineering), $1^{st}$ Ed., Addison-Wesley Longman Pub. Co., Inc., 2 pages (Abstract Pages Only) (1990).
Bauer et al., "Biochemical Markers of Bone Turnover and Prediction of Hip Bone Loss in Older Women: The Study of Osteoporotic Fractures," Journal of Bone and Mineral Research, vol. 14, pp. 1404-1410 (1999).
Beck et al., "Experimental Testing of a DEXA-Derived Curved Beam Model of the Proximal Femur," Journal of Orthopaedic Research, vol. 16, No. 3, pp. 394-398 (1998).
Black et al., "An Assessment Tool for Predicting Fracture Risk in Postmenopausal Women" Osteoporosis International, vol. 12, pp. 519-528 (2001).
Cootes et al., "Anatomical statistical models and their role in feature extraction," The British Journal of Radiology, Special Issue, 7 pages [S133-S139] (2004).
Cootes et al., "Statistical models of appearance for medical image analysis and computer vision," Proc. SPIE Medical Imaging, 14 pages, (2001).
Cootes, "An Introduction to Active Shape Models," Image Processing and Analysis, Ch. 7, pp. 1-26 (2000).
Crabtree et al., "Improving Risk Assessment: Hip Geometry, Bone Mineral Distribution and Bone Strength in Hip Fracture Cases and Controls. The EPOS Study," Osteoporosis Int., vol. 13, pp. 48-54 (2002).
Crawley, "In Vivo Tissue Characterization Using Quantitative Computed Tomography: A Review," Journal of Medical Engineering & Technology, vol. 14, No. 6, pp. 233-242 (1990).

Davies et al., "A Minimum Description Length Approach to Statistical Shape Modeling," IEEE Transaction on Medical Imaging, vol. 21, No. 5, pp. 525-537 (2002).

Duryea et al., "New radiographic-based surrogate outcome measures for osteoarthritis of the knee," Osteoarthritis and Cartilage, vol. 11, pp. 102-110 (2003).

Duryea et al., "Trainable rule-based algorithm for the measurement of joint space width in digital radiographic images of the knee," Medical Physics, vol. 27, No. 3, pp. 580-591 (2000).

Engelman et al., "Impact of Geographic Barriers on the Utilization of Mammograms by Older Rural Women, " Journal of the American Geriatrics Society, vol. 50, No. 1, pp. 62-68 (2002).

Fleute et al., "Incorporating a statistically based shape model into a system for computer-assisted anterior cruciate ligament surgery," Medical Image Analysis, vol. 3, No. 3, pp. 209-222 (1999).

Fleute et al., "Statistical model registration for a C-arm CT system," Computer Science Department, The Johns Hopkins University, pp. 1667-1670 (2002).

Fleute et al., "Nonrigid 3-D/2-D Registration of Images Using Statistical Models," pp. 138-147 (1999).

Gilliland et al., "Patterns of Mammography Use Among Hispanic, American Indian, and Non-Hispanic White Women in New Mexico, 1994-1997," American Journal of Epidemiology, vol. 152, No. 5, pp. 432-437 (2000).

Grisso et al., "Risk Factors for Falls as a Cause of Hip Fracture in Women. The Northeast Hip Fracture Study Group," N. Engl. J. Med., (Abstract Page Only), 1 page, vol. 324, No. 19 (1991).

Gudmundsdottir et al., "Vertebral Bone Density in Icelandic Women Using Quantitative Computed Tomography Without an External Reference Phantom," Osteoporosis Int., vol. 3, pp. 84-89 (1993).

Hayes et al., "Biomechanics of Cortical and Trabecular Bone: Implications for Assessment of Fracture Risk," Basic Orthopaedic Biomechanics, 2nd Ed., Ch. 3, pp. 69-111 (1997).

Hayes et al., "Biomechanics of Fracture Risk Prediction of the Hip and Spine by Quantitative Computed Tomography," Radiologic Clinics of North America, vol. 29, No. 1, pp. 1-18 (1991).

Hayes et al., "Impact Near the Hip Dominates Fracture Risk in Elderly Nursing Home Residents Who Fall," Calcif. Tissue Int. (Abstract Page Only), 1 page, vol. 52, No. 3 (1993).

Hedström et al., "Biochemical Bone Markers and Bone Density in Hip Fracture Patients," Acta Orthop. Scand., vol. 71, No. 4, pp. 409-413 (2000).

Horn, "Closed-form solution of absolute orientation using unit quaternions," J. Opt. Soc. of Am., vol. 4, No. 4, pp. 629-642 (1987).

Ikuta et al., "Quantitative Analysis Using the Star Volume Method Applied to Skeleton Patterns Extracted with a Morphological Filter," Journal of Bone and Mineral Metabolism, vol. 18, pp. 271-277 (2000).

Jacobs et al., "Long-term Bone Mass Evaluation of Mandible and Lumbar Spine in a Group of Women Receiving Hormone Replacement Therapy," European Journal Oral Sciences, vol. 104, pp. 10-16 (1996).

Jazieh et al., "Mammography Utilization Pattern Throughout the State of Arkansas: A Challenge for the Future," Journal of Community Health, vol. 26, No. 4, pp. 249-255 (2001).

Jeffcoat et al., "Post-menopausal bone loss and its relationship to oral bone loss", Periodontology, vol. 23, pp. 94-102 (2000).

Klose, "Teleradiology—A Model for Remote Consultation," Electromedica, vol. 66, No. 1, pp. 37-41 (1998).

Kumasaka et al., "Initial Investigation of Mathematical Morphology for the Digital Extraction of the Skeletal Characteristics of Trabecular Bone," Departments of Oral Surgery and Oral and Maxillofacial Radiology, Kanagawa Dental College, Japan, pp. 161-168 (1996).

Lang et al., "Osteoporosis—Current Techniques and Recent Developments in Quantitative Bone Densitometry" Radiologic Clinics of North America, vol. 29, No. 1, pp. 49-76 (1991).

Metrabio Website, "QUS-2 Calcaneal Ultrasonometer," What's New: Ultrasound, Retrieved from the internet—http://www.metrabio.com/html/_prods/L3-ultrasound-r.ht, 2 pages (2001).

Mourtada et al., "Curved Beam Model of the Proximal Femur for Estimating Stress Using Dual-Energy X-Ray Absorptiometry Derived Structural Geometry," J. Ortho. Res., vol. 14, No. 3, pp. 483-492 (1996).

Ouyang et al., "Morphometric Texture Analysis of Spinal Trabecular Bone Structure Assessed Using Orthogonal Radiographic Projections," Med. Phys., vol. 25, No. 10, pp. 2037-2045 (1998).

Pharoah, "X-Ray Film, Intensifying Screens, and Grids," Ch. 4, Section 4: Imaging Principles and Techniques, Oral Radiology, 4th ed., pp. 68-76 (2000).

Pinilla et al., "Impact Direction from a Fall Influences the Failure Load of the Proximal Femur as Much as Age-Related Bone Loss," Calcified Tissue International, vol. 58, pp. 231-235 (1996).

Riggs et al., "Changes in Bone Mineral Density of the Proximal Femur and Spine with Aging: Differences Between the Postmenopausal and Senile Osteoporosis Syndromes," J. Clin. Invest., vol. 70, pp. 716-723 (1982).

Sandler et al., "An Analysis of the Effect of Lower Extremity Strength on Impact Severity During a Backward Fall," Journal of Biomechanical Engineering, vol. 123, pp. 590-598 (2001).

Southard et al., "The Relationship Between the Density of the Alveolar Processes and that of Post-cranial Bone," J. Dent. Res., vol. 79, No. 4, pp. 964-969 (2000).

Van den Kroonenberg et al., "Dynamic Models for Sideways Falls from Standing Height," Journal of Biomechanical Engineering, vol. 117, pp. 309-318 (1995).

Yoshikawa et al., "Geometric Structure of the Femoral Neck Measured Using Dual-Energy X-Ray Absorptiometry," J. Bone Miner. Res., vol. 10, No. 3, p. 510 (Abstract Only) (1995).

European Patent Office, EPO Communication—Appl. No. 04 700 619.2, dated Dec. 13, 2007 (3 pages).

European Patent Office, EPO Communication—Appl. No. 04 700 619.2, dated Jul. 17, 2008 (4 pages).

International Searching Authority, International Preliminary Examination Report—Appl. No. PCT/US2003/030004, dated Jul. 27, 2004 (2 pages).

International Searching Authority, International Search Report—Appl. No. PCT/US2003/030004, dated Feb. 25, 2004 (5 pages).

United States Patent and Trademark Office, Office Action (Restriction Requirement)—U.S. Appl. No. 10/665,725, dated Aug. 16, 2006 (6 pages).

United States Patent and Trademark Office, Office Action (Restriction Requirement)—U.S. Appl. No. 10/665,725, dated Dec. 29, 2006 (5 pages).

United States Patent and Trademark Office, Office Action (Restriction Requirement)—U.S. Appl. No. 10/665,725, dated Jun. 1, 2007 (10 pages).

United States Patent and Trademark Office, Office Action—U.S. Appl. No. 10/665,725, dated Mar. 13, 2008 (11 pages).

United States Patent and Trademark Office, Office Action—U.S. Appl. No. 10/665,725, dated Nov. 28, 2008 (8 pages).

United States Patent and Trademark Office, Final Office Action—U.S. Appl. No. 10/665,725, dated Aug. 28, 2009 (10 pages).

United States Patent and Trademark Office, Office Action—U.S. Appl. No. 10/665,725, dated Apr. 29, 2010 (26 pages).

* cited by examiner

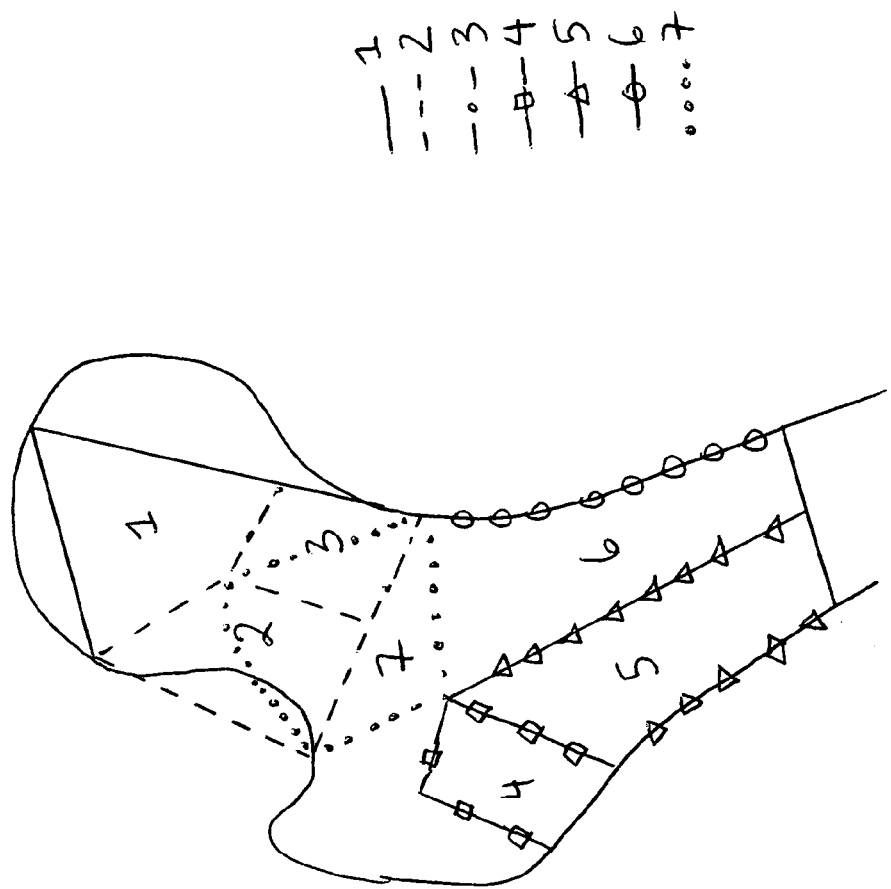
Figure 10: Regions of Interest (ROI) Analyzed

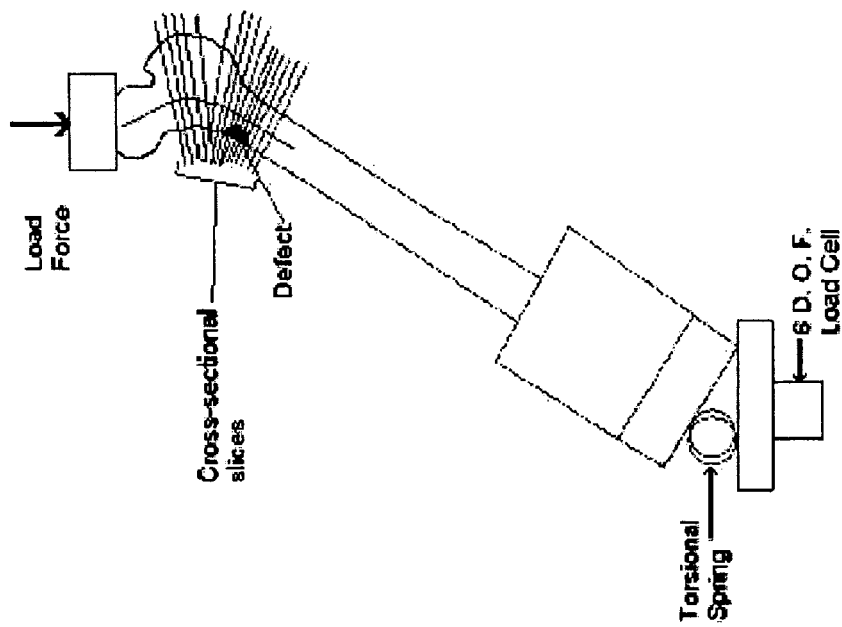
Figure 11: Biomechanical Testing of Intact Femur with Instron Instrument

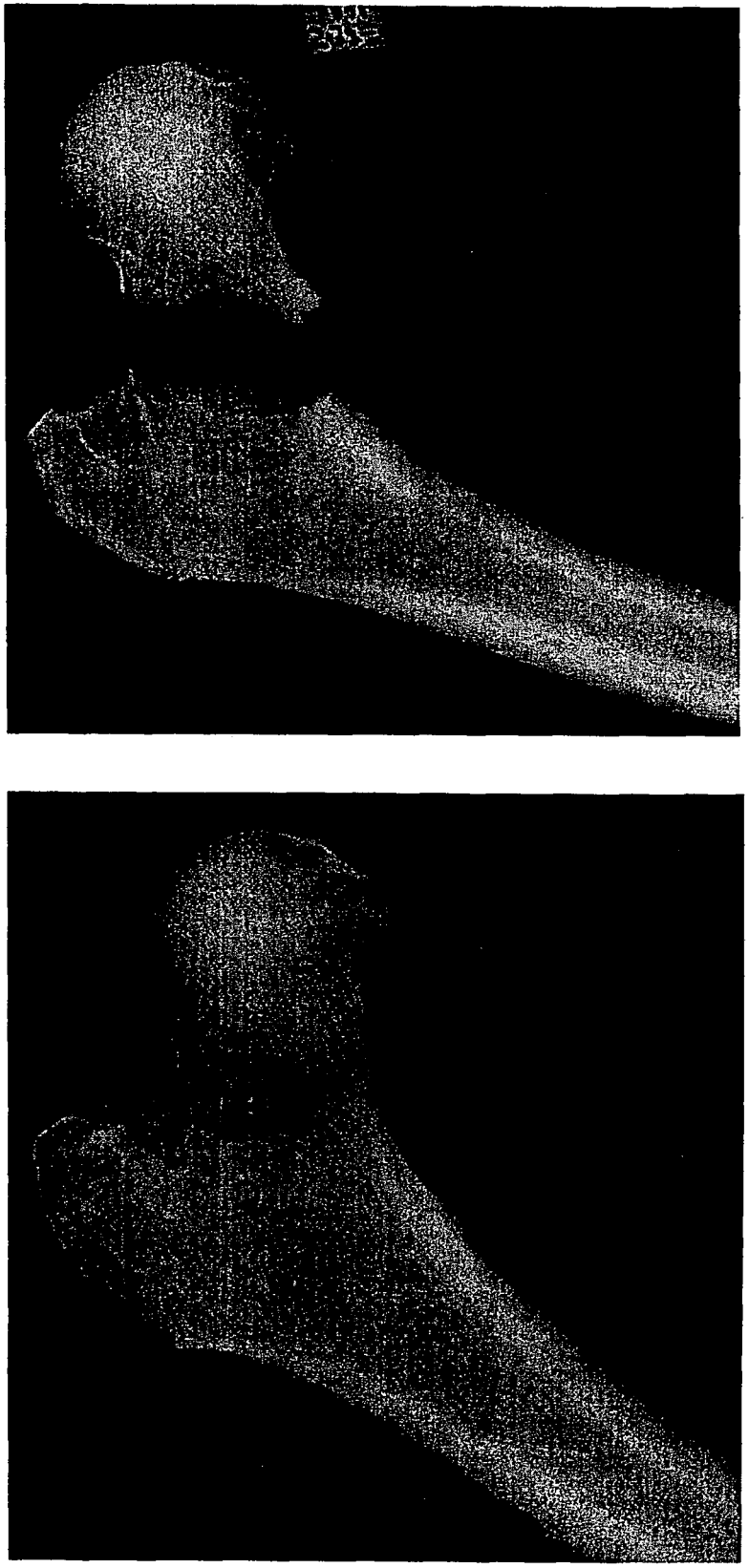
Figure 12: Example of Induced Fracture in Fresh Cadaveric Femur

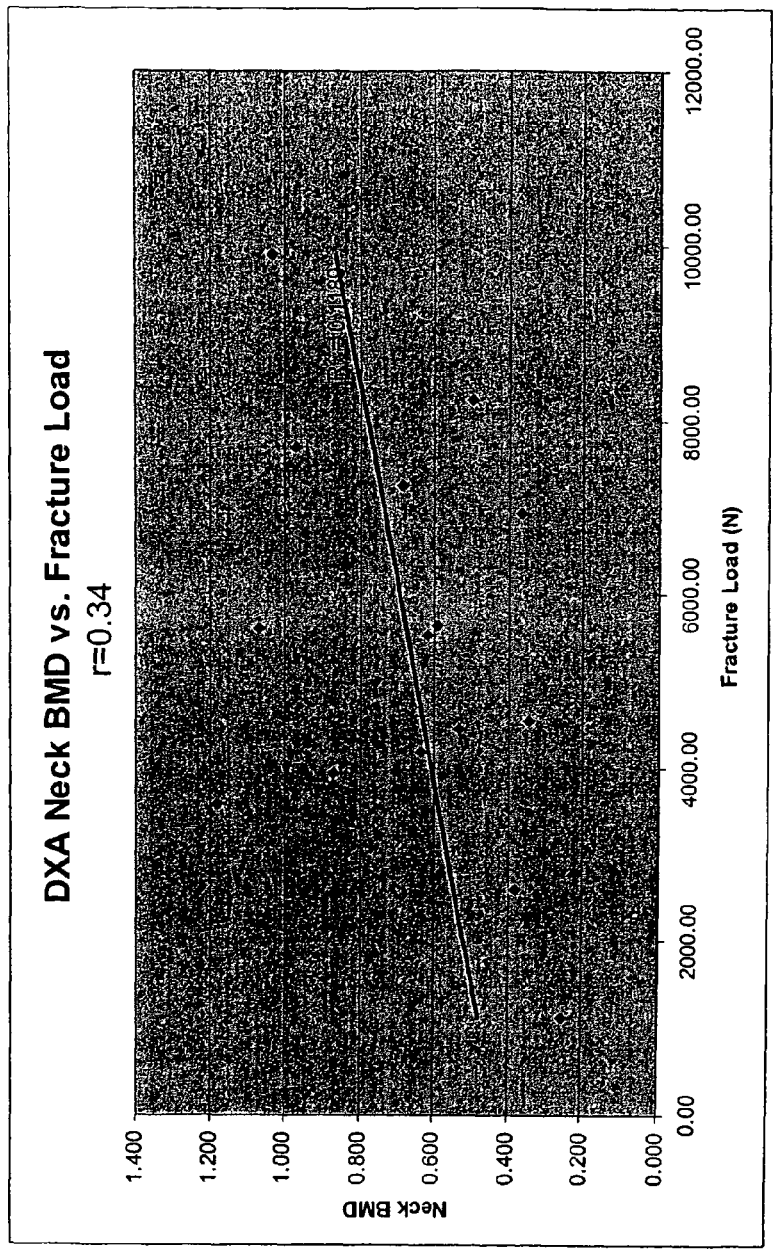
Figure 13: DXA Femoral Neck BMD vs. Biomechanical Fracture Load
n=15, fresh cadaveric specimens

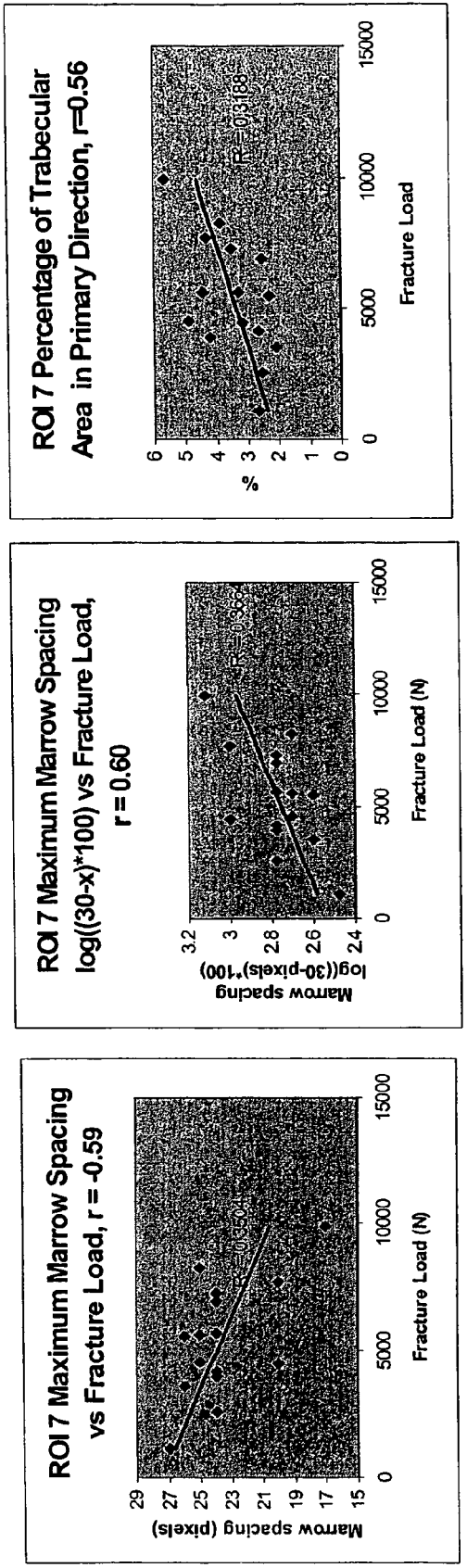
Figure 14: Bone Structure vs. Instron Biomechanical Fracture Load
n=15, fresh cadaveric specimens

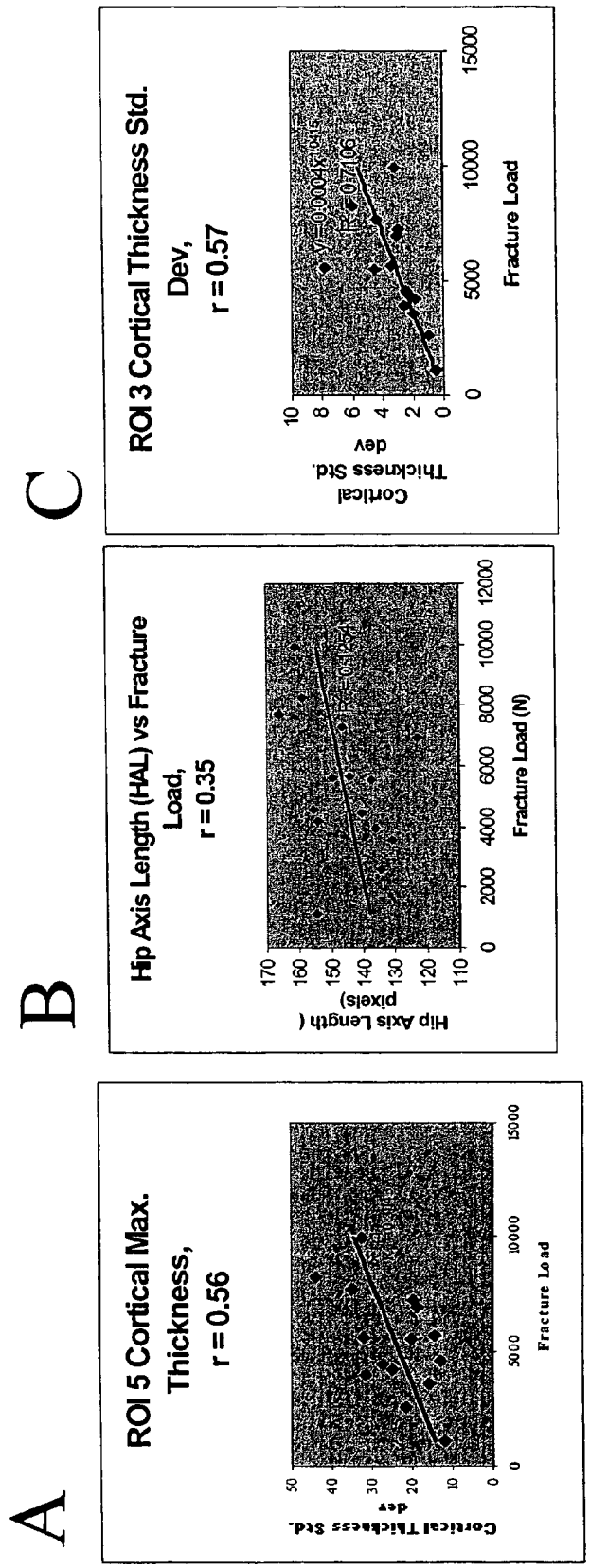
Figure 15: Macro-Anatomical Features vs. Instron Biomechanical Fracture Load
n=15, fresh cadaveric specimens

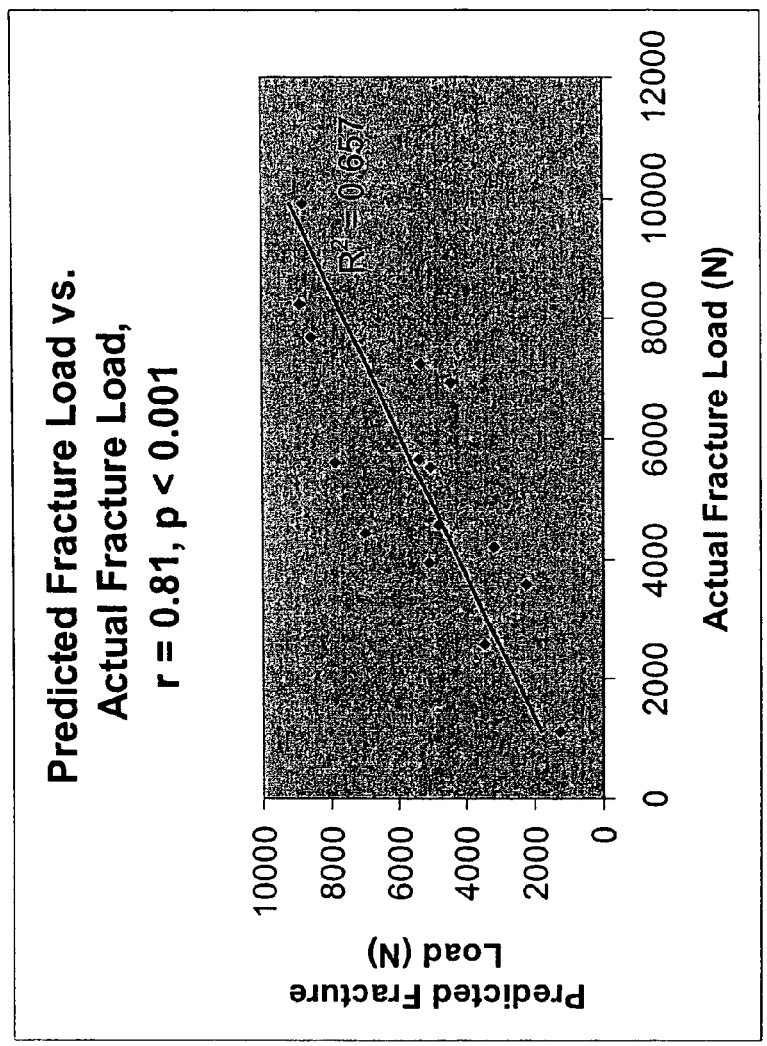
Figure 16: Multivariate Analysis: Combination of Bone Structural and Macro-Anatomical Features
n=15, fresh cadaveric specimens

METHODS OF PREDICTING MUSCULOSKELETAL DISEASE

CROSS REFERENCE TO RELATED APPLICATIONS

This application is a continuation-in-part of U.S. Ser. No. 10/665,725, filed Sep. 16, 2003, which in turn claims the benefit of U.S. Provisional Patent application Ser. No. 60/411,413, filed on Sep. 16, 2002 and also claims the benefit of U.S. Provisional Patent application Ser. No. 60/438,641, filed on Jan. 7, 2003, from which applications priority is hereby claimed under 35 USC §119/120, and which applications are hereby incorporated herein by reference in their entireties herein.

TECHNICAL FIELD

This invention relates to using imaging methods for diagnosis, prognostication, monitoring and management of disease, particularly where that disease affects the musculoskeletal system. This invention identifies novel imaging markers for use in diagnosis, prognostication, monitoring and management of disease, including musculoskeletal disease.

BACKGROUND

Osteoporosis and osteoarthritis are among the most common conditions to affect the musculoskeletal system, as well as frequent causes of locomotor pain and disability. Osteoporosis can occur in both human and animal subjects (e.g. horses). Osteoporosis (OP) and osteoarthritis (OA) occur in a substantial portion of the human population over the age of fifty. The National Osteoporosis Foundation estimates that as many as 44 million Americans are affected by osteoporosis and low bone mass. In 1997 the estimated cost for osteoporosis related fractures was $13 billion. That figure increased to $17 billion in 2002 and is projected to increase to $210-240 billion by 2040. Currently it is expected that one in two women over the age of 50 will suffer an osteoporosis-related fracture.

Imaging techniques are important diagnostic tools, particularly for bone related conditions such as OP and OA. Currently available techniques for the noninvasive assessment of the skeleton for the diagnosis of osteoporosis or the evaluation of an increased risk of fracture include dual x-ray absorptiometry (DXA) (Eastell et al. (1998) *New Engl J. Med* 338:736-746); quantitative computed tomography (QCT) (Cann (1988) *Radiology* 166:509-522); peripheral DXA (PDXA) (Patel et al. (1999) *J Clin Densitom* 2:397-401); peripheral QCT (PQCT) (Gluer et. al. (1997) *Semin Nucl Med* 27:229-247); x-ray image absorptiometry (RA) (Gluer et. al. (1997) *Semin Nucl Med* 27:229-247); and quantitative ultrasound (QUS) (Njeh et al. "Quantitative Ultrasound: Assessment of Osteoporosis and Bone Status" 1999, Martin-Dunitz, London England; U.S. Pat. No. 6,077,224, incorporated herein by reference in its entirety). (See, also, WO 9945845; WO 99/08597; and U.S. Pat. No. 6,246,745).

DXA of the spine and hip has established itself as the most widely used method of measuring BMD. Tothill, P. and D. W. Pye, (1992) *Br J Radiol* 65:807-813. The fundamental principle behind DXA is the measurement of the transmission through the body of x-rays of 2 different photon energy levels. Because of the dependence of the attenuation coefficient on the atomic number and photon energy, measurement of the transmission factors at 2 energy levels enables the area densities (i.e., the mass per unit projected area) of 2 different types of tissue to be inferred. In DXA scans, these are taken to be bone mineral (hydroxyapatite) and soft tissue, respectively. However, it is widely recognized that the accuracy of DXA scans is limited by the variable composition of soft tissue. Because of its higher hydrogen content, the attenuation coefficient of fat is different from that of lean tissue. Differences in the soft tissue composition in the path of the x-ray beam through bone compared with the adjacent soft tissue reference area cause errors in the BMD measurements, according to the results of several studies. Tothill, P. and D. W. Pye, (1992) *Br J Radiol,* 65:807-813; Svendsen, O. L., et al., (1995) *J Bone Min Res* 10:868-873. Moreover, DXA systems are large and expensive, ranging in price between $75,000 and $150,000.

Quantitative computed tomography (QCT) is usually applied to measure the trabecular bone in the vertebral bodies. Cann (1988) *Radiology* 166:509-522. QCT studies are generally performed using a single kV setting (single-energy QCT), when the principal source of error is the variable composition of the bone marrow. However, a dual-kV scan (dual-energy QCT) is also possible. This reduces the accuracy errors but at the price of poorer precision and higher radiation dose. Like DXA, however, QCT are very expensive and the use of such equipment is currently limited to few research centers.

Quantitative ultrasound (QUS) is a technique for measuring the peripheral skeleton. Njeh et al. (1997) *Osteoporosis Int* 7:7-22; Njeh et al. Quantitative Ultrasound: Assessment of Osteoporosis and Bone Status. 1999, London, England: Martin Dunitz. There is a wide variety of equipment available, with most devices using the heel as the measurement site. A sonographic pulse passing through bone is strongly attenuated as the signal is scattered and absorbed by trabeculae. Attenuation increases linearly with frequency, and the slope of the relationship is referred to as broadband ultrasonic attenuation (BUA; units: dB/MHz). BUA is reduced in patients with osteoporosis because there are fewer trabeculae in the calcaneus to attenuate the signal. In addition to BUA, most QUS systems also measure the speed of sound (SOS) in the heel by dividing the distance between the sonographic transducers by the propagation time (units: m/s). SOS values are reduced in patients with osteoporosis because with the loss of mineralized bone, the elastic modulus of the bone is decreased. There remain, however, several limitations to QUS measurements. The success of QUS in predicting fracture risk in younger patients remains uncertain. Another difficulty with QUS measurements is that they are not readily encompassed within the WHO definitions of osteoporosis and osteopenia. Moreover, no intervention thresholds have been developed. Thus, measurements cannot be used for therapeutic decision-making.

There are also several technical limitations to QUS. Many devices use a foot support that positions the patient's heel between fixed transducers. Thus, the measurement site is not readily adapted to different sizes and shapes of the calcaneus, and the exact anatomic site of the measurement varies from patient to patient. It is generally agreed that the relatively poor precision of QUS measurements makes most devices unsuitable for monitoring patients' response to treatment. Gluer (1997) *J Bone Min Res* 12:1280-1288.

Radiographic absorptiometry (RA) is a technique that was developed many years ago for assessing bone density in the hand, but the technique has recently attracted renewed interest. Gluer et al. (1997) *Semin Nucl Med* 27:229-247. With this technique, BMD is measured in the phalanges. The principal disadvantage of RA of the hand is the relative lack of high turnover trabecular bone. For this reason, RA of the hand has limited sensitivity in detecting osteoporosis and is not very useful for monitoring therapy-induced changes.

Peripheral x-ray absorptiometry methods such as those described above are substantially cheaper than DXA and QCT with system prices ranging between $15,000 and $35,000. However, epidemiologic studies have shown that the discriminatory ability of peripheral BMD measurements to predict spine and hip fractures is lower than when spine and hip BMD measurements are used. Cummings et al. (1993) *Lancet* 341:72-75; Marshall et al. (1996) *Br Med J* 312:1254-1259. The main reason for this is the lack of trabecular bone at the measurement sites used with these techniques. In addition, changes in forearm or hand BMD in response to hormone replacement therapy, bisphosphonates, and selective estrogen receptor modulators are relatively small, making such measurements less suitable than measurements of principally trabecular bone for monitoring response to treatment. Faulkner (1998) *J Clin Densitom* 1:279-285; Hoskings et al. (1998) *N Engl J Med* 338:485-492. Although attempts to obtain information on bone mineral density from dental x-rays have been attempted (See, e.g., Shrout et al. (2000) *J. Periodonol.* 71:335-340; Verhoeven et al. (1998) *Clin Oral Implants Res* 9(5):333-342), these have not provided accurate and reliable results.

Furthermore, current methods and devices do not generally take into account bone structure analyses. See, e.g., Ruttimann et al. (1992) *Oral Surg Oral Med Oral Pathol* 74:98-110; Southard & Southard (1992) *Oral Surg Oral Med Oral Pathol* 73:751-9; White & Rudolph, (1999) *Oral Surg Oral Med Oral Pathol Oral Radiol Endod* 88:628-35.

The present invention discloses novel methods and techniques for predicting musculoskeletal disease, particularly methods and compositions that result in the ability to obtain accurate predictions about disease based on bone mineral density and/or bone structure information obtained from images (e.g., radiographic images) and data.

SUMMARY OF THE INVENTION

The invention discloses a method for analyzing at least one of bone mineral density, bone structure and surrounding tissue. The method typically comprises: (a) obtaining an image of a subject; (b) locating a region of interest on the image; (c) obtaining data from the region of interest; and (d) deriving data selected from the group of qualitative and quantitative from the image data obtained at step c.

A system is also provided for predicting a disease. Any of these systems can include the steps of: (a) obtaining image data of a subject; (b) obtaining data from the image data wherein the data obtained is at least one of quantitative and qualitative data; and (c) comparing the at least one of quantitative and qualitative data in step b to at least one of: a database of at least one of quantitative and qualitative data obtained from a group of subjects; at least one of quantitative and qualitative data obtained from the subject; and at least one of a quantitative and qualitative data obtained from the subject at time Tn.

In certain aspects, described herein are methods of diagnosing, monitoring and/or predicting bone or articular disease (e.g., the risk of fracture) in a subject, the method comprising the steps of: determining one or more micro-structural parameters, one or more macroanatomical parameters or biomechanical parameters of a joint in said subject; and combining at least two of said parameters to predict the risk of bone or articular disease. The micro-structural, macroanatomical and/or biomechanical parameters may be, for example, one or more of the measurements/parameters shown in Tables 1, 2 and/or 3. In certain embodiments, one or more micro-structural parameters and one or more macro-anatomical parameters are combined. In other embodiments, one or more micro-structural parameters and one or more biomechanical parameters are combined. In further embodiments, one or more macroanatomical parameters and one or more biomechanical parameters are combined. In still further embodiments, one or more macroanatomical parameters, one or more micro-structural parameters and one or more biomechanical parameters are combined.

In any of the methods described herein, the comparing may be comprise univariate, bivariate and/or multivariate statistical analysis of one or more of the parameters. In certain embodiments, the methods may further comprise comparing said parameters to data derived from a reference database of known disease parameters.

In any of the methods described herein, the parameters are determined from an image obtained from the subject. In certain embodiments, the image comprises one or more regions of bone (e.g., patella, femur, tibia, fibula, pelvis, spine, etc). The image may be automatically or manually divided into two or more regions of interest. Furthermore, in any of the methods described herein, the image may be, for example, an x-ray image, a CT scan, an MRI or the like and optionally includes one or more calibration phantoms.

In any of the methods described herein, the predicting includes performing univariate, bivariate or multivariate statistical analysis of the analyzed data and referencing the statistical analysis values to a fracture risk model. Fracture risk models can comprise, for example, data derived from a reference database of known fracture loads with their corresponding values of macro-anatomical, micro-anatomical parameters, and/or clinical risk factors.

In another aspect, the invention includes a method of determining the effect of a candidate agent on a subject's prognosis for musculoskeletal disease comprising: predicting a first risk of musculoskeletal disease in subject according to any of the predictive methods described herein; administering a candidate agent to the subject; predicting a second risk of the musculoskeletal disease in the subject according to any of the predictive methods described herein; and comparing the first and second risks, thereby determining the effect of the candidate on the subject's prognosis for the disease. In any of these methods, the candidate agent can be administered to the subject in any modality, for example, by injection (intramuscular, subcutaneous, intravenous), by oral administration (e.g., ingestion), topical administration, mucosal administration or the like. Furthermore, the candidate agent may be a small molecule, a pharmaceutical, a biopharmaceutical, an agropharmaceuticals and/or combinations thereof.

In other aspects, the invention includes a kit that is provided for aiding in the prediction of musculoskeletal disease (e.g., fracture risk). The kit typically comprises a software program that uses information obtained from an image to predict the risk or disease (e.g., fracture). The kit can also include a database of measurements for comparison purposes. Additionally, the kit can include a subset of a database of measurements for comparisons.

In any of these methods, systems or kits, additional steps can be provided. Such additional steps include, for example, enhancing image data.

Suitable subjects for these steps include for example mammals, humans and horses. Suitable anatomical regions of subjects include, for example, dental, spine, hip, knee and bone core x-rays.

A variety of systems can be employed to practice the inventions. Typically at least one of the steps of any of the methods is performed on a first computer. Although, it is possible to have an arrangement where at least one of the steps of the method is performed on a first computer and at least one of the steps of the method is performed on a second computer. In this scenario the first computer and the second computer are typically connected. Suitable connections include, for example, a peer to peer network, direct link, intranet, and internet.

It is important to note that any or all of the steps of the inventions disclosed can be repeated one or more times in series or in parallel with or without the repetition of other steps in the various methods. This includes, for example repeating the step of locating a region of interest, or obtaining image data.

Data can also be converted from 2D to 3D to 4D and back; or from 2D to 4D. Data conversion can occur at multiple points of processing the information. For example, data conversion can occur before or after pattern evaluation and/or analysis.

Any data obtained, extracted or generated under any of the methods can be compared to a database, a subset of a database, or data previously obtained, extracted or generated from the subject. For example, known fracture load can be determined for a variety of subjects and some or all of this database can be used to predict fracture risk by correlating one or more macro-anatomical or structural parameters (Tables 1, 2 and/or 3) with data from a reference database of fracture load for age, sex, race, height and weight matched individuals.

The present invention provides methods that allow for the analysis of bone mineral density, bone and/or cartilage structure and morphology and/or surrounding tissue from images including electronic images and, accordingly, allows for the evaluation of the effect(s) of an agent (or agents) on bone and/or cartilage. It is important to note that an effect on bone and/or cartilage can occur in agents intended to have an effect, such as a therapeutic effect, on bone and/or cartilage as well as agents intended to primarily effect other tissues in the body but which have a secondary, or tangential, effect on bone and/or cartilage. The images (e.g., x-ray images) can be, for example, dental, hip, spine or other radiographs and can be taken from any mammal. The images can be in electronic format.

The invention includes a method to derive quantitative information on bone structure and/or bone mineral density from an image comprising (a) obtaining an image, wherein the image optionally includes an external standard for determining bone density and/or structure; and (b) analyzing the image obtained in step (a) to derive quantitative information on bone structure. The image is taken of a region of interest (ROI). Suitable ROI include, for example, a hip radiograph or a dental x-ray obtained on dental x-ray film, including the mandible, maxilla or one or more teeth. In certain embodiments, the image is obtained digitally, for example using a selenium detector system, a silicon detector system or a computed radiography system. In other embodiments, the image can be digitized from film, or another suitable source, for analysis.

A method is included where one or more candidate agents can be tested for its effects on bone. Again, the effect can be a primary effect or a secondary effect. For example, images obtained from the subject can be evaluated prior to administration of a candidate agent to predict the risk of disease in the absence of the agent. After administration of the candidate agent(s), an electronic image of the same portion of a bone of the subject can be obtained and analyzed as described herein to predict the risk of musculoskeletal disease. The risk of disease prior to administration of the candidate agent and after administration can then be compared to determine if the agent had any effect on disease prognosis. Information on bone structure can relate to a variety of parameters, including the parameters shown in Table 1, Table 2 and Table 3, infra. The images or data may also be compared to a database of images or data (e.g., "known" images or data). The candidate agent can, for example, be molecules, proteins, peptides, naturally occurring substances, chemically synthesized substances, or combinations and cocktails thereof. Typically, an agent includes one or more drugs. Further, the agent can be evaluated for the ability to effect bone diseases such as the risk of bone fracture (e.g., osteoporotic fracture).

In any of the methods described herein, the analysis can comprise using one or more computer programs (or units). Additionally, the analysis can comprise identifying one or more regions of interest (ROI) in the image, either prior to, concurrently or after analyzing the image, e.g. for information on bone mineral density and/or bone structure. The bone density information can be, for example, areas of highest, lowest or median density. Bone structural information can be, for example, one or more of the parameters shown in Table 1, Table 2 and Table 3. The various analyses can be performed concurrently or in series. Further, when using two or more indices each of the indices can be weighted equally or differently, or combinations thereof where more than two indices are employed. Additionally, any of these methods can also include analyzing the image for bone mineral density information using any of the methods described herein.

Any of the methods described herein can further comprise applying one or more correction factors to the data obtained from the image. For example, correction factors can be programmed into a computer unit. The computer unit can be the same one that performs the analysis of the image or can be a different unit. In certain embodiments, the correction factors account for the variation in soft-tissue thickness in individual subjects.

These and other embodiments of the subject invention will readily occur to those of skill in the art in light of the disclosure herein.

BRIEF DESCRIPTION OF THE DRAWINGS

FIG. 10 depicts regions of interest (ROIs) analyzed in Example 1.

FIG. 11 depicts results of biomechanical testing of 15 cadaveric hips and femurs.

FIG. 12A-B, are reproductions of x-ray images depicting an exemplary induced fracture in cadaveric femur resulting from biomechanical testing and load.

FIG. 13 is a graph depicting correlation of DXA femoral neck bone mineral density (BMD) versus biochemical fracture load as evaluated in 15 fresh cadaveric hip samples.

FIG. 14A-C are graphs depicting correlation of bone structure versus mechanical fracture load. FIG. 14A depicts correlation of maximum marrow spacing v. fracture load. FIG. 14B depicts correlation of maximum marrow spacing (log) v. fracture load. FIG. 14C depicts correlation of percentage of trabecular area v. fracture load.

FIG. 15A-C are graphs depicting correlation of macro-anatomical features versus biomechanical fracture load. FIG. 15A depicts correlation of cortical thickness v. fracture load. FIG. 15B depicts correlation of hip axis length (HAL) V. fracture load. FIG. 15C depicts correlation of cortical thickness (standard deviation) versus fracture load.

FIG. 16 is a graph depicting multivariate analysis using a combination of bone structural and macro-anatomical parameters and shows the correlation of predicted fracture load to actual fracture load.

DETAILED DESCRIPTION

The following description is presented to enable any person skilled in the art to make and use the invention. Various modifications to the embodiments described will be readily apparent to those skilled in the art, and the generic principles defined herein can be applied to other embodiments and applications without departing from the spirit and scope of the present invention as defined by the appended claims. Thus, the present invention is not intended to be limited to the embodiments shown, but is to be accorded the widest scope consistent with the principles and features disclosed herein. To the extent necessary to achieve a complete understanding of the invention disclosed, the specification and drawings of all issued patents, patent publications, and patent applications cited in this application are incorporated herein by reference.

The practice of the present invention employs, unless otherwise indicated, currently conventional methods of imaging and image processing within the skill of the art. Such techniques are explained fully in the literature. See, e.g., WO 02/22014, X-Ray Structure Determination: A Practical Guide, $2^{nd}$ Edition, editors Stout and Jensen, 1989, John Wiley & Sons, publisher; Body CT: A Practical Approach, editor Slone, 1999, McGraw-Hill publisher; The Essential Physics of Medical Imaging, editors Bushberg, Seibert, Leidholdt Jr & Boone, 2002, Lippincott, Williams & Wilkins; X-ray Diagnosis: A Physician's Approach, editor Lam, 1998 Springer-Verlag, publisher; Dental Radiology: Understanding the X-Ray Image, editor Laetitia Brocklebank 1997, Oxford University Press publisher; and Digital Image Processing, editor Kenneth R. Castleman, 1996 Prentice Hall, publisher; The Image Processing Handbook, editor John C. Russ, $3^{rd}$ Edition, 1998, CRC Press; Active Contours: The Application of Techniques from Graphics, Vision, Control Theory and Statistics to Visual Tracking of Shapes in Motion, Editors Andrew Blake, Michael Isard, 1999 Springer Verlag. As will be appreciated by those of skill in the art, as the field of imaging continues to advance methods of imaging currently employed can evolve over time. Thus, any imaging method or technique that is currently employed is appropriate for application of the teachings of this invention as well as techniques that can be developed in the future. A further detailed description of imaging methods is not provided in order to avoid obscuring the invention.

Figure 1A:
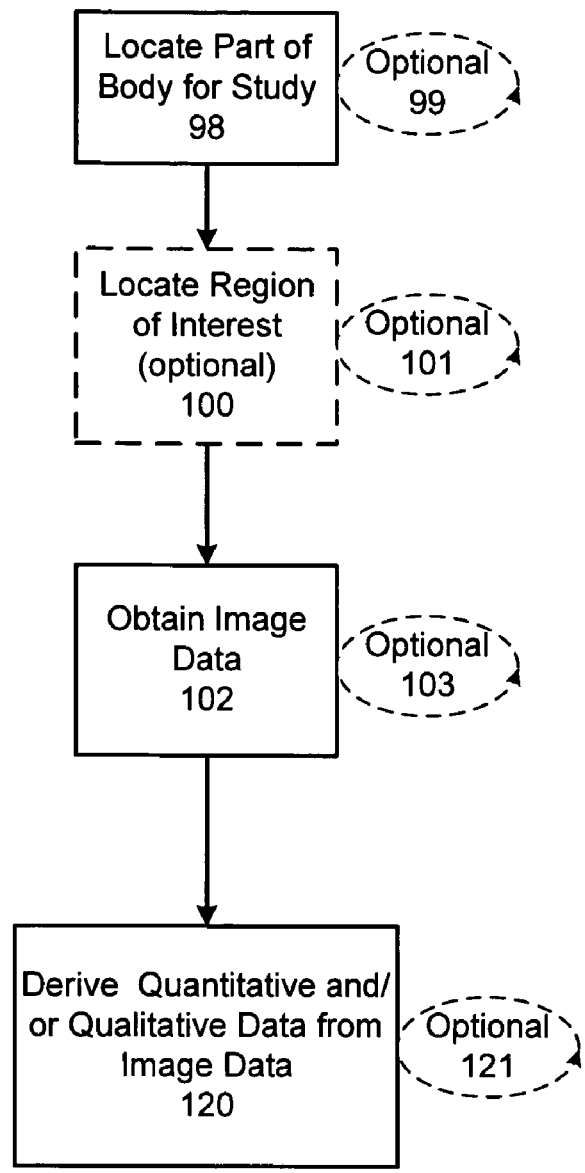
FIGS. 1A AND B are block diagrams showing the steps for extracting data from an image and then deriving quantitative and/or qualitative data from the image.

As shown in FIG. 1A, the first step is to locate a part of the body of a subject, for example in a human body, for study 98. The part of the body located for study is the region of anatomical interest (RAI). In locating a part of the body for study, a determination is made to, for example, take an image or a series of images of the body at a particular location, e.g. hip, dental, spine, etc. Images include, for example, conventional x-ray images, x-ray tomosynthesis, ultrasound (including A-scan, B-scan and C-scan) computed tomography (CT scan), magnetic resonance imaging (MRI), optical coherence tomography, single photon emission tomography (SPECT), and positron emission tomography, or such other imaging tools that a person of skill in the art would find useful in practicing the invention. Once the image is taken, a region of interest (ROI) can be located within the image 100. Algorithms can be used to automatically place regions of interest in a particular image. See, e.g., Example 1 describing automatic placement of ROIs in femurs. Image data is extracted from the image 102. Finally, quantitative and/or qualitative data is extracted from the image data 120. The quantitative and/or qualitative data extracted from the image includes, for example, the parameters and measurements shown in Table 1, Table 2 or 5 Table 3.

Each step of locating a part of the body for study 98, optionally locating a region of interest 100, obtaining image data 102, and deriving data 120, can be repeated one or more times 99, 101, 103, 121, respectively, as desired.

Figure 1B:
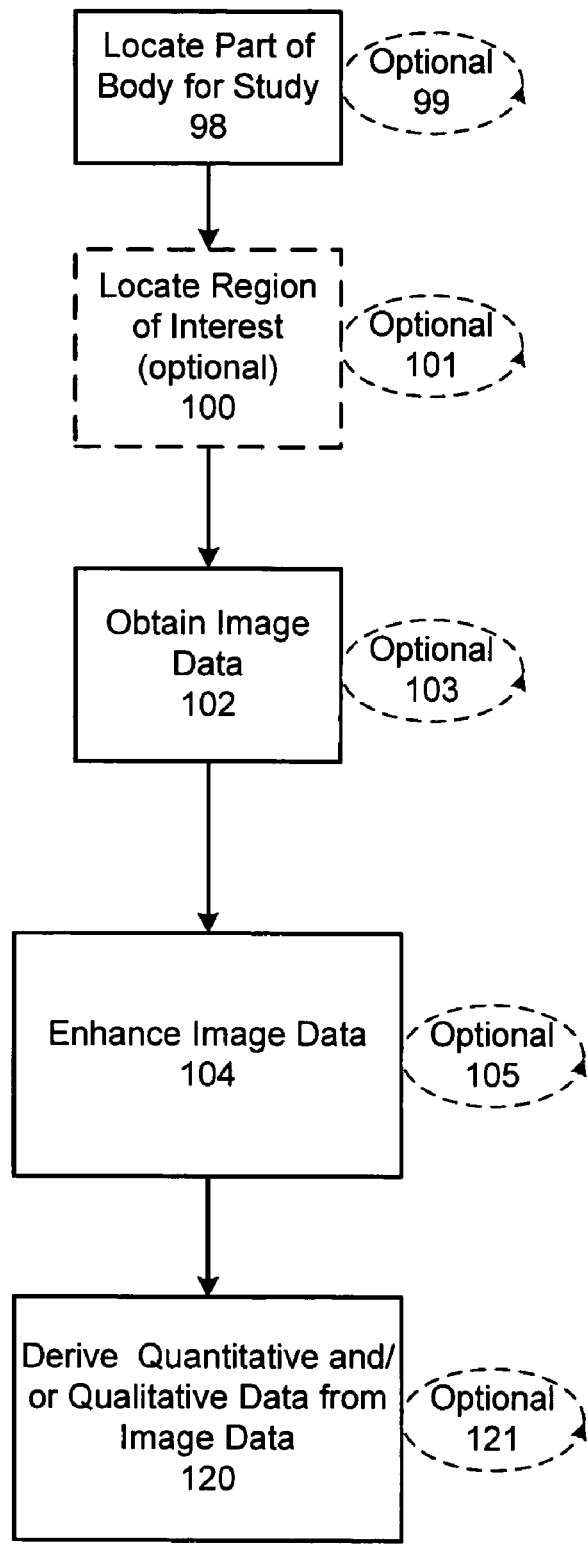

As shown in FIG. 1B image data can be optionally enhanced 104 by applying image processing techniques, such as noise filtering or diffusion filtering, to facilitate further analysis. Similar to the process shown in FIG. 1A, locating a part of the body for study 98, optionally locating a region of interest 100, obtaining image data 102, enhancing image data 104, and deriving data 120, can be repeated one or more times 99, 101, 103, 105, 121, respectively, as desired.

TABLE 1

Representative Parameters Measured with Quantitative and Qualitative Image Analysis Methods

| PARAMETER | MEASUREMENTS |
|---|---|
| Bone density and microstructural parameters | Calibration phantom equivalent thickness (Average intensity value of the region of interest expressed as thickness of calibration phantom that would produce the equivalent intensity) |
| | Trabecular contrast |
| | Standard deviation of background subtracted ROI |
| | Coefficient of Variation of ROI (Standard deviation/mean) |
| | (Trabecular equivalent thickness/Marrow equivalent thickness) |

TABLE 1-continued

Representative Parameters Measured with
Quantitative and Qualitative Image Analysis Methods

| PARAMETER | MEASUREMENTS |
|---|---|
| | Fractal dimension |
| | Hough transform |
| | Fourier spectral analysis |
| | (Mean transform coefficient absolute value and mean spatial first moment) |
| | Predominant orientation of spatial energy spectrum |
| | Trabecular area |
| | (Pixel count of extracted trabeculae) |
| | Trabecular area/Total area |
| | Trabecular perimeter |
| | (Count of trabecular pixels with marrow pixels in their neighborhood, proximity or vicinity) |
| | Trabecular distance transform |
| | (For each trabecular pixel, calculation of distance to closest marrow pixel) |
| | Marrow distance transform |
| | (For each marrow pixel, calculation of distance to closest trabecular pixel) |
| | Trabecular distance transform regional maximal values (mean, min., max, std. Dev). |
| | (Describes thickness and thickness variation of trabeculae) |
| | Marrow distance transform regional maximal values (mean, min., max, std. Dev) |
| | Star volume |
| | (Mean volume of all the parts of an object which can be seen unobscured from a random point inside the object in all possible directions) |
| | Trabecular Bone Pattern Factor |
| | (TBPf = (P1 − P2)/(A1 − A2) where P1 and A1 are the perimeter length and trabecular bone area before dilation and P2 and A2 corresponding values after a single pixel dilation, measure of connectivity) |
| | Connected skeleton count or Trees (T) |
| | Node count (N) |
| | Segment count (S) |
| | Node-to-node segment count (NN) |
| | Node-to-free-end segment count (NF) |
| | Node-to-node segment length (NNL) |
| | Node-to-free-end segment length (NFL) |
| | Free-end-to-free-end segment length (FFL) |
| | Node-to-node total struts length (NN.TSL) |
| | Free-end-to-free-ends total struts length(FF.TSL) |
| | Total struts length (TSL) |
| | FF.TSL/TSL |
| | NN.TSL/TSL |
| | Loop count (Lo) |
| | Loop area |
| | Mean distance transform values for each connected skeleton |
| | Mean distance transform values for each segment (Tb.Th) |
| | Mean distance transform values for each node-to-node segment (Tb.Th.NN) |
| | Mean distance transform values for each node-to-free-end segment (Tb.Th.NF) |
| | Orientation (angle) of each segment |
| | Angle between segments |
| | Length-thickness ratios (NNL/Tb.Th.NN) and (NFL/Tb.Th.NF) |
| | Interconnectivity index (ICI) ICI = (N * NN)/(T * (NF + 1)) |
| Cartilage and cartilage defect/diseased cartilage parameters | Total cartilage volume |
| | Partial/Focal cartilage volume |
| | Cartilage thickness distribution (thickness map) |
| | Mean cartilage thickness for total region or focal region |
| | Median cartilage thickness for total region or focal region |
| | Maximum cartilage thickness for total region or focal region |
| | Minimum cartilage thickness for total region or focal region |
| | 3D cartilage surface information for total region or focal region |
| | Cartilage curvature analysis for total region or focal region |
| | Volume of cartilage defect/diseased cartilage |
| | Depth of cartilage defect/diseased cartilage |
| | Area of cartilage defect/diseased cartilage |
| | 2D or 3D location of cartilage defect/diseased cartilage in articular surface |
| | 2D or 3D location of cartilage defect/diseased cartilage in relationship to weight-bearing area |

TABLE 1-continued

Representative Parameters Measured with
Quantitative and Qualitative Image Analysis Methods

| PARAMETER | MEASUREMENTS |
|---|---|
| | Ratio: diameter of cartilage defect or diseased cartilage/thickness of surrounding normal cartilage |
| | Ratio: depth of cartilage defect or diseased cartilage/thickness of surrounding normal cartilage |
| | Ratio: volume of cartilage defect or diseased cartilage/thickness of surrounding normal cartilage |
| | Ratio: surface area of cartilage defect or diseased cartilage/total joint or articular surface area |
| | Ratio: volume of cartilage defect or diseased cartilage/total cartilage volume |
| Other articular parameters | Presence or absence of bone marrow edema |
| | Volume of bone marrow edema |
| | Volume of bone marrow edema normalized by width, area, size, volume of femoral condyle(s)/tibial plateau/patella —other bones in other joints |
| | Presence or absence of osteophytes |
| | Presence or absence of subchondral cysts |
| | Presence or absence of subchondral sclerosis |
| | Volume of osteophytes |
| | Volume of subchondral cysts |
| | Volume of subchondral sclerosis |
| | Area of bone marrow edema |
| | Area of osteophytes |
| | Area of subchondral cysts |
| | Area of subchondral sclerosis |
| | Depth of bone marrow edema |
| | Depth of osteophytes |
| | Depth of subchondral cysts |
| | Depth of subchondral sclerosis |
| | Volume, area, depth of osteophytes, subchondral cysts, subchondral sclerosis normalized by width, area, size, volume of femoral condyle(s)/tibial plateau/patella —other bones in other joints |
| | Presence or absence of meniscal tear |
| | Presence or absence of cruciate ligament tear |
| | Presence or absence of collateral ligament tear |
| | Volume of menisci |
| | Ratio of volume of normal to torn/damaged or degenerated meniscal tissue |
| | Ratio of surface area of normal to torn/damaged or degenerated meniscal tissue |
| | Ratio of surface area of normal to torn/damaged or degenerated meniscal tissue to total joint or cartilage surface area |
| | Ratio of surface area of torn/damaged or degenerated meniscal tissue to total joint or cartilage surface area |
| | Size ratio of opposing articular surfaces |
| | Meniscal subluxation/dislocation in mm |
| | Index combining different articular parameters which can also include |
| | Presence or absence of cruciate or collateral ligament tear |
| | Body mass index, weight, height |
| | 3D surface contour information of subchondral bone |
| | Actual or predicted knee flexion angle during gait cycle (latter based on gait patterns from subjects with matching demographic data retrieved from motion profile database) |
| | Predicted knee rotation during gait cycle |
| | Predicted knee displacement during gait cycle |
| | Predicted load bearing line on cartilage surface during gait cycle and measurement of distance between load bearing line and cartilage defect/diseased cartilage |
| | Predicted load bearing area on cartilage surface during gait cycle and measurement of distance between load bearing area and cartilage defect/diseased cartilage |
| | Predicted load bearing line on cartilage surface during standing or different degrees of knee flexion and extension and measurement of distance between load bearing line and cartilage defect/diseased cartilage |
| | Predicted load bearing area on cartilage surface during standing or different degrees of knee flexion and extension and measurement of distance between load bearing area and cartilage defect/diseased cartilage |
| | Ratio of load bearing area to area of cartilage defect/diseased cartilage |

TABLE 1-continued

Representative Parameters Measured with
Quantitative and Qualitative Image Analysis Methods

| PARAMETER | MEASUREMENTS |
|---|---|
| | Percentage of load bearing area affected by cartilage disease
Location of cartilage defect within load bearing area
Load applied to cartilage defect, area of diseased cartilage
Load applied to cartilage adjacent to cartilage defect, area of diseased cartilage |

As will be appreciated by those of skill in the art, the parameters and measurements shown in Table 1 are provided for illustration purposes. It will be apparent that the terms micro-structural parameters, micro-architecture, micro-anatomic structure, micro-structural and trabecular architecture may be used interchangably. In additon, other parameters and measurements, ratios, derived values or indices can be used to extract quantitative and/or qualitative information about the ROI without departing from the scope of the invention. Additionally, where multiple ROI or multiple derivatives of data are used, the parameter measured can be the same parameter or a different parameter without departing from the scope of the invention. Additionally, data from different ROIs can be combined or compared as desired.

Additional measurements can be performed that are selected based on the anatomical structure to be studied as described below.

Once the data is extracted from the image it can be manipulated to assess the severity of the disease and to determine disease staging (e.g., mild, moderate, severe or a numerical value or index). The information can also be used to monitor progression of the disease and/or the efficacy of any interventional steps that have been taken. Finally, the information can be used to predict the progression of the disease or to randomize patient groups in clinical trials.

Figure 2A:
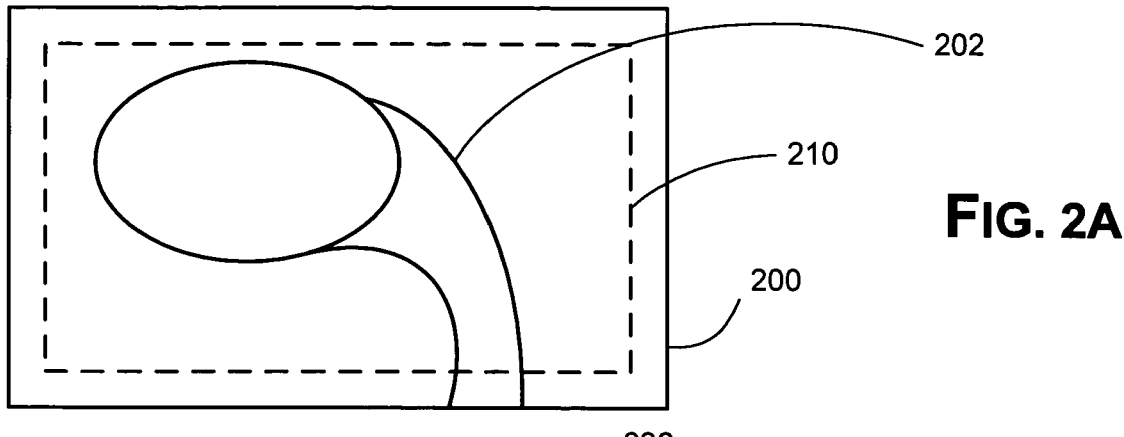
FIGS. 2A-C are diagrams showing an image taken of a region of anatomical interest further illustrating possible locations of regions of interest for analysis.
Figure 2B:
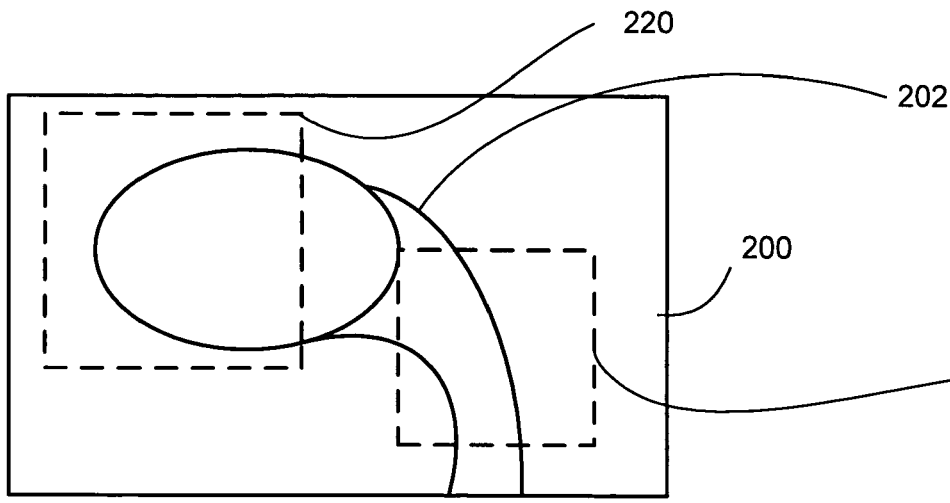
Figure 2C:
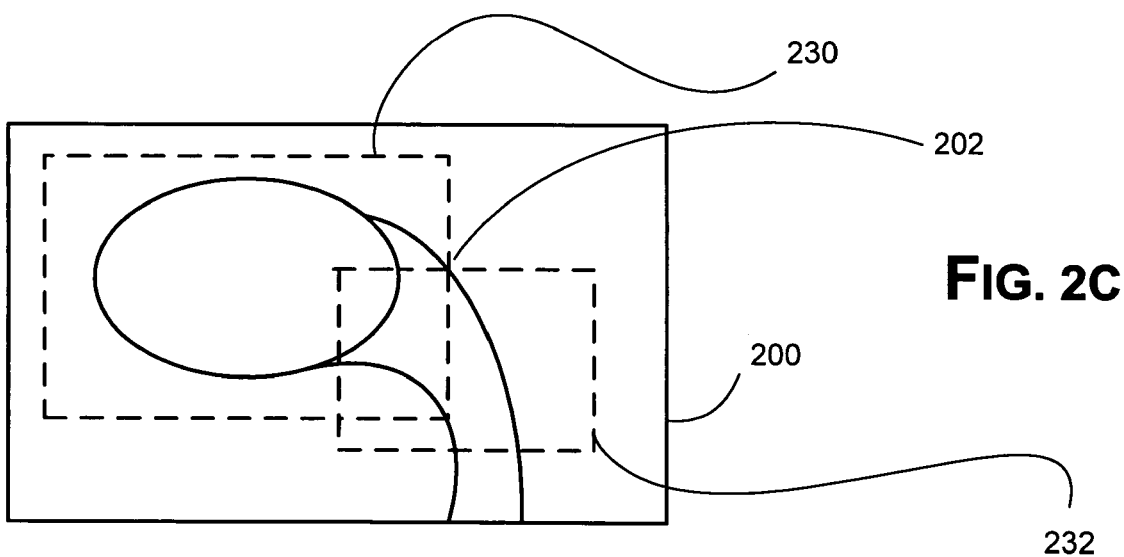

FIG. 2A illustrates an image 200 taken of an RAI, shown as 202. As shown in FIG. 2A, a single region of interest (ROI) 210 has been identified within the image. The ROI 210 can take up the entire image 200, or nearly the entire image. As shown in FIG. 2B more than one ROI can be identified in an image. In this example, a first ROI 220 is depicted in one region of the image 200, and a second ROI 222 is depicted within the image. In this instance, neither of these ROI overlap or abut. As will be appreciated by a person of skill in the art, the number of ROI identified in an image 200 is not limited to the two depicted. Turning now to FIG. 2C another embodiment showing two ROI for illustration purposes is shown. In this instance, the first ROI 230 and the second ROI 232, are partially overlapping. As will be appreciated by those of skill in the art, where multiple ROI are used any or all of the ROI can be organized such that it does not overlap, it abuts without overlapping, it overlaps partially, it overlaps completely (for example where a first ROI is located completely within a second identified ROI), and combinations thereof. Further the number of ROI per image 200 can range from one ($ROI_1$) to n ($ROI_n$) where n is the number of ROI to be analyzed.

Bone density, microarchitecture, macro-anatomic and/or biomechanical (e.g. derived using finite element modeling) analyses can be applied within a region of predefined size and shape and position. This region of interest can also be referred to as a "window." Processing can be applied repeatedly within the window at different positions of the image. For example, a field of sampling points can be generated and the analysis performed at these points. The results of the analyses for each parameter can be stored in a matrix space, e.g., where its position corresponds to the position of the sampling point where the analysis occurred, thereby forming a map of the spatial distribution of the parameter (a parameter map). The sampling field can have regular intervals or irregular intervals with varying density across the image. The window can have variable size and shape, for example to account for different patient size or anatomy.

The amount of overlap between the windows can be determined, for example, using the interval or density of the sampling points (and resolution of the parameter maps). Thus, the density of sampling points is set higher in regions where higher resolution is desired and set lower where moderate resolution is sufficient, in order to improve processing efficiency. The size and shape of the window would determine the local specificity of the parameter. Window size is preferably set such that it encloses most of the structure being measured. Oversized windows are generally avoided to help ensure that local specificity is not lost.

The shape of the window can be varied to have the same orientation and/or geometry of the local structure being measured to minimize the amount of structure clipping and to maximize local specificity. Thus, both 2D and/or 3D windows can be used, as well as combinations thereof, depending on the nature of the image and data to be acquired.

In another embodiment, bone density, microarchitecture, macro-anatomic and/or biomechanical (e.g. derived using finite element modeling) analyses can be applied within a region of predefined size and shape and position. The region is generally selected to include most, or all, of the anatomic region under investigation and, preferably, the parameters can be assessed on a pixel-by-pixel basis (e.g., in the case of 2D or 3D images) or a voxel-by-voxel basis in the case of cross-sectional or volumetric images (e.g., 3D images obtained using MR and/or CT). Alternatively, the analysis can be applied to clusters of pixels or voxels wherein the size of the clusters is typically selected to represent a compromise between spatial resolution and processing speed. Each type of analysis can yield a parameter map.

Parameter maps can be based on measurement of one or more parameters in the image or window; however, parameter maps can also be derived using statistical methods. In one embodiment, such statistical comparisons can include comparison of data to a reference population, e.g. using a z-score or a T-score. Thus, parameter maps can include a display of z-scores or T-scores.

Additional measurements relating to the site to be measured can also be taken. For example, measurements can be directed to dental, spine, hip, knee or bone cores. Examples of suitable site specific measurements are shown in Table 2.

TABLE 2

| | Site specific measurement of bone parameters |
|---|---|
| Parameters specific to hip images | All microarchitecture parameters on structures parallel to stress lines |
| | All microarchitecture parameters on structures perpendicular to stress lines |
| | Geometry |
| | Shaft angle |
| | Neck angle |
| | Average and minimum diameter of femur neck |
| | Hip axis length |
| | CCD (caput-collum-diaphysis) angle |
| | Width of trochanteric region |
| | Largest cross-section of femur head |
| | Standard deviation of cortical bone thickness within ROI |
| | Minimum, maximum, mean and median thickness of cortical bone within ROI |
| | Hip joint space width |
| Parameters specific to spine images | All microarchitecture parameters on vertical structures |
| | All microarchitecture parameters on horizontal structures Geometry |
| | Superior endplate cortical thickness (anterior, center, posterior) |
| | Inferior endplate cortical thickness (anterior, center, posterior) |
| | Anterior vertebral wall cortical thickness (superior, center, inferior) |
| | Posterior vertebral wall cortical thickness (superior, center, inferior) |
| | Superior aspect of pedicle cortical thickness |
| | inferior aspect of pedicle cortical thickness |
| | Vertebral height (anterior, center, posterior) |
| | Vertebral diameter (superior, center, inferior), |
| | Pedicle thickness (supero-inferior direction). |
| | Maximum vertebral height |
| | Minimum vertebral height |
| | Average vertebral height |
| | Anterior vertebral height |
| | Medial vertebral height |
| | Posterior vertebral height |
| | Maximum inter-vertebral height |
| | Minimum inter-vertebral height |
| | Average inter-vertebral height |
| Parameters specific to knee images | Average medial joint space width |
| | Minimum medial joint space width |
| | Maximum medial joint space width |
| | Average lateral joint space width |
| | Minimum lateral joint space width |
| | Maximum lateral joint space width |

As will be appreciated by those of skill in the art, measurement and image processing techniques are adaptable to be applicable to both microarchitecture and macro-anatomical structures. Examples of these measurements are shown in Table 3.

TABLE 3

| Measurements applicable on Microarchitecture and Macro-anatomical Structures | |
|---|---|
| Average density measurement | Calibrated density of ROI |
| Measurements on micro-anatomical structures of dental, spine, hip, knee or bone cores images | The following parameters are derived from the extracted structures: Calibrated density of extracted structures Calibrated density of background Average intensity of extracted structures Average intensity of background (area other than extracted structures) Structural contrast (average intensity of extracted structures/ average intensity of background) Calibrated structural contrast (calibrated density extracted structures/calibrated density of background) Total area of extracted structures Total area of ROI Area of extracted structures normalized by total area of ROI Boundary lengths (perimeter) of extracted normalized by total area of ROI Number of structures normalized by area of ROI Trabecular bone pattern factor; measures concavity and convexity of structures Star volume of extracted structures Star volume of background Number of loops normalized by area of ROI |
| Measurements on Distance transform of extracted structures | The following statistics are measured from the distance transform regional maximum values: Average regional maximum thickness Standard deviation of regional maximum thickness Largest value of regional maximum thickness Median of regional maximum thickness |
| Measurements on skeleton of extracted structures | Average length of networks (units of connected segments) Maximum length of networks Average thickness of structure units (average distance transform values along skeleton) Maximum thickness of structure units (maximum distance transform values along skeleton) Number of nodes normalized by ROI area Number of segments normalized by ROI area Number of free-end segments normalized by ROI area Number of inner (node-to-node) segments normalized ROI area Average segment lengths Average free-end segment lengths |

TABLE 3-continued

Measurements applicable on Microarchitecture and Macro-anatomical Structures

| | |
|---|---|
| | Average inner segment lengths |
| | Average orientation angle of segments |
| | Average orientation angle of inner segments |
| | Segment tortuosity; a measure of straightness |
| | Segment solidity; another measure of straightness |
| | Average thickness of segments (average distance transform values along skeleton segments) |
| | Average thickness of free-end segments |
| | Average thickness of inner segments |
| | Ratio of inner segment lengths to inner segment thickness |
| | Ratio of free-end segment lengths to free-end segment thickness |
| | Interconnectivity index; a function of number of inner segments, free-end segments and number of networks. |
| Directional skeleton segment measurements | All measurement of skeleton segments can be constrained by one or more desired orientation by measuring only skeleton segments within ranges of angle. |
| Watershed segmentation | Watershed segmentation is applied to gray level images. Statistics of watershed segments are: |
| | Total area of segments |
| | Number of segments normalized by total area of segments |
| | Average area of segments |
| | Standard deviation of segment area |
| | Smallest segment area |
| | Largest segment area |

As noted above, analysis can also include one or more additional techniques include, for example, Hough transform, mean pixel intensity analysis, variance of pixel intensity analysis, soft tissue analysis and the like. See, e.g., co-owned International Application WO 02/30283.

Calibrated density typically refers to the measurement of intensity values of features in images converted to its actual material density or expressed as the density of a reference material whose density is known. The reference material can be metal, polymer, plastics, bone, cartilage, etc., and can be part of the object being imaged or a calibration phantom placed in the imaging field of view during image acquisition.

Extracted structures typically refer to simplified or amplified representations of features derived from images. An example would be binary images of trabecular patterns generated by background subtraction and thresholding. Another example would be binary images of cortical bone generated by applying an edge filter and thresholding. The binary images can be superimposed on gray level images to generate gray level patterns of structure of interest.

Distance transform typically refers to an operation applied on binary images where maps representing distances of each 0 pixel to the nearest 1 pixel are generated. Distances can be calculated by the Euclidian magnitude, city-block distance, La Place distance or chessboard distance.

Distance transform of extracted structures typically refer to distance transform operation applied to the binary images of extracted structures, such as those discussed above with respect to calibrated density.

Skeleton of extracted structures typically refer to a binary image of 1 pixel wide patterns, representing the centerline of extracted structures. It is generated by applying a skeletonization or medial transform operation, by mathematical morphology or other methods, on an image of extracted structures.

Skeleton segments typically are derived from skeleton of extracted structures by performing pixel neighborhood analysis on each skeleton pixel. This analysis classifies each skeleton pixel as a node pixel or a skeleton segment pixel. A node pixel has more than 2 pixels in its 8-neighborhood. A skeleton segment is a chain of skeleton segment pixels continuously 8-connected. Two skeleton segments are separated by at least one node pixel.

Watershed segmentation as it is commonly known to a person of skill in the art, typically is applied to gray level images to characterize gray level continuity of a structure of interest. The statistics of dimensions of segments generated by the process are, for example, those listed in Table 3 above. As will be appreciated by those of skill in the art, however, other processes can be used without departing from the scope of the invention.

Figure 3A:
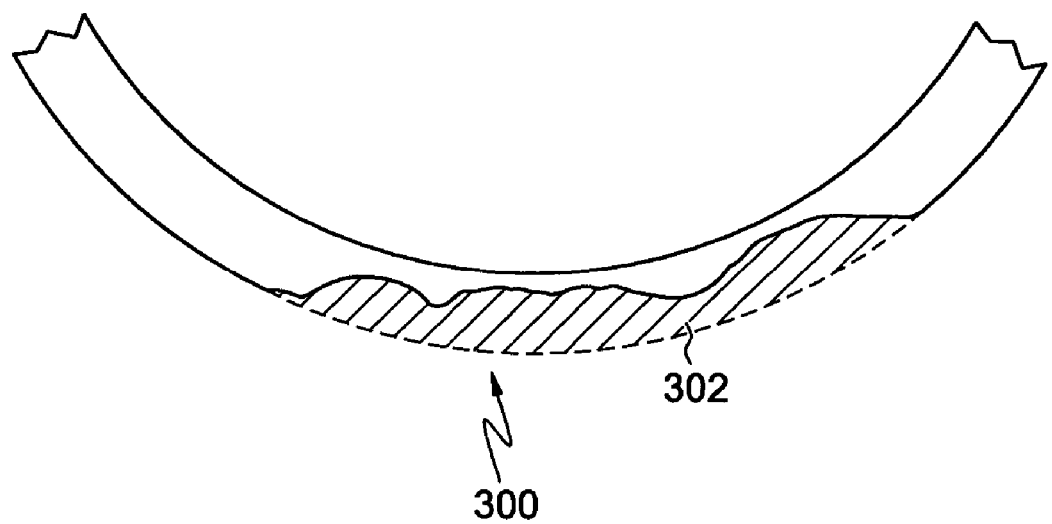
FIGS. 3A-J illustrate various abnormalities that might occur including, for example, cartilage defects, bone marrow edema, subchondral sclerosis, osteophytes and cysts.
Figure 3B:
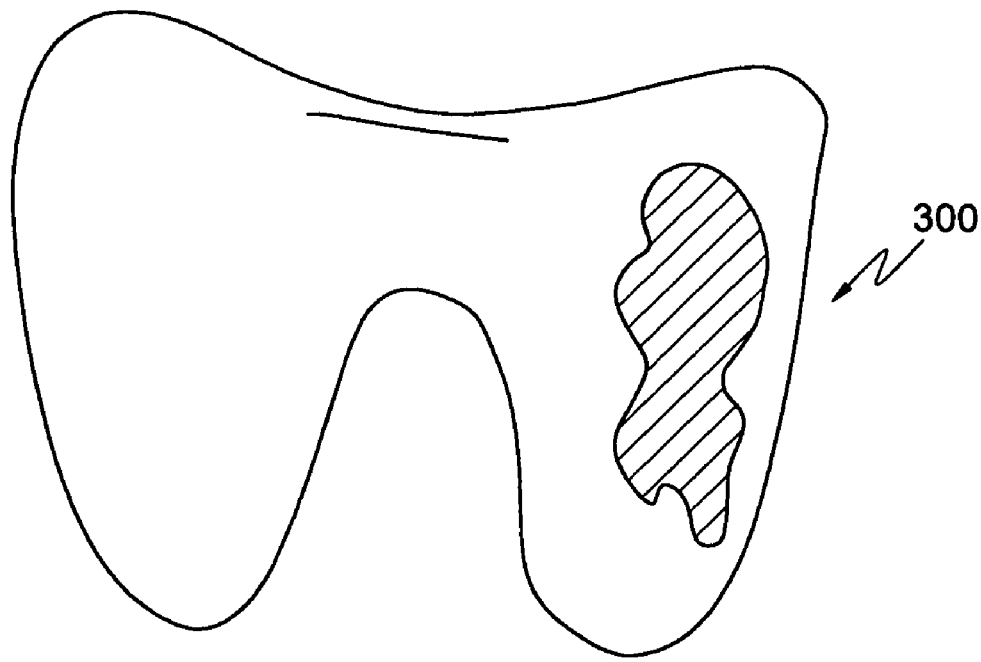

Turning now to FIG. 3A, a cross-section of a cartilage defect is shown 300. The cross-hatched zone 302 corresponds to an area where there is cartilage loss. FIG. 3B is a top view of the cartilage defect shown in FIG. 3A.

Figure 3C:
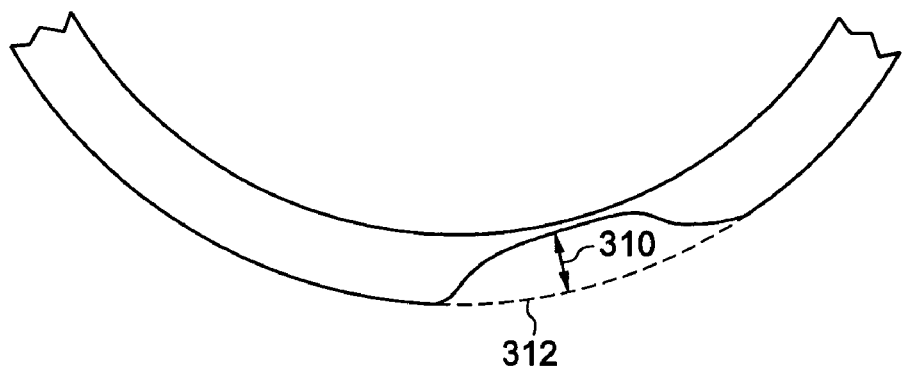

FIG. 3C illustrates the depth of a cartilage defect 310 in a first cross-section dimension with a dashed line illustrating a projected location of the original cartilage surface 312. By comparing these two values a ratio of cartilage defect depth to cartilage defect width can be calculated.

Figure 3D:
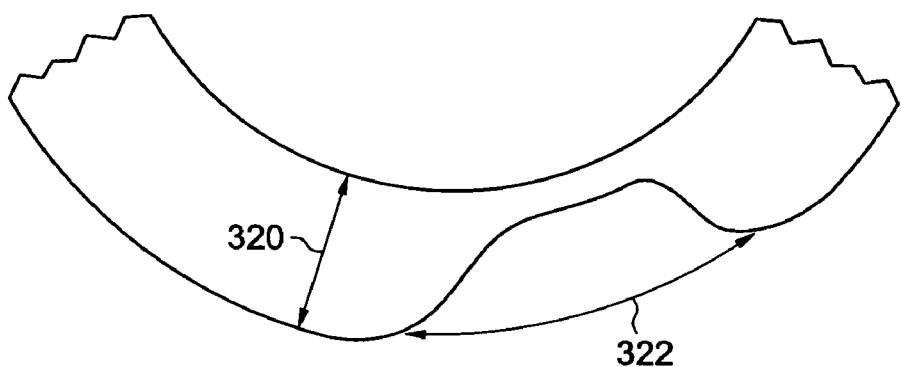

FIG. 3D illustrated the depth of the cartilage 320 along with the width of the cartilage defect 322. These two values can be compared to determine a ratio of cartilage depth to cartilage defect width.

Figure 3E:
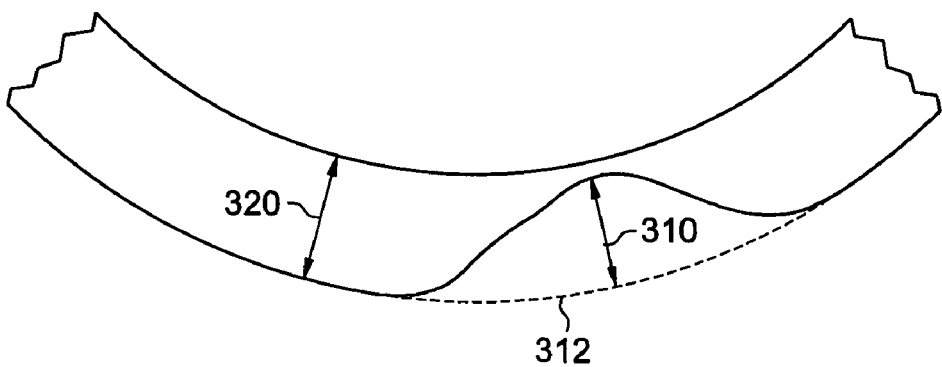

FIG. 3E shows the depth of the cartilage defect 310 along with the depth of the cartilage 320. A dashed line is provided illustrating a projected location for the original cartilage surface 312. Similar to the measurements made above, ratios between the various measurements can be calculated.

Figure 3F:
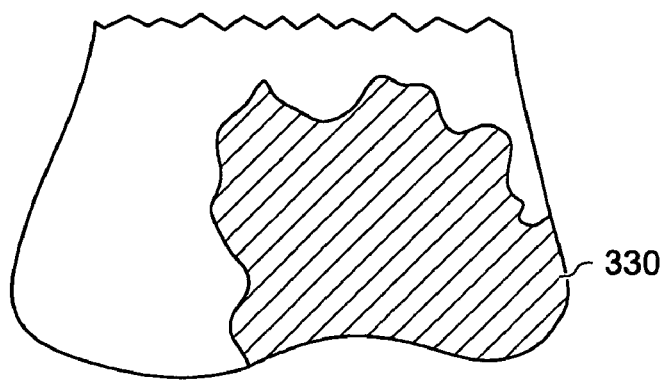
Figure 3F:
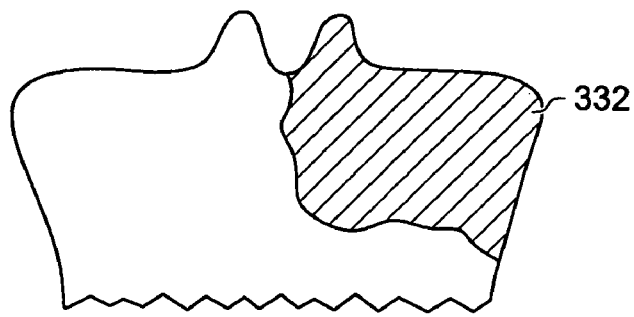

Turning now to FIG. 3F, an area of bone marrow edema is shown on the femur 330 and the tibia 332. The shaded area of edema can be measured on a T2-weighted MRI scan. Alternatively, the area can be measured on one or more slices. These measurements can then be extended along the entire joint using multiple slices or a 3D acquisition. From these measurements volume can be determined or derived.

Figure 3G:
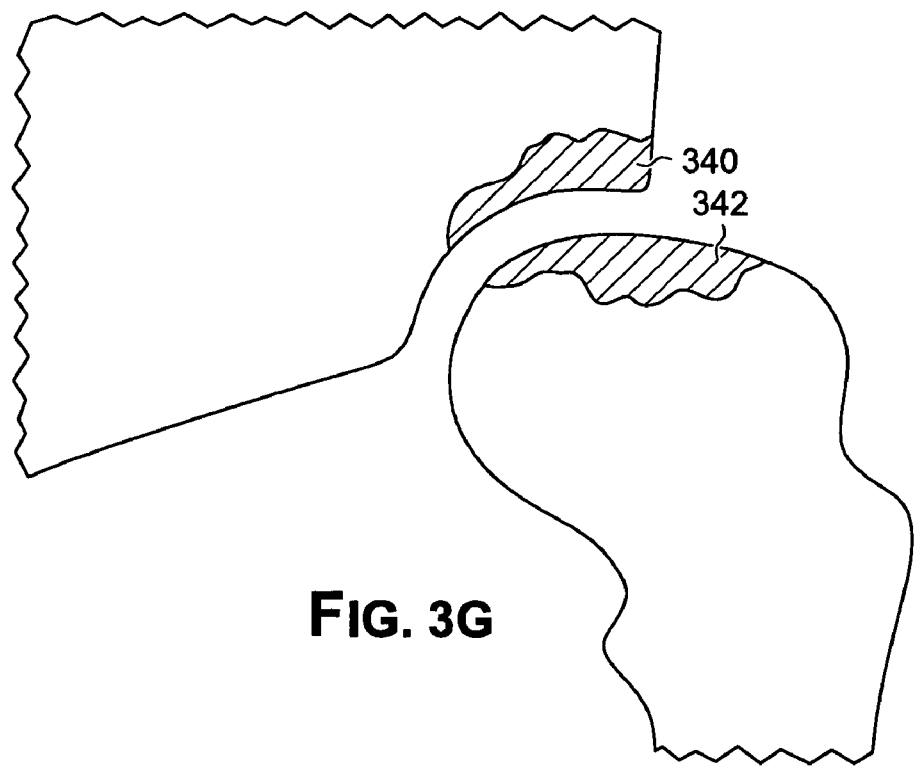

FIG. 3G shows an area of subchondral sclerosis in the acetabulum 340 and the femur 342. The sclerosis can be measured on, for example, a T1 or T2-weighted MRI scan or on a CT scan. The area can be measured on one or more slices.

Thereafter the measurement can be extended along the entire joint using multiple slices or a 3D acquisition. From these values a volume can be derived of the subchondral sclerosis. For purposes of illustration, a single sclerosis has been shown on each surface. However, a person of skill in the art will appreciate that more than one sclerosis can occur on a single joint surface.

Figure 3H:
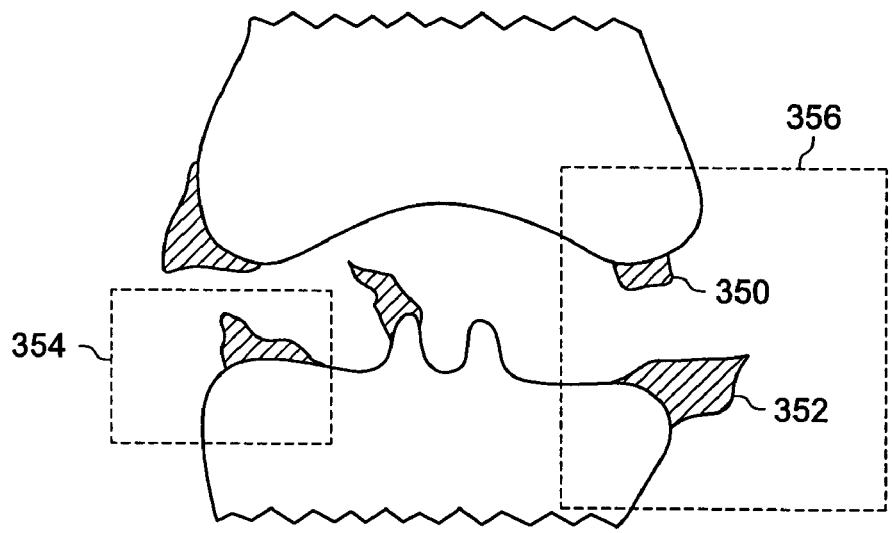

FIG. 3H shows osteophytes on the femur 350 and the tibia 352. The osteophytes are shown as cross-hatched areas. Similar to the sclerosis shown in FIG. 3G, the osteophytes can be measured on, for example, a T1 or T2-weighted MRI scan or on a CT scan. The area can be measured on one or more slices. Thereafter the measurement can be extended along the entire joint using multiple slices or a 3D acquisition. From these values a volume can be derived of the osteophytes. Additionally, a single osteophyte 354 or osteophyte groups 356 can be included in any measurement. Persons of skill in the art will appreciate that groups can be taken from a single joint surface or from opposing joint surfaces, as shown, without departing from the scope of the invention.

Figure 3I:
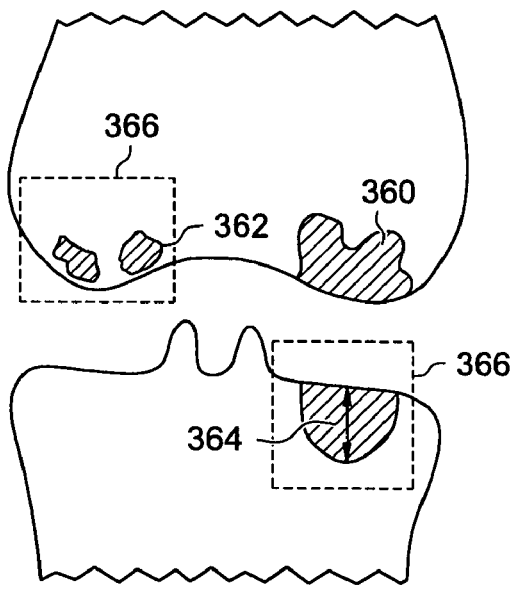

Turning now to FIG. 3I an area of subchondral cysts 360, 362, 364 is shown. Similar to the sclerosis shown in FIG. 3G, the cysts can be measured on, for example, a T1 or T2-weighted MRI scan or on a CT scan. The area can be measured on one or more slices. Thereafter the measurement can be extended along the entire joint using multiple slices or a 3D acquisition. From these values a volume can be derived of the cysts. Additionally, single cysts 366 or groups of cysts 366' can be included in any measurement. Persons of skill in the art will appreciate that groups can be taken from a single joint surface, as shown, or from opposing joint surfaces without departing from the scope of the invention.

Figure 3J:
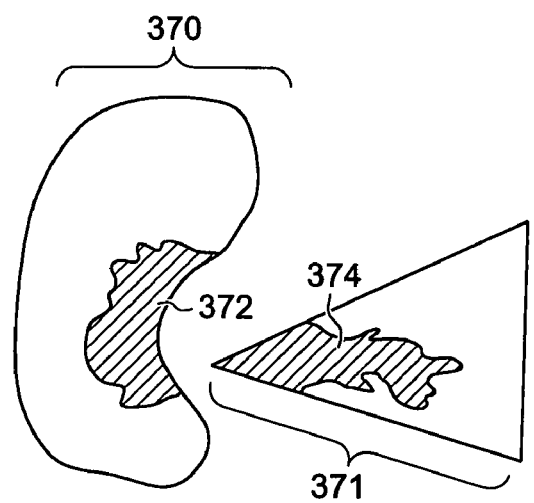

FIG. 3J illustrates an area of torn meniscal tissue (cross-hatched) 372, 374 as seen from the top 370 and in cross-section 371. Again, similar to the sclerosis shown in FIG. 3G, the torn meniscal tissue can be measured on, for example, a T1 or T2-weighted MRI scan or on a CT scan. The area can be measured on one or more slices. Thereafter the measurement can be extended along the entire joint using multiple slices or a 3D acquisition. From these values a volume can be derived of the tear. Ratios such as surface or volume of torn to normal meniscal tissue can be derived as well as ratios of surface of torn meniscus to surface of opposing articulating surface.

Figure 4A:
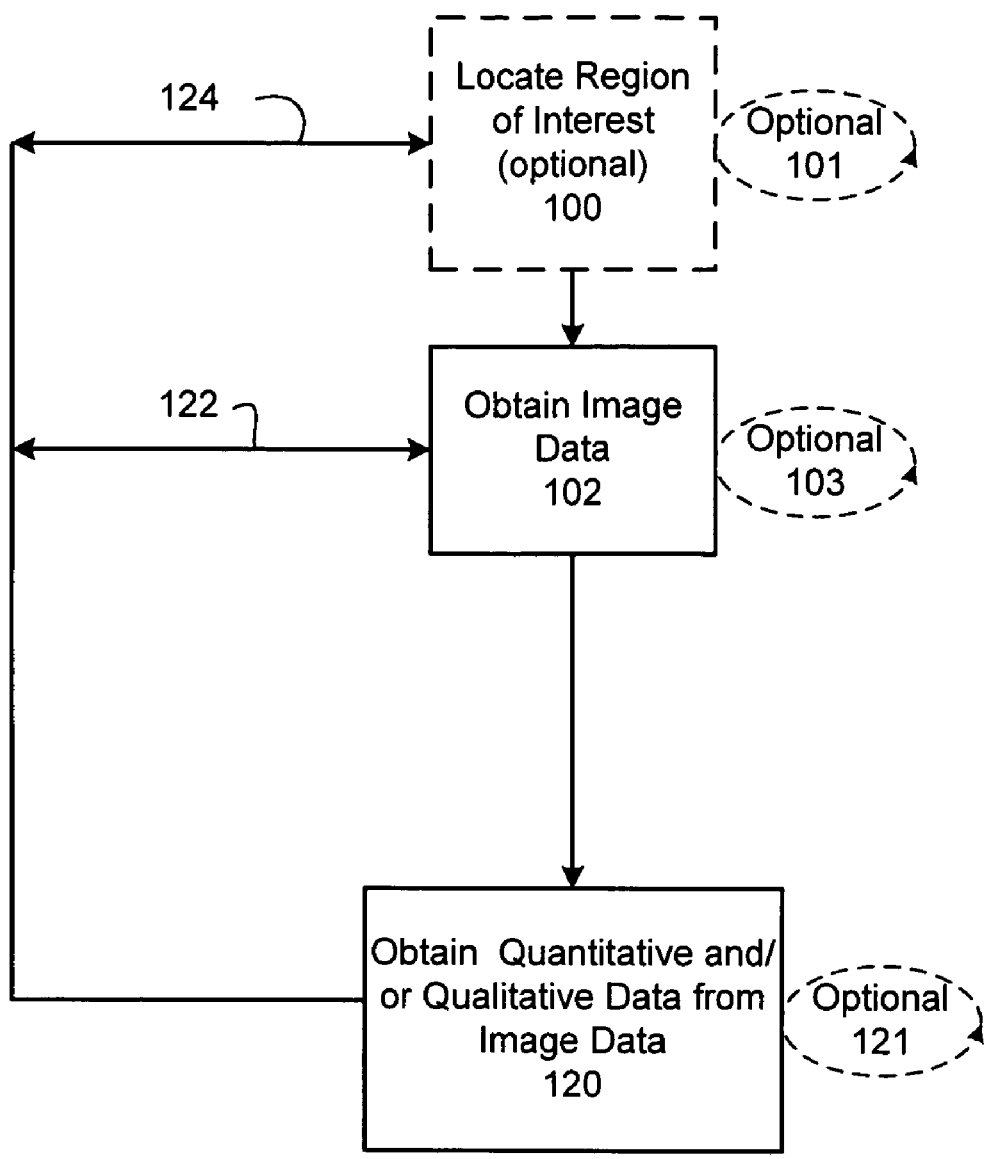
FIGS. 4A AND B are block diagrams of the method of FIG. 1A showing that the steps can be repeated.

As shown in FIG. 4A, the process of optionally locating a ROI 100, extracting image data from the ROI 102, and deriving quantitative and/or qualitative image data from the extracted image data 120, can be repeated 122. Alternatively, or in addition, the process of locating a ROI 100, can be repeated 124. A person of skill in the art will appreciate that these steps can be repeated one or more times in any appropriate sequence, as desired, to obtain a sufficient amount of quantitative and/or qualitative data on the ROI or to separately extract or evaluate parameters. Further, the ROI used can be the same ROI as used in the first process or a newly identified ROI in the image. Additionally, as with FIG. 1A the steps of locating a region of interest 100, obtaining image data 102, and deriving quantitative and/or qualitative image data can be repeated one or more times, as desired, 101, 103, 121, respectively. Although not depicted here, as discussed above with respect to FIG. 1A, the additional step of locating a part of the body for study 98 can be performed prior to locating a region of interest 100 without departing from the invention. Additionally that step can be repeated 99.

Figure 4B:
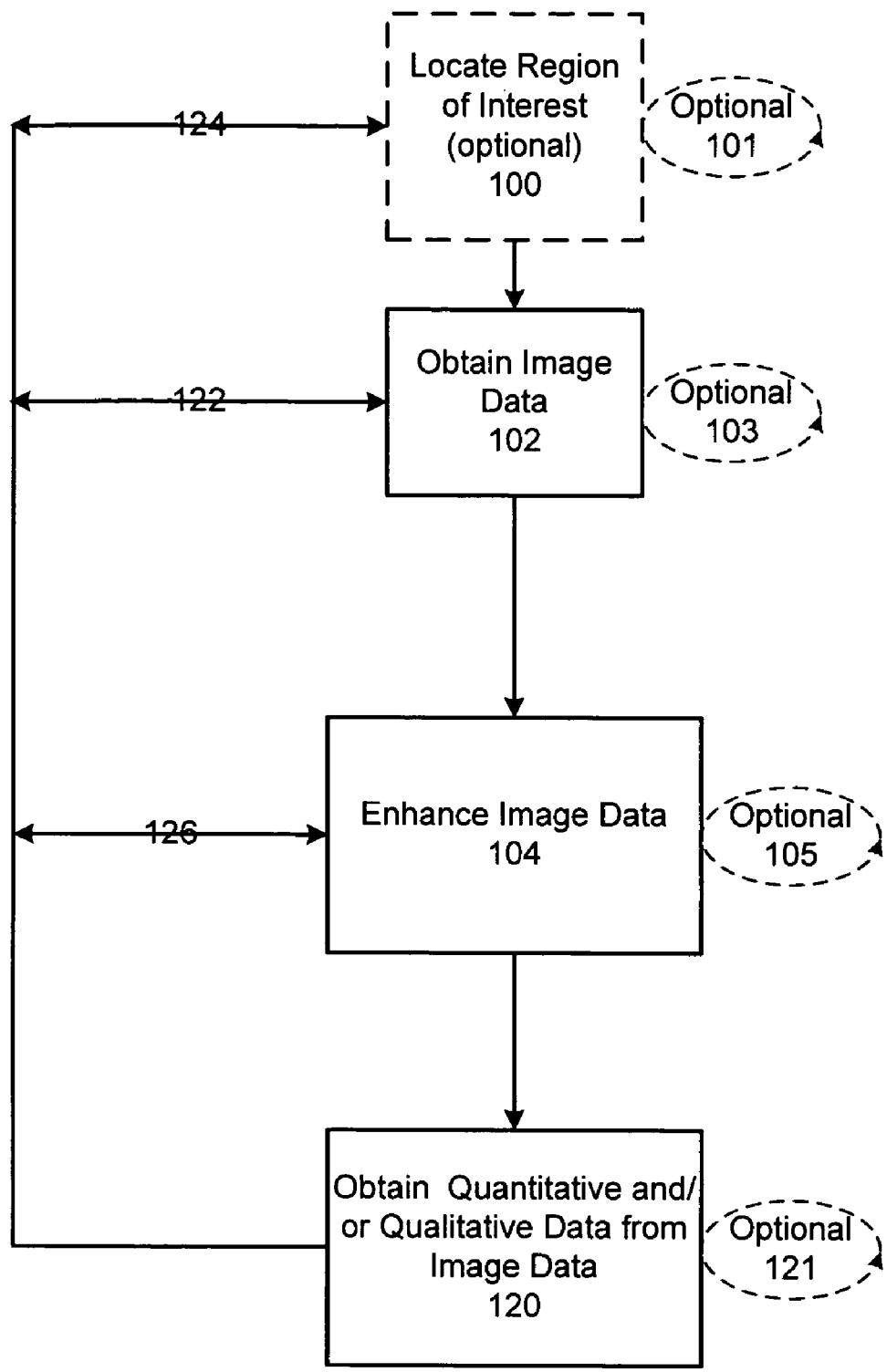

FIG. 4B illustrates the process shown in FIG. 4A with the additional step enhancing image data 104. Additionally, the step of enhancing image data 104 can be repeated one or more times 105, as desired. The process of enhancing image data 104 can be repeated 126 one or more times as desired.

Figure 5A:
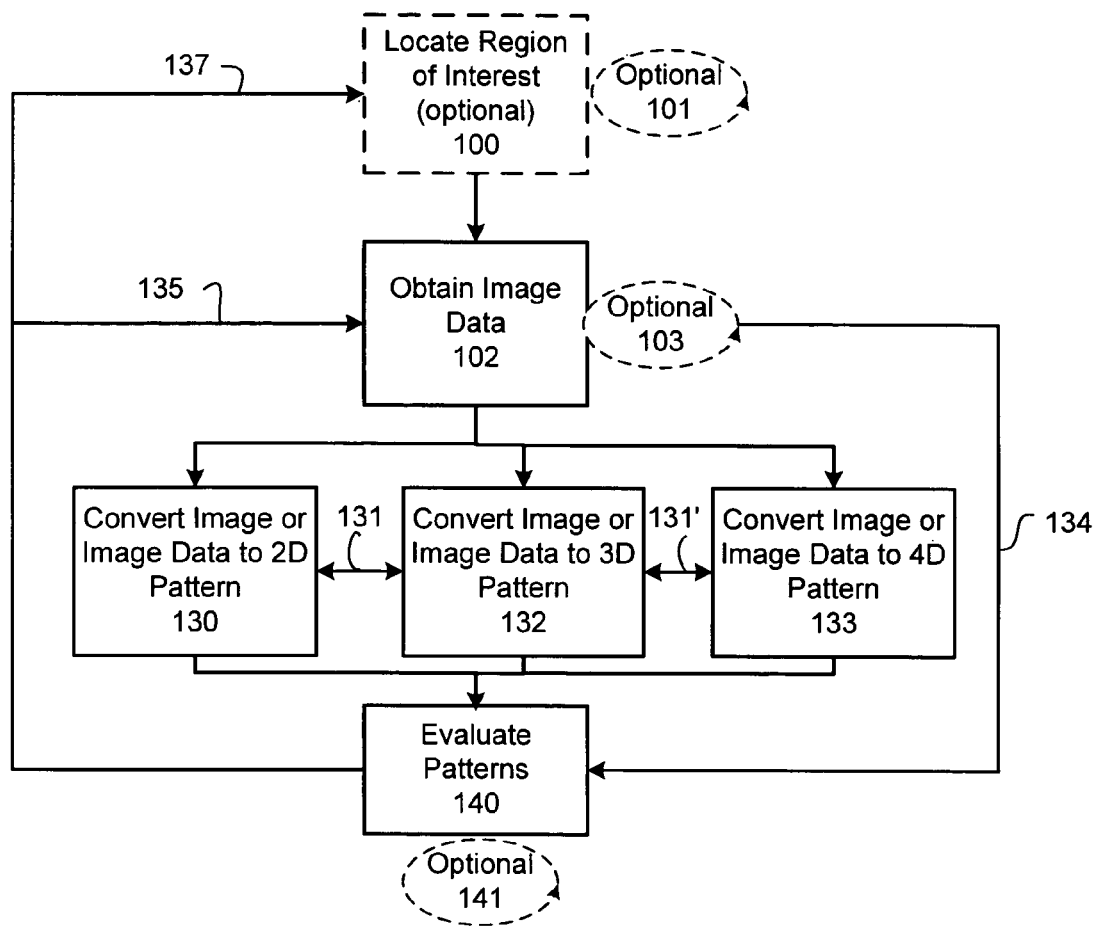
FIGS. 5A-E are block diagrams illustrating steps involved in evaluating patterns in an image of a region of interest.

Turning now to FIG. 5A, a process is shown whereby a region of interest is optionally located 100. Although not depicted here, as discussed above with respect to FIG. 1A, the step of locating a part of the body for study 98 can be performed prior to locating a region of interest 100 without departing from the invention. Additionally that step can be repeated 99. Once the region of interest is located 100, and image data is extracted from the ROI 102, the extracted image data can then be converted to a 2D pattern 130, a 3D pattern 132 or a 4D pattern 133, for example including velocity or time, to facilitate data analyses. Following conversion to 2D 130, 3D 132 or 4D pattern 133 the images are evaluated for patterns 140. Additionally images can be converted from 2D to 3D 131, or from 3D to 4D 131', if desired. Although not illustrated to avoid obscuring the figure, persons of skill in the art will appreciate that similar conversions can occur between 2D and 4D in this process or any process illustrated in this invention.

As will be appreciated by those of skill in the art, the conversion step is optional and the process can proceed directly from extracting image data from the ROI 102 to evaluating the data pattern 140 directly 134. Evaluating the data for patterns, includes, for example, performing the measurements described in Table 1, Table 2 or Table 3, above.

Additionally, the steps of locating the region of interest 100, obtaining image data 102, and evaluating patterns 141 can be performed once or a plurality of times, 101, 103, 141, respectively at any stage of the process. As will be appreciated by those of skill in the art, the steps can be repeated. For example, following an evaluation of patterns 140, additional image data can be obtained 135, or another region of interest can be located 137. These steps can be repeated as often as desired, in any combination desirable to achieve the data analysis desired.

Figure 5B:
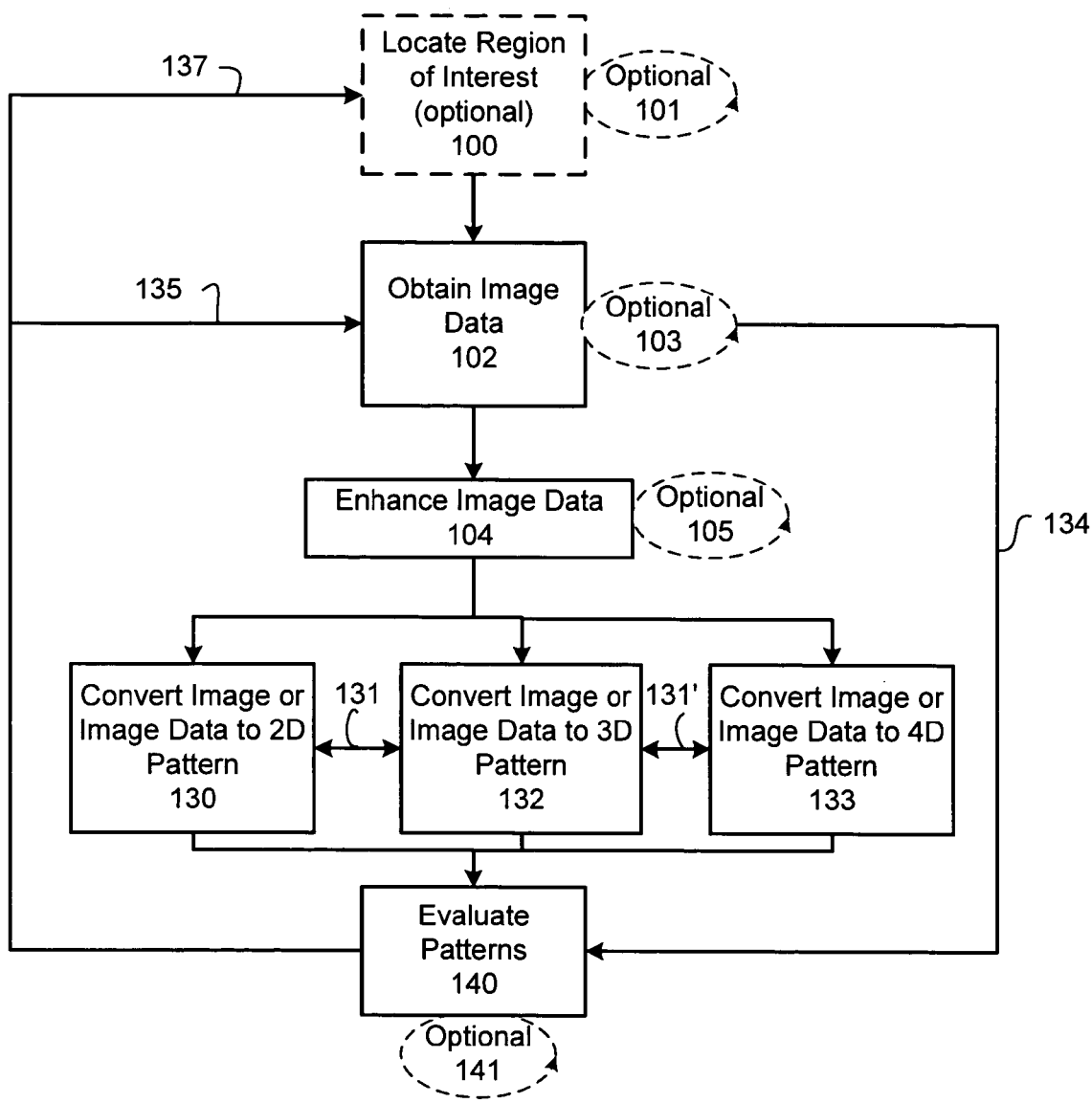
Figure 5C:
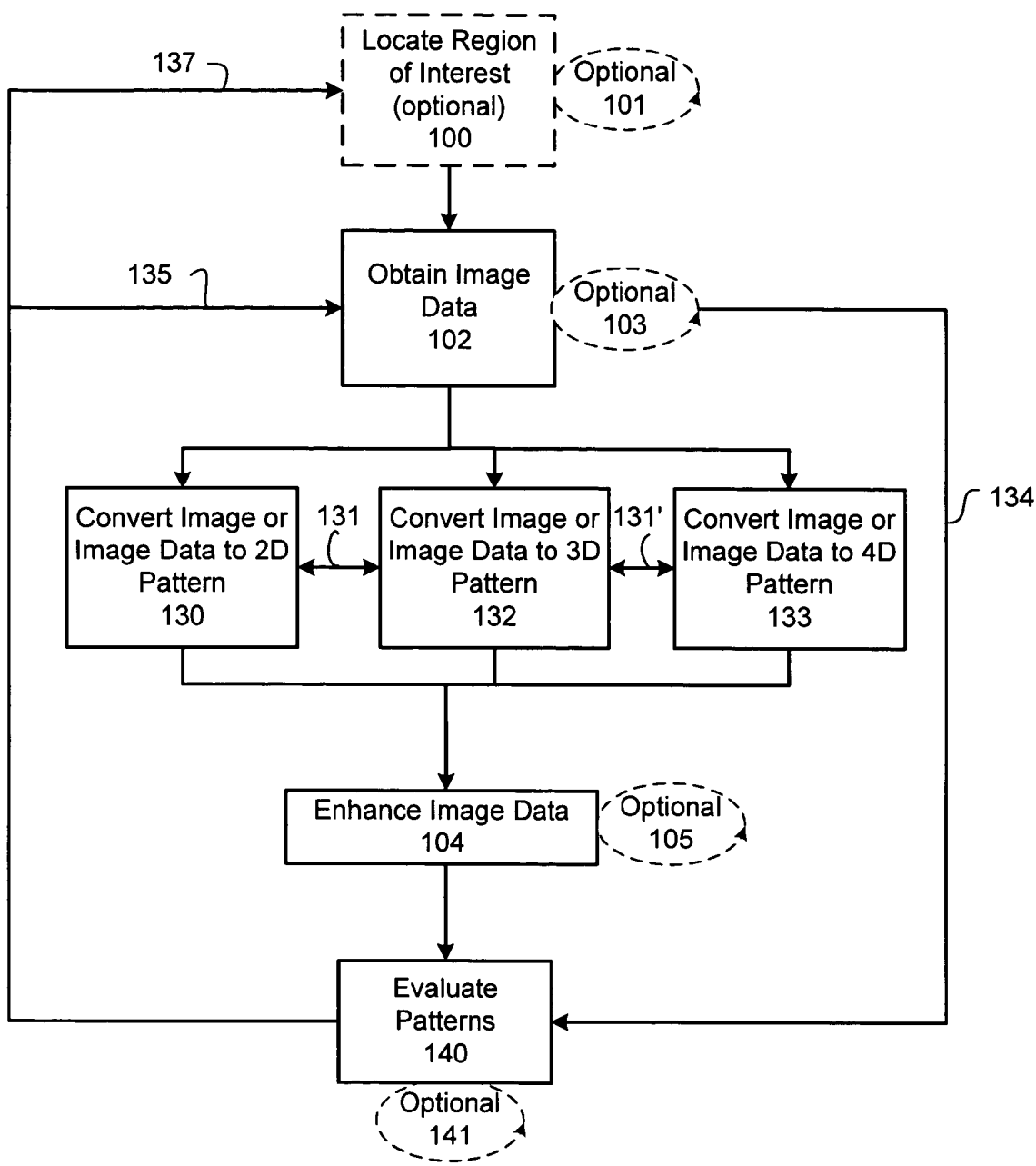

FIG. 5B illustrates an alternative process to that shown in FIG. 5A which5A THAT includes the step of enhancing image data 104 prior to converting an image or image data to a 2D 130, 3D 132, or 4D 133 pattern. The process of enhancing image data 104, can be repeated 105 if desired. FIG. 5C illustrates an alternative embodiment to the process shown in FIG. 5B. In this process, the step of enhancing image data 104 occurs after converting an image or image data to a 2D 130, 3D 132, or 4D 133 pattern. Again, the process of enhancing image data 104, can be repeated 105 if desired.

Figure 5D:
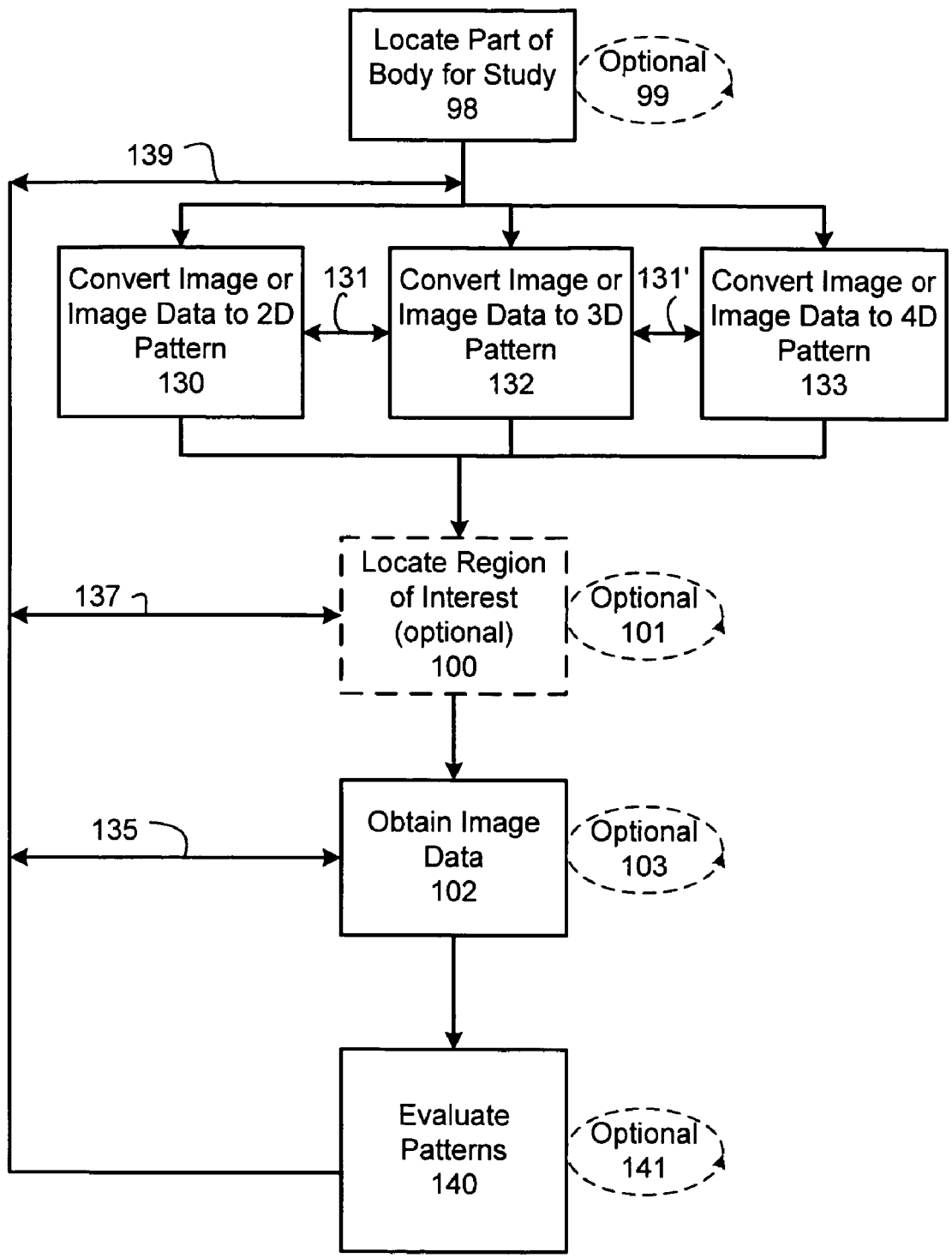

FIG. 5D illustrates an alternative process to that shown in FIG. 5A. After locating a part of the body for study 98 and imaging, the image is then converted to a 2D pattern 130, 3D pattern 132 or 4D pattern 133. The region of interest 100 is optionally located within the image after conversion to a 2D, 3D or 4D image and data is then extracted 102. Patterns are then evaluated in the extracted image data 140. As with the process of FIG. 5A, the conversion step is optional. Further, if desired, images can be converted between 2D, 3D 131 and 4D 131' if desired.

Similar to FIG. 5A, some or all the processes can be repeated one or more times as desired. For example, locating a part of the body for study 98, locating a region of interest 100, obtaining image data 102, and evaluating patterns 140, can be repeated one or more times if desired, 99, 101, 103, 141, respectively. Again steps can be repeated. For example, following an evaluation of patterns 140, additional image data can be obtained 135, or another region of interest can be located 137 and/or another portion of the body can be located for study 139. These steps can be repeated as often as desired, in any combination desirable to achieve the data analysis desired.

Figure 5E:
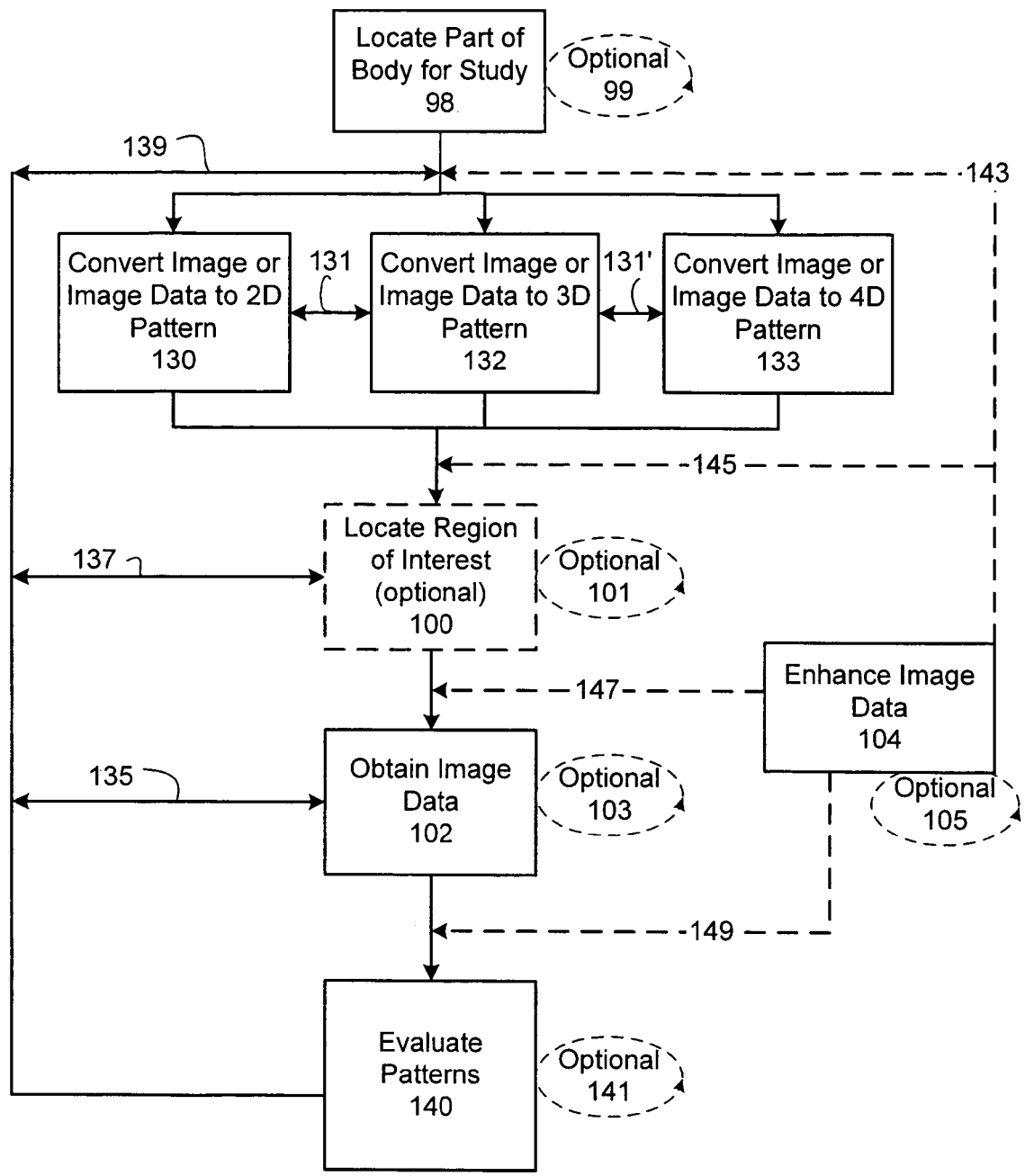

FIG. 5E illustrates an alternative process to that shown in FIG. 5D. In this process image data can be enhanced 104. The step of enhancing image data can occur prior to conversion 143, prior to locating a region of interest 145, prior to obtaining image data 102, or prior to evaluating patterns 149.

Similar to FIG. 5A, some or all the processes can be repeated one or more times as desired, including the process of enhancing image data 104, which is shown as 105.

The method also comprises obtaining an image of a bone or a joint, optionally converting the image to a two-dimensional or three-dimensional or four-dimensional pattern, and evaluating the amount or the degree of normal, diseased or abnormal tissue or the degree of degeneration in a region or a volume of interest using one or more of the parameters specified in Table 1, Table 2 and/or Table 3. By performing this method at an initial time $T_1$, information can be derived that is useful for diagnosing one or more conditions or for staging, or determining, the severity of a condition. This information can also be useful for determining the prognosis of a patient, for example with osteoporosis or arthritis. By performing this method at an initial time $T_1$, and a later time $T_2$, the change, for example in a region or volume of interest, can be determined which then facilitates the evaluation of appropriate steps to take for treatment. Moreover, if the subject is already receiving therapy or if therapy is initiated after time $T_1$, it is possible to monitor the efficacy of treatment. By performing the method at subsequent times, $T_2$-$T_n$. additional data ca be acquired that facilitate predicting the progression of the disease as well as the efficacy of any interventional steps that have been taken. As will be appreciated by those of skill in the art, subsequent measurements can be taken at regular time intervals or irregular time intervals, or combinations thereof. For example, it can be desirable to perform the analysis at $T_1$ with an initial follow-up, $T_2$, measurement taken one month later. The pattern of one month follow-up measurements could be performed for a year (12 one-month intervals) with subsequent follow-ups performed at 6 month intervals and then 12 month intervals. Alternatively, as an example, three initial measurements could be at one month, followed by a single six month follow up which is then followed again by one or more one month follow-ups prior to commencing 12 month follow ups. The combinations of regular and irregular intervals are endless, and are not discussed further to avoid obscuring the invention.

Moreover, one or more of the parameters listed in Tables 1, 2 and 3 can be measured. The measurements can be analyzed separately or the data can be combined, for example using statistical methods such as linear regression modeling or correlation. Actual and predicted measurements can be compared and correlated. See, also, Example 1.

The method for assessing the condition of a bone or joint in a subject can be fully automated such that the measurements of one or more of the parameters specified in Table 1, Table 2 or Table 3 are done automatically without intervention. The automatic assessment then can include the steps of diagnosis, staging, prognostication or monitoring the disease or diseases, or to monitor therapy. As will be appreciated by those of skill in the art, the fully automated measurement is, for example, possible with image processing techniques such as segmentation and registration. This process can include, for example, seed growing, thresholding, atlas and model based segmentation methods, live wire approaches, active and/or deformable contour approaches, contour tracking, texture based segmentation methods, rigid and non-rigid surface or volume registration, for example based on mutual information or other similarity measures. One skilled in the art will readily recognize other techniques and methods for fully automated assessment of the parameters and measurements specified in Table 1, Table 2 and Table 3.

Alternatively, the method of assessing the condition of a bone or joint in a subject can be semi-automated such that the measurements of one or more of the parameters, such as those specified in Table 1, are performed semi-automatically, i.e., with intervention. The semi-automatic assessment then allows for human interaction and, for example, quality control, and utilizing the measurement of said parameter(s) to diagnose, stage, prognosticate or monitor a disease or to monitor a therapy. The semi-automated measurement is, for example, possible with image processing techniques such as segmentation and registration. This can include seed growing, thresholding, atlas and model based segmentation methods, live wire approaches, active and/or deformable contour approaches, contour tracking, texture based segmentation methods, rigid and non-rigid surface or volume registration, for example base on mutual information or other similarity measures. One skilled in the art will readily recognize other techniques and methods for semi-automated assessment of the parameters specified in Table 1, Table 2 or Table 3.

Figure 6A:
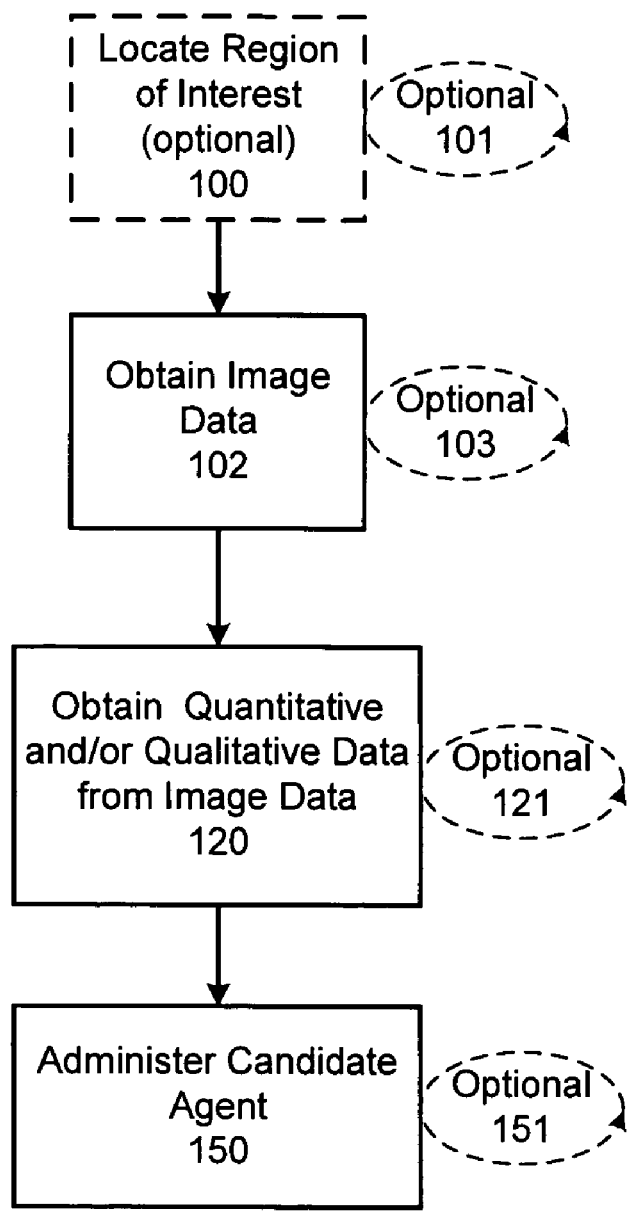
FIG. 6A-E are block diagrams illustrating steps involved in deriving quantitative and qualitative data from an image in conjunction with administering candidate molecules or drugs for evaluation.

Turning now to FIG. 6A, a process is shown whereby the user locates a ROI 100, extracts image data from the ROI 102, and then derives quantitative and/or qualitative image data from the extracted image data 120, as shown above with respect to FIG. 1. Following the step of deriving quantitative and/or qualitative image data, a candidate agent is administered to the patient 150. The candidate agent can be any agent the effects of which are to be studied. Agents can include any substance administered or ingested by a subject, for example, molecules, pharmaceuticals, biopharmaceuticals, agropharmaceuticals, or combinations thereof, including cocktails, that are thought to affect the quantitative and/or qualitative parameters that can be measured in a region of interest. These agents are not limited to those intended to treat disease that affects the musculoskeletal system but this invention is intended to embrace any and all agents regardless of the intended treatment site. Thus, appropriate agents are any agents whereby an effect can be detected via imaging. The steps of locating a region of interest 100, obtaining image data 102, obtaining quantitative and/or qualitative data from image data 120, and administering a candidate agent 150, can be repeated one or more times as desired, 101, 103, 121, 151, respectively.

Figure 6B:
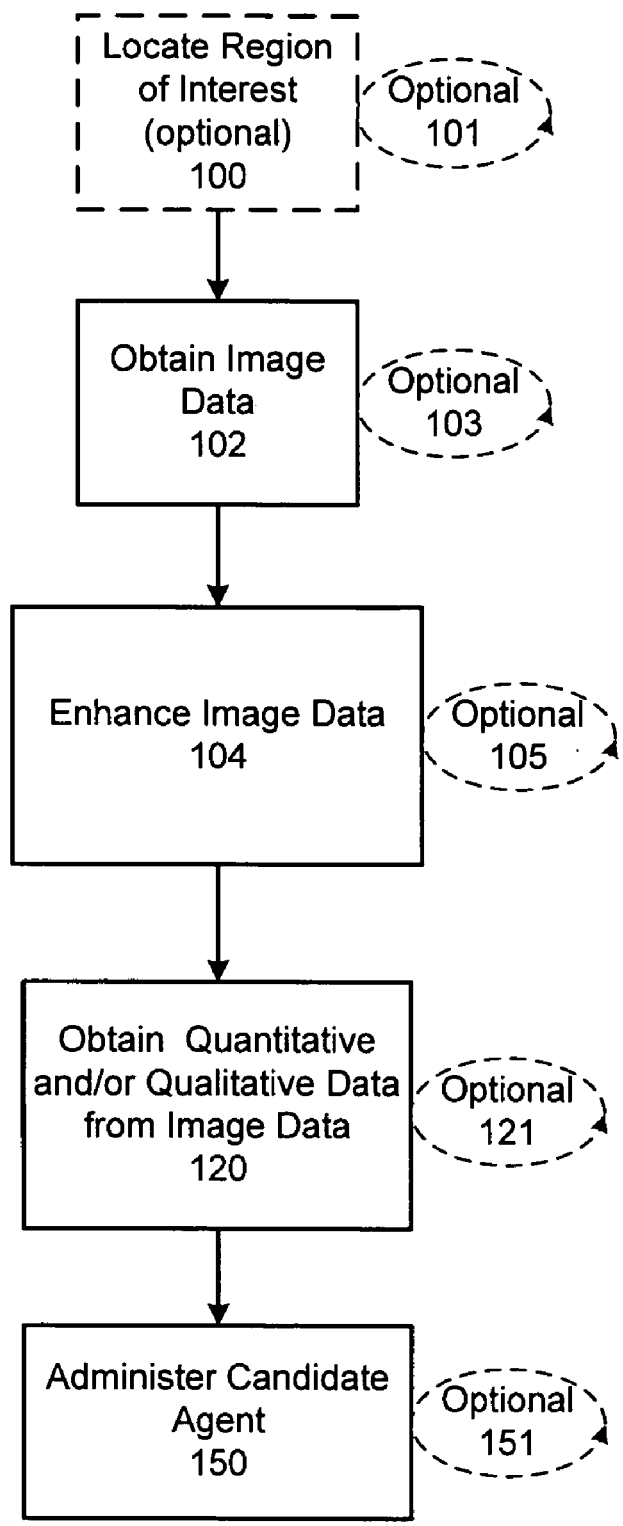

FIG. 6B shows the additional step of enhancing image data 104, which can also be optionally repeated 105 as often as desired.

Figure 6C:
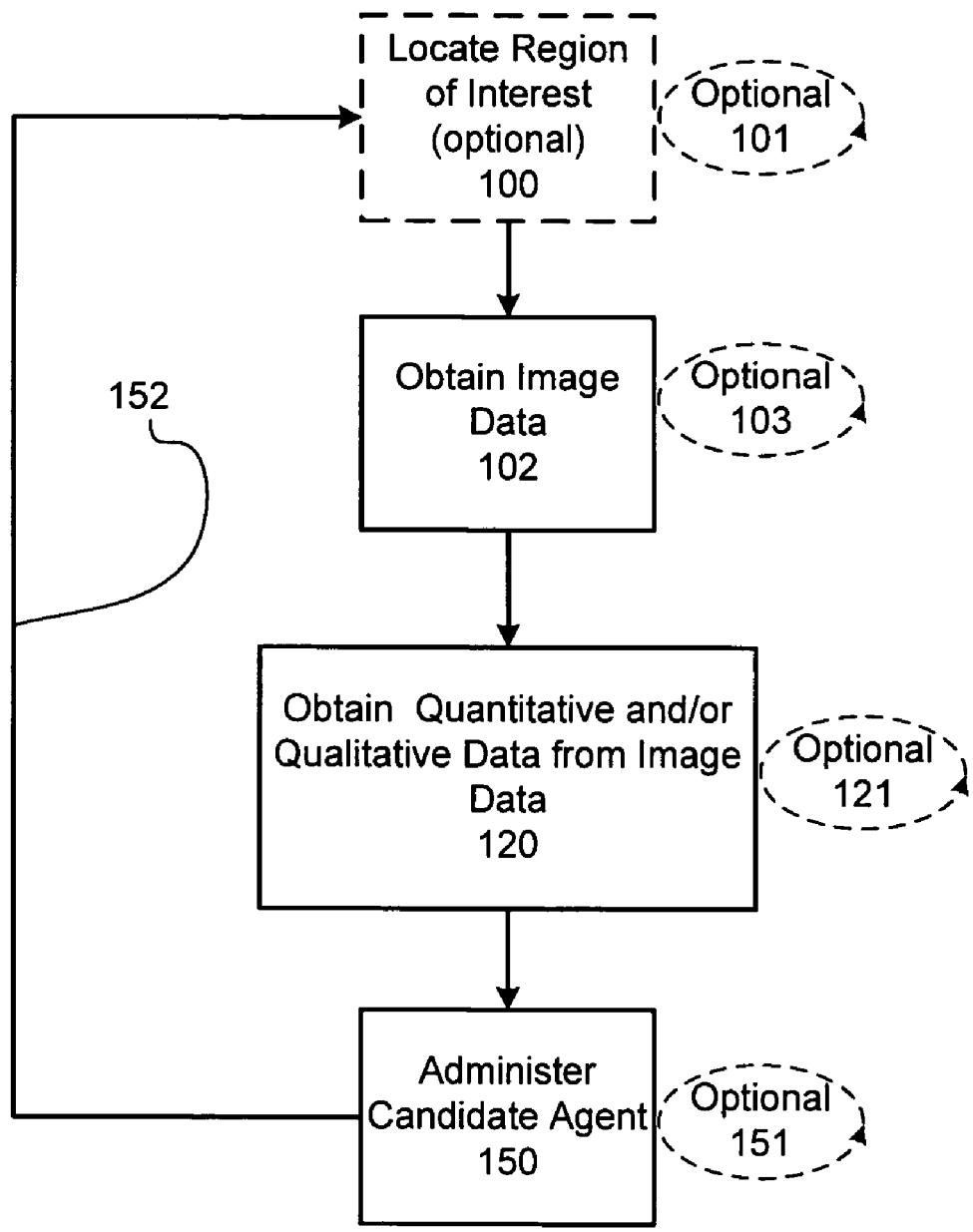
Figure 6D:
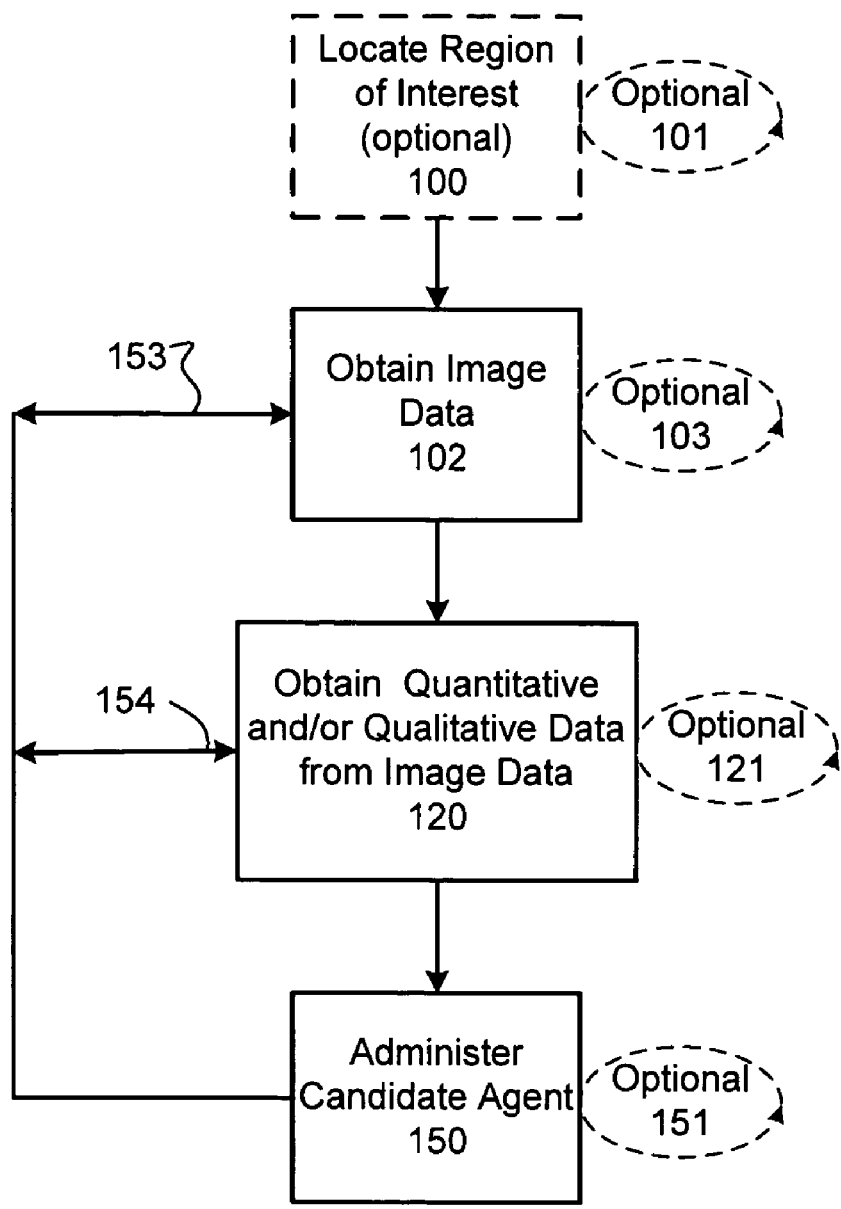

As shown in FIG. 6C these steps can be repeated one or more times 152 to determine the effect of the candidate agent. As will be appreciated by those of skill in the art, the step of repeating can occur at the stage of locating a region of interest 152 as shown in FIG. 6B or it can occur at the stage obtaining image data 153 or obtaining quantitative and/or qualitative data from image data 154 as shown in FIG. 6D.

Figure 6E:
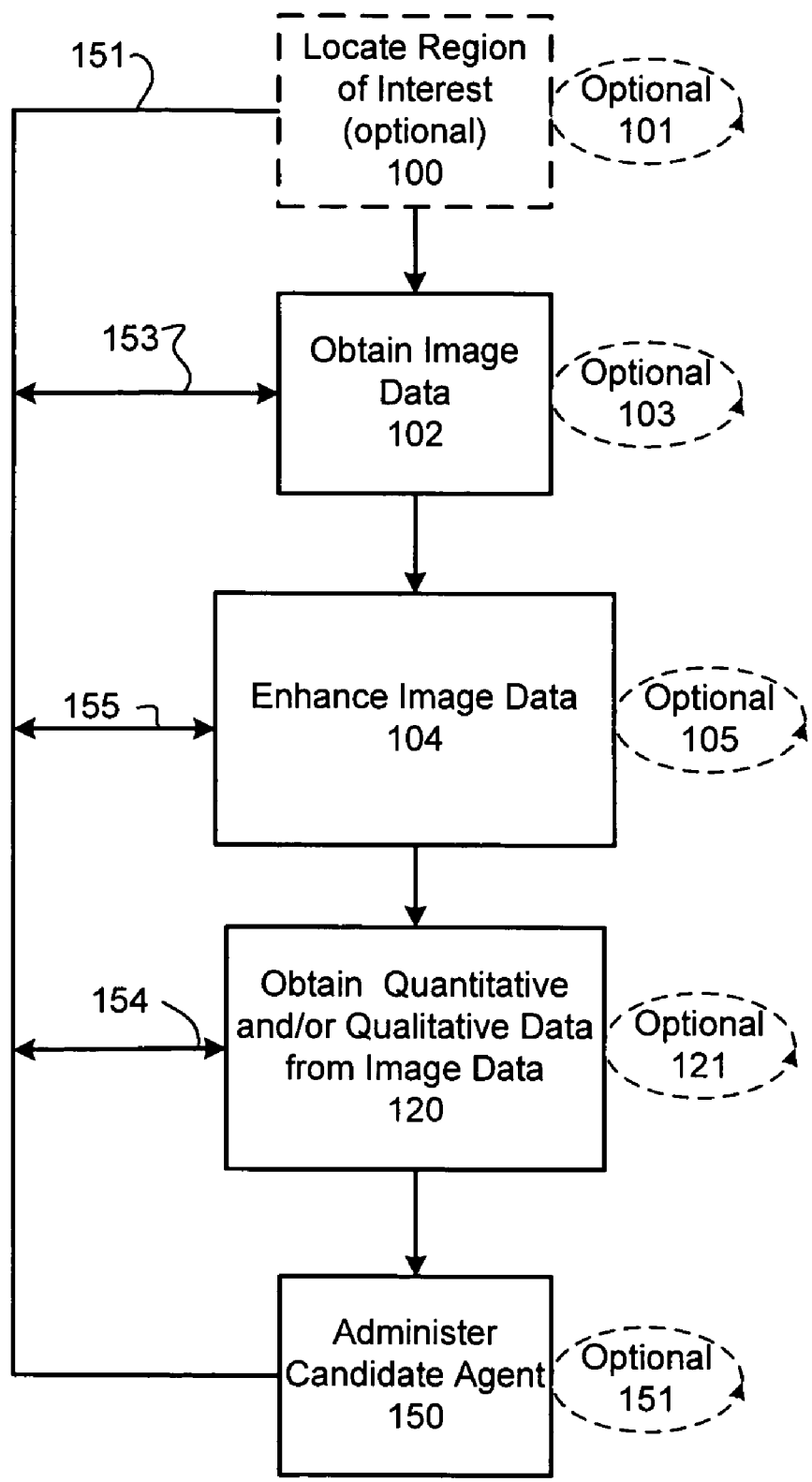

FIG. 6E shows the additional step of enhancing image data 104, which can optionally be repeated 105, as desired.

As previously described, some or all the processes shown in FIGS. 6A-E can be repeated one or more times as desired. For example, locating a region of interest 100, obtaining image data 102, enhancing image data 104, obtaining quantitative and/or qualitative data 120, evaluating patterns 140, and administering candidate agent 150 can be repeated one or more times if desired, 101, 103, 105, 121, 141, 151 respectively.

In the scenario described in relation to FIGS. 6, an image is taken prior to administering the candidate agent. However, as will be appreciated by those of skill in the art, it is not always possible to have an image prior to administering the candidate agent. In those situations, progress is determined over time by evaluating the change in parameters from extracted image to extracted image.

Figure 7A:
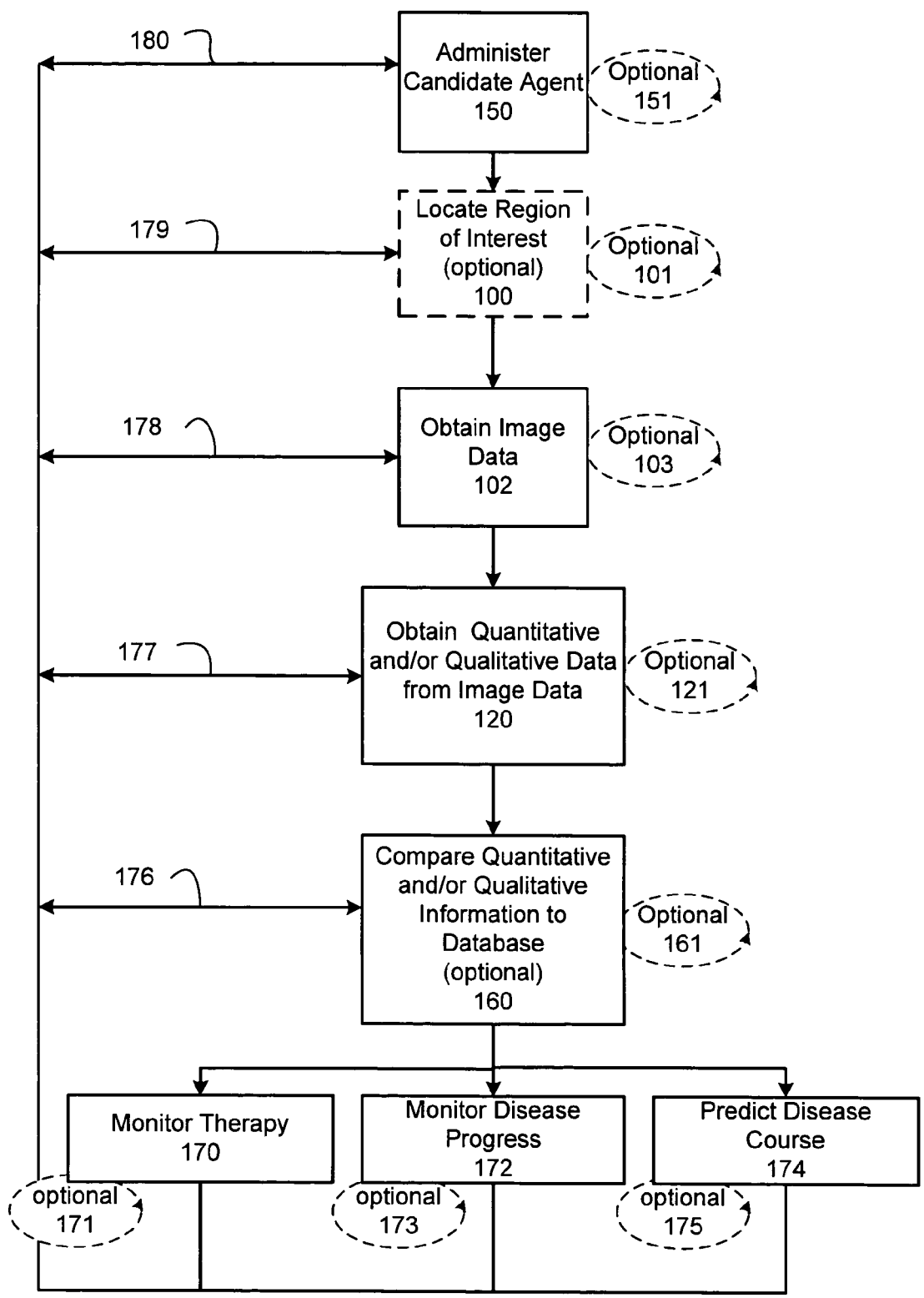
FIGS. 7A-D are block diagrams illustrating steps involved in comparing derived quantitative and qualitative information to a database or to information obtained at a previous time.
Figure 7B:
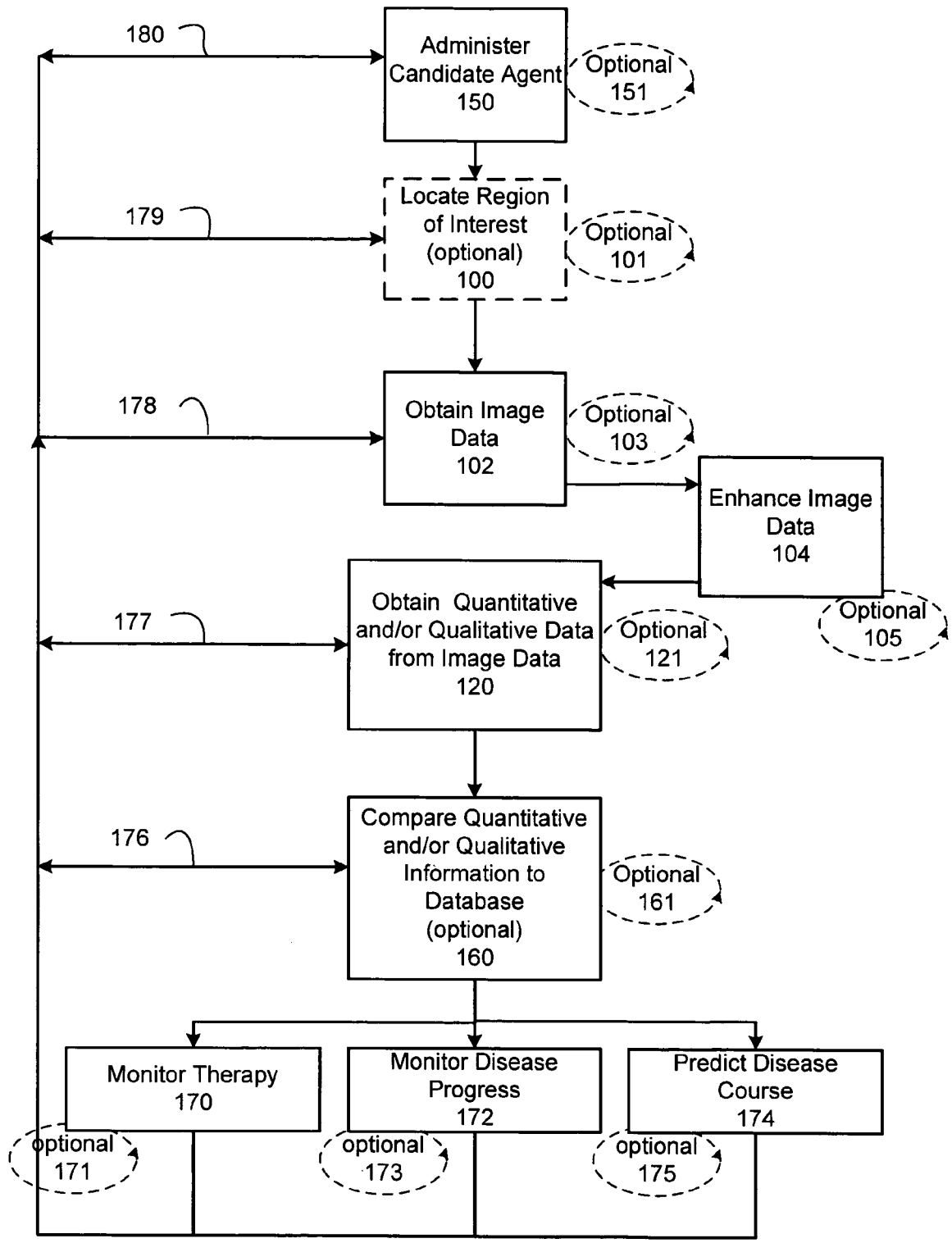

Turning now to FIG. 7A, the process is shown whereby the candidate agent is administered first 150. Thereafter a region of interest is located in an image taken 100 and image data is extracted 102. Once the image data is extracted, quantitative and/or qualitative data is extracted from the image data 120. In this scenario, because the candidate agent is administered first, the derived quantitative and/or qualitative data derived is compared to a database 160 or a subset of the database, which database that, includes data for subjects having similar tracked parameters. As shown in FIG. 7B following the step of obtaining image data, the image data can be enhanced 104. This process can optionally be repeated 105, as desired.

Figure 7C:
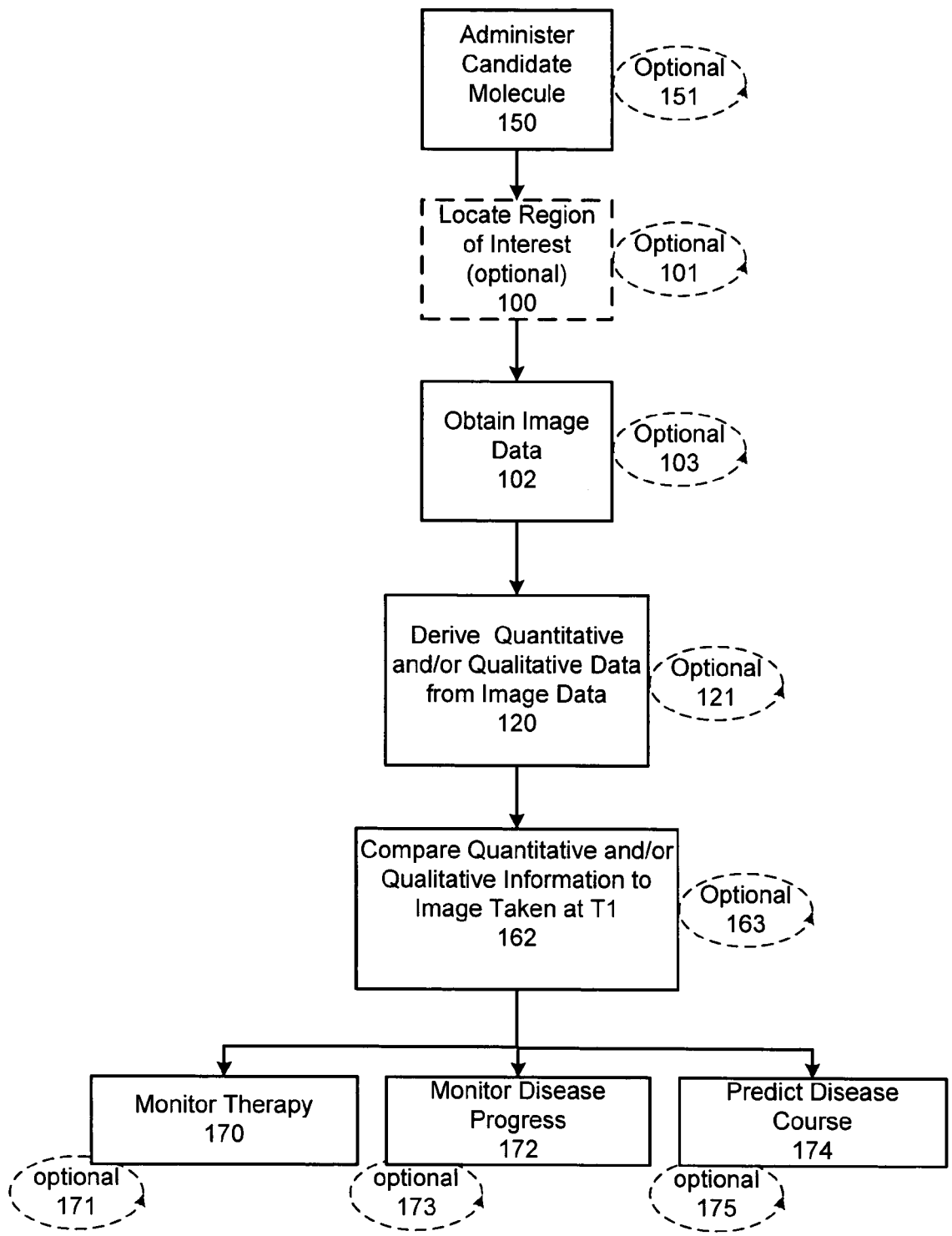
Figure 7D:
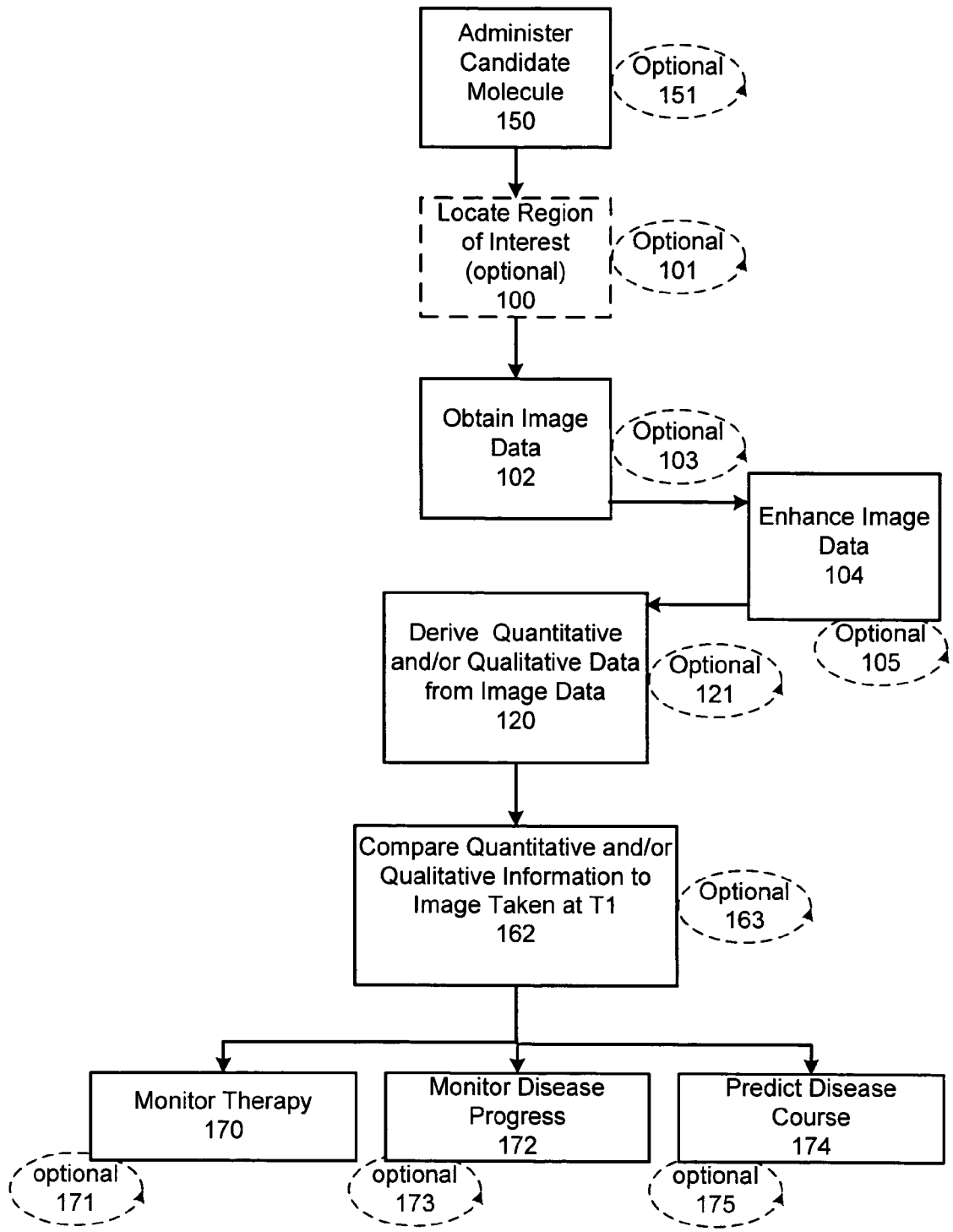

Alternatively, as shown in FIG. 7C the derived quantitative and/or qualitative information can be compared to an image taken at T1 162, or any other time, if such image is available. As shown in FIG. 7D the step of enhancing image data 104 can follow the step of obtaining image data 102. Again, the process can be repeated 105, as desired.

As previously described, some or all the processes illustrated in FIGS. 7A-D can be repeated one or more times as desired. For example, locating a region of interest 100, obtaining image data 102, enhancing image data 104, obtaining quantitative and/or qualitative data 120, administering candidate agent 150, comparing quantitative and/or qualitative information to a database 160, comparing quantitative and/or qualitative information to an image taken at a prior time, such as $T_1$, 162, monitoring therapy 170, monitoring disease progress 172, predicting disease course 174 can be repeated one or more times if desired, 101, 103, 105, 121, 151, 161, 163, 171, 173, 175 respectively. Each of these steps can be repeated in one or more loops as shown in FIG. 7B, 176, 177, 178, 179, 180, as desired or appropriate to enhance data collection.

Figure 8A:
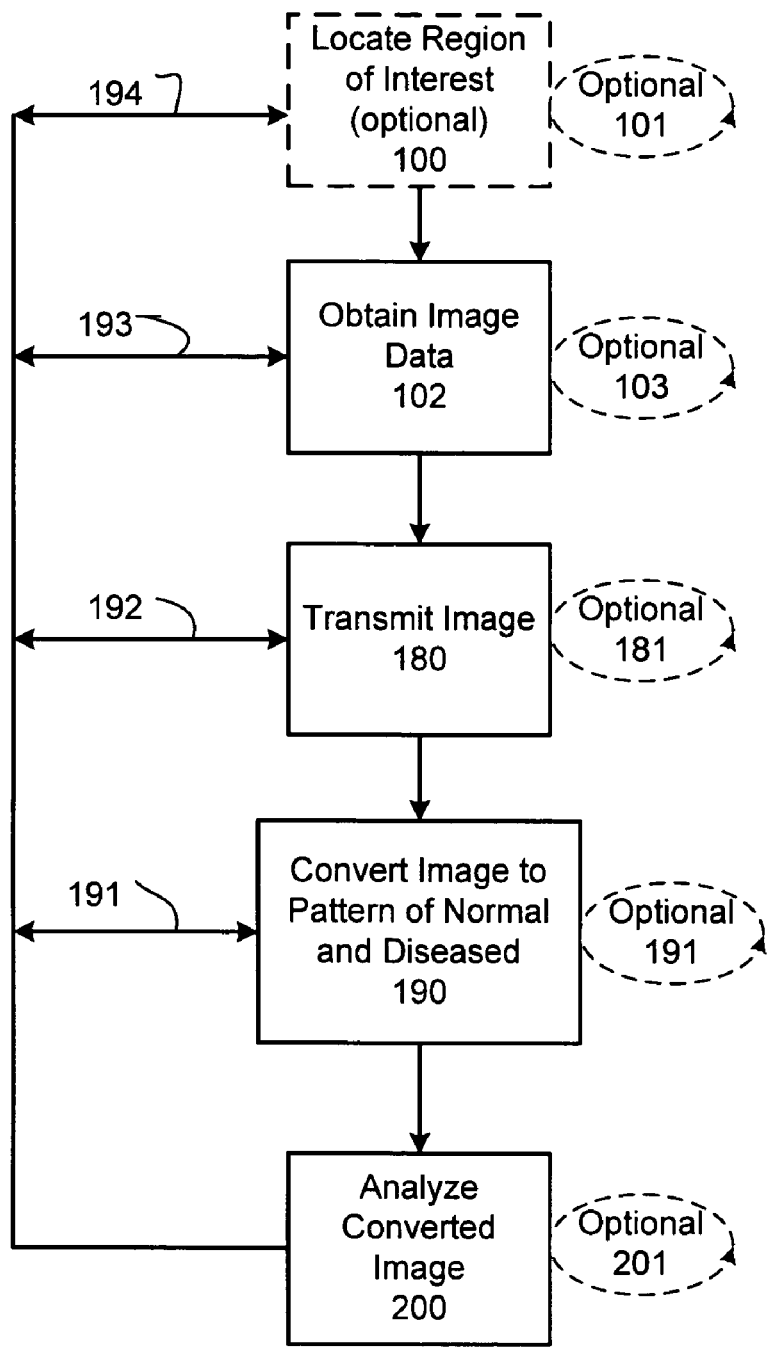
FIGS. 8A-D are block diagrams illustrating steps involved in comparing converting an image to a pattern of normal and diseased tissue
Figure 8B:
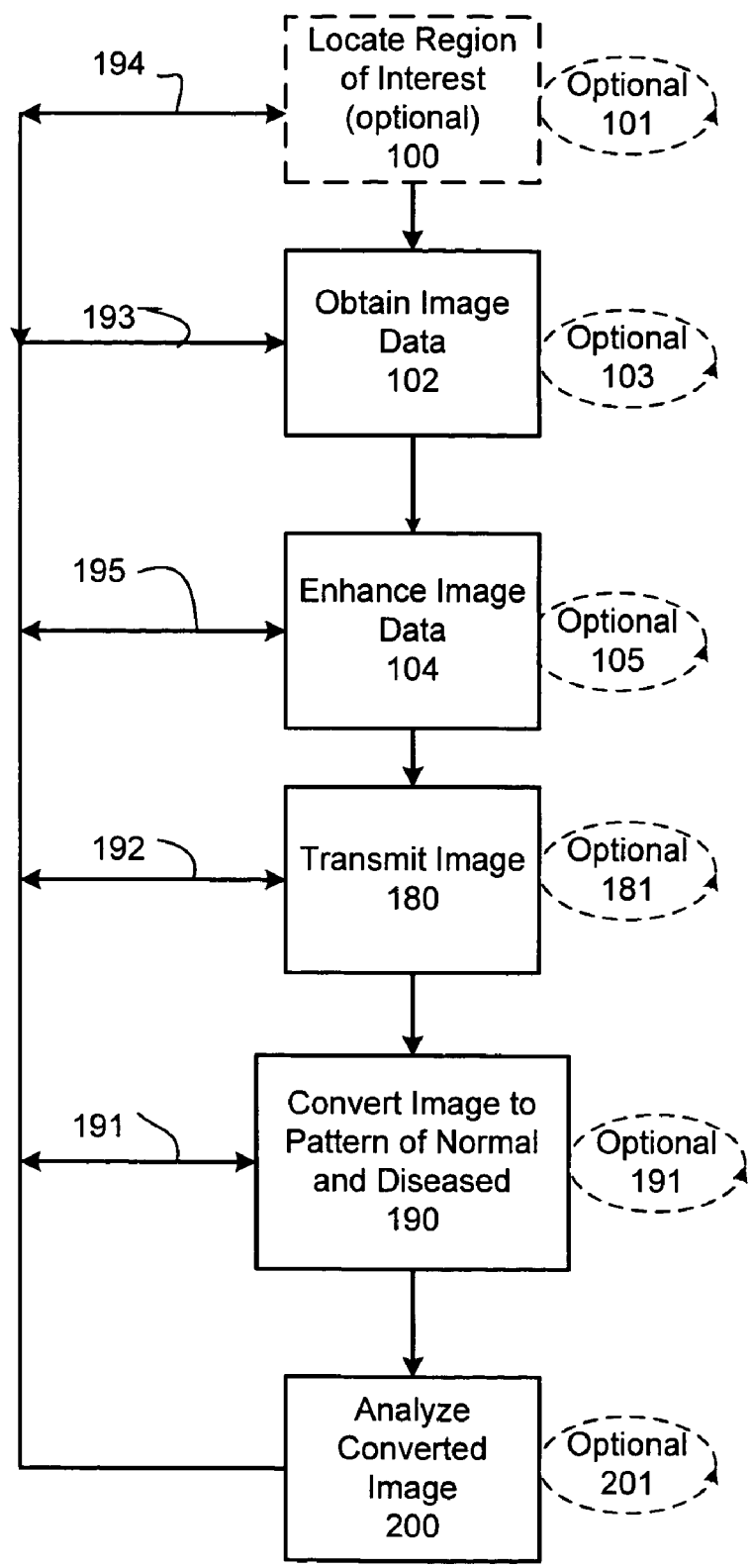

Turning now to FIG. 8A, following the step of extracting image data from the ROI 102, the image can be transmitted 180. Transmission can be to another computer in the network or via the World Wide Web to another network. Following the step of transmitting the image 180, the image is converted to a pattern of normal and diseased tissue 190. Normal tissue includes the undamaged tissue located in the body part selected for study. Diseased tissue includes damaged tissue located in the body part selected for study. Diseased tissue can also include, or refer to, a lack of normal tissue in the body part selected for study. For example, damaged or missing cartilage would be considered diseased tissue. Once the image is converted, it is analyzed 200. FIG. 8B illustrates the process shown in FIG. 8A with the additional step of enhancing image data 104. As will be appreciated by those of skill in the art, this process can be repeated 105 as desired.

Figure 8C:
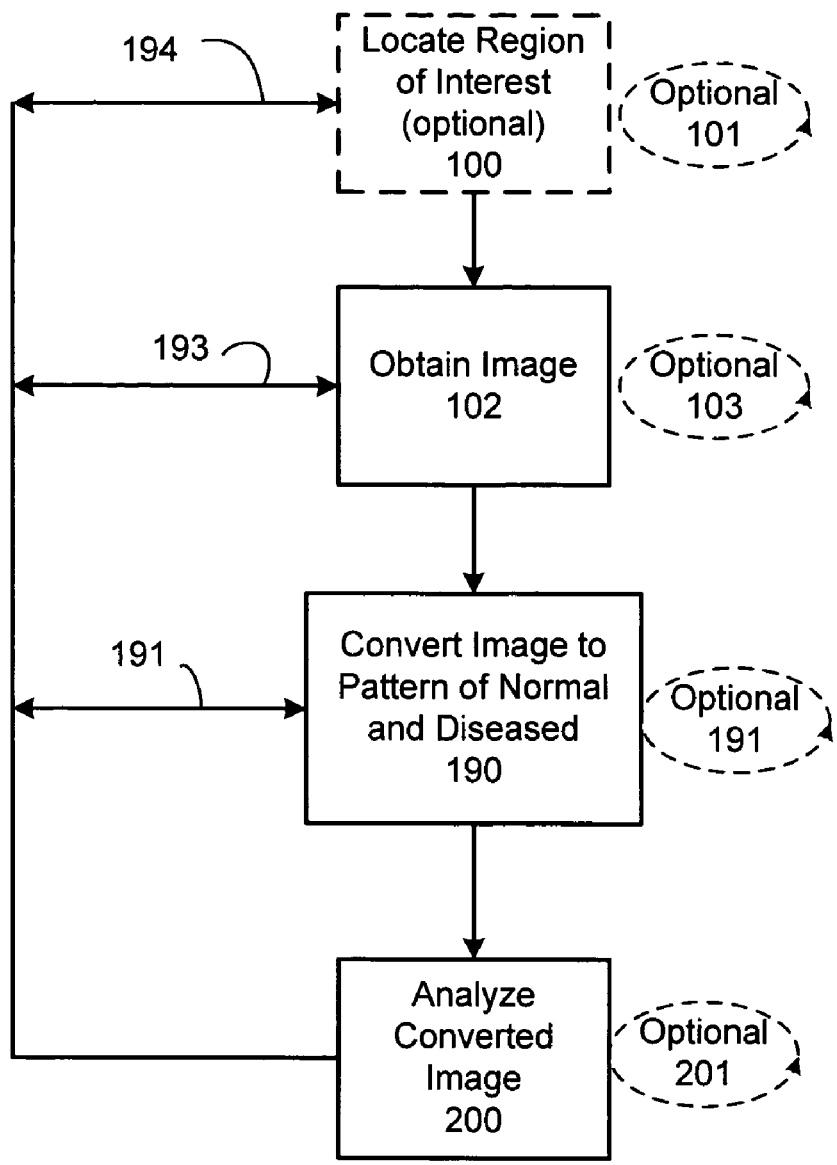
Figure 8D:
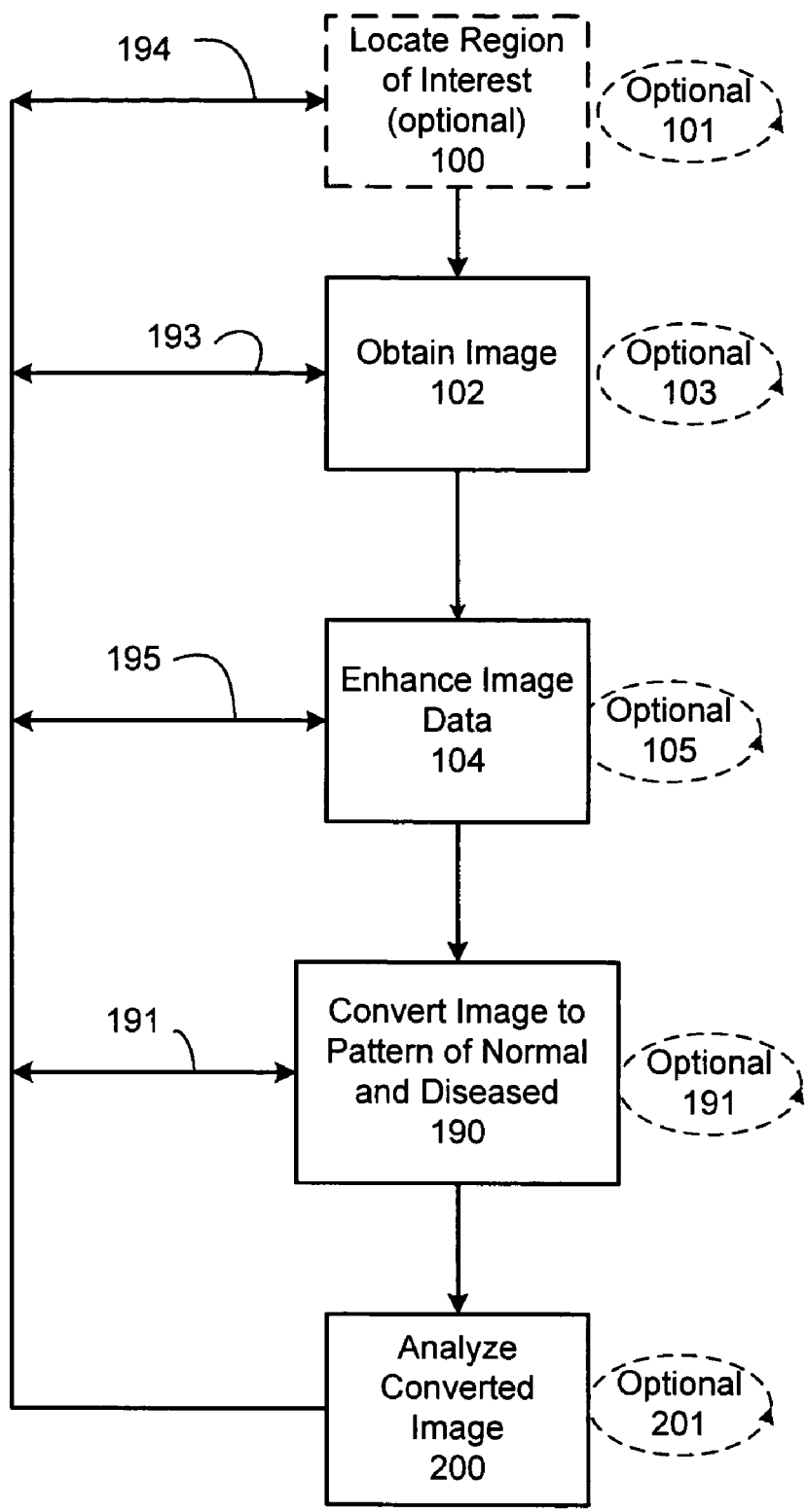

As shown in FIG. 8C, the step of transmitting the image 180 illustrated in FIG. 8A is optional and need not be practiced under the invention. As will be appreciated by those of skill in the art, the image can also be analyzed prior to converting the image to a pattern of normal and diseased. FIG. 8D illustrates the process shown in FIG. 8C with the additional step of enhancing image data 104 that is optionally repeated 105, as desired.

As previously described, some or all the processes in FIGS. 8A-D can be repeated one or more times as desired. For example, locating a region of interest 100, obtaining image data 102, enhancing image data 104, transmitting an image 180, converting the image to a pattern of normal and diseased 190, analyzing the converted image 200, can be repeated one or more times if desired, 101, 103, 105, 181, 191, 201 respectively.

Figure 9:
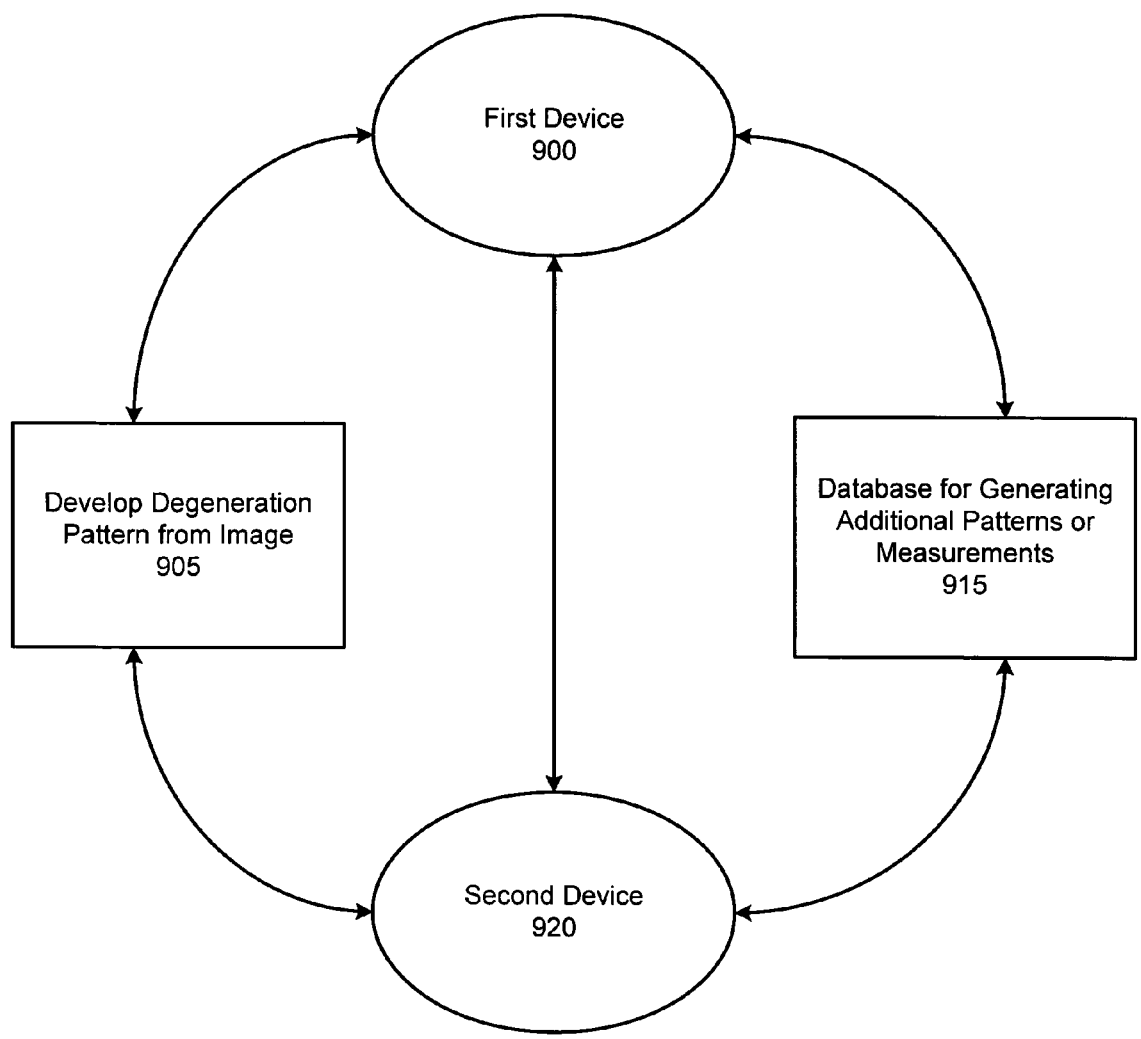
FIG. 9 is a diagram showing the use one or more devices in the process of developing a degeneration pattern and using a database for degeneration patterns.

FIG. 9 shows two devices 900, 920 that are connected. Either the first or second device can develop a degeneration pattern from an image of a region of interest 905. Similarly, either device can house a database for generating additional patterns or measurements 915. The first and second devices can communicate with each other in the process of analyzing an image, developing a degeneration pattern from a region of interest in the image, and creating a dataset of patterns or measurements or comparing the degeneration pattern to a database of patterns or measurements. However, all processes can be performed on one or more devices, as desired or necessary.

In this method the electronically generated, or digitized image or portions of the image can be electronically transferred from a transferring device to a receiving device located distant from the transferring device; receiving the transferred image at the distant location; converting the transferred image to a pattern of normal or diseased or abnormal tissue using one or more of the parameters specified in Table 1, Table 2 or Table 3; and optionally transmitting the pattern to a site for analysis. As will be appreciated by those of skill in the art, the transferring device and receiving device can be located within the same room or the same building. The devices can be on a peer-to-peer network, or an intranet. Alternatively, the devices can be separated by large distances and the information can be transferred by any suitable means of data transfer, including the World Wide Web and ftp protocols.

Alternatively, the method can comprise electronically transferring an electronically-generated image or portions of an image of a bone or a joint from a transferring device to a receiving device located distant from the transferring device; receiving the transferred image at the distant location; converting the transferred image to a degeneration pattern or a pattern of normal or diseased or abnormal tissue using one or more of the parameters specified in Table 1, Table 2 or Table 3; and optionally transmitting the degeneration pattern or the pattern of normal or diseased or abnormal tissue to a site for analysis.

Thus, the invention described herein includes methods and systems for prognosis of musculoskeletal disease, for example prognosis of fracture risk and the like. (See, also, Example 1). FIG. 10 is a schematic depiction of an image of a femur showing various ROIs that were analyzed to predict fracture risk based on assessment of one or more parameters shown in Tables 1, 2 and 3.

In order to make more accurate prognoses, it may be desirable in certain instances to compare data obtained from a subject to a reference database. For example, when predicting fracture risk, it may be useful to compile data of actual (known) fracture load in a variety of samples and store the results based on clinical risk factors such as age, sex and weight (or other characteristics) of the subject from which the sample is obtained. The images of these samples are analyzed to obtain parameters shown in Tables 1, 2 and 3. A fracture risk model correlated with fracture load may be developed using univariate, bivariate and/or multivariate statistical analysis of these parameters and is stored in this database. A fracture risk model may include information that is used to estimate fracture risk from parameters shown in Tables 1, 2 and 3. An example of a fracture risk model is the coefficients of a multivariate linear model derived from multivariate linear regression of these parameters (Tables 1,2,3, age, sex, weight, etc.) with fracture load. A person skilled in the art will appreciate that fracture risk models can be derived using other methods such as artificial neural networks and be represented by other forms such as the coefficients of artificial neural networks. Patient fracture risk can then be determined from measurements obtain from bone images by referencing to this database.

Methods of determining actual fracture load are known to those in the field. FIG. 11 is a schematic depiction of biomechanical testing of an intact femur. As shown, cross-sectional images may be taken throughout testing to determine at what load force a fracture occurs. FIG. 12B is a reproduction of an x-ray image depicting an example of an induced fracture in a fresh cadaveric femur.

The analysis techniques described herein can then be applied to a subject and the risk of fracture (or other disease) predicted using one or more of the parameters described herein. As shown in FIGS. 13 to 16, the prognostication methods described herein are as (or more) accurate than known techniques in predicting fracture risk. FIG. 13 is a graph depicting linear regression analysis of DXA bone mineral density correlated to fracture load. Correlations of individual parameters to fracture load are comparable to DXA (FIG. 14 and 15). However, when multiple structural parameters are combined, the prediction of load at which fracture will occur is more accurate. (FIG. 16). Thus, the analyses of images as described herein can be used to accurately predict musculoskeletal disease such as fracture risk.

Another aspect of the invention is a kit for aiding in assessing the condition of a bone or a joint of a subject, which kit comprises a software program, which when installed and executed on a computer reads a degeneration pattern or a pattern of normal or diseased or abnormal tissue derived using one or more of the parameters specified in Table 1, Table 2 or Table 3 presented in a standard graphics format and produces a computer readout. The kit can further include a database of measurements for use in calibrating or diagnosing the subject. One or more databases can be provided to enable the user to compare the results achieved for a specific subject against, for example, a wide variety of subjects, or a small subset of subjects having characteristics similar to the subject being studied.

A system is provided that includes (a) a device for electronically transferring a degeneration pattern or a pattern of normal, diseased or abnormal tissue for the bone or the joint to a receiving device located distant from the transferring device; (b) a device for receiving said pattern at the remote location; (c) a database accessible at the remote location for generating additional patterns or measurements for the bone or the joint of the human wherein the database includes a collection of subject patterns or data, for example of human bones or joints, which patterns or data are organized and can be accessed by reference to characteristics such as type of joint, gender, age, height, weight, bone size, type of movement, and distance of movement; (d) optionally a device for transmitting the correlated pattern back to the source of the degeneration pattern or pattern of normal, diseased or abnormal tissue.

Thus, the methods and systems described herein make use of collections of data sets of measurement values, for example measurements of bone structure and/or bone mineral density from images (e.g., x-ray images). Records can be formulated in spreadsheet-like format, for example including data attributes such as date of image (x-ray), patient age, sex, weight, current medications, geographic location, etc. The database formulations can further comprise the calculation of derived or calculated data points from one or more acquired data points, typically using the parameters listed in Tables 1, 2 and 3 or combinations thereof. A variety of derived data points can be useful in providing information about individuals or groups during subsequent database manipulation, and are therefore typically included during database formulation. Derived data points include, but are not limited to the following: (1) maximum value, e.g. bone mineral density, determined for a selected region of bone or joint or in multiple samples from the same or different subjects; (2) minimum value, e.g. bone mineral density, determined for a selected region of bone or joint or in multiple samples from the same or different subjects; (3) mean value, e.g. bone mineral density, determined for a selected region of bone or joint or in multiple samples from the same or different subjects; (4) the number of measurements that are abnormally high or low, determined by comparing a given measurement data point with a selected value; and the like. Other derived data points include, but are not limited to the following: (1) maximum value of a selected bone structure parameter, determined for a selected region of bone or in multiple samples from the same or different subjects; (2) minimum value of a selected bone structure parameter, determined for a selected region of bone or in multiple samples from the same or different subjects; (3) mean value of a selected bone structure parameter, determined for a selected region of bone or in multiple samples from the same or different subjects; (4) the number of bone structure measurements that are abnormally high or low, determined by comparing a given measurement data point with a selected value; and the like. Other derived data points will be apparent to persons of ordinary skill in the art in light of the teachings of the present specification. The amount of available data and data derived from (or arrived at through analysis of) the original data provides an unprecedented amount of information that is very relevant to management of bone-related diseases such as osteoporosis. For example, by examining subjects over time, the efficacy of medications can be assessed.

Measurements and derived data points are collected and calculated, respectively, and can be associated with one or more data attributes to form a database. The amount of available data and data derived from (or arrived at through analysis of) the original data provide provides an unprecedented amount of information that is very relevant to management of musculoskeletal-related diseases such as osteoporosis or arthritis. For example, by examining subjects over time, the efficacy of medications can be assessed.

Data attributes can be automatically input with the electronic image and can include, for example, chronological information (e.g., DATE and TIME). Other such attributes can include, but are not limited to, the type of imager used, scanning information, digitizing information and the like. Alternatively, data attributes can be input by the subject and/or operator, for example subject identifiers, i.e. characteristics associated with a particular subject. These identifiers include but are not limited to the following: (1) a subject code (e.g., a numeric or alpha-numeric sequence); (2) demographic information such as race, gender and age; (3) physical characteristics such as weight, height and body mass index (BMI); (4) selected aspects of the subject's medical history (e.g., disease states or conditions, etc.); and (5) disease-associated characteristics such as the type of bone disorder, if any; the type of medication used by the subject. In the practice of the present invention, each data point would typically be identified with the particular subject, as well as the demographic, etc. characteristic of that subject.

Other data attributes will be apparent to persons of ordinary skill in the art in light of the teachings of the present specification. (See, also, WO 02/30283, incorporated by reference in its entirety herein).

Thus, data (e.g., bone structural information or bone mineral density information or articular information) is obtained from normal control subjects using the methods described herein. These databases are typically referred to as "reference databases" and can be used to aid analysis of any given subject's image, for example, by comparing the information obtained from the subject to the reference database. Generally, the information obtained from the normal control subjects will be averaged or otherwise statistically manipulated to provide a range of "normal" measurements. Suitable statistical manipulations and/or evaluations will be apparent to those of skill in the art in view of the teachings herein. The comparison of the subject's information to the reference database can be used to determine if the subject's bone information falls outside the normal range found in the reference database or is statistically significantly different from a normal control.

Data obtained from images, as described above, can be manipulated, for example, using a variety of statistical analyses to produce useful information. Databases can be created or generated from the data collected for an individual, or for a group of individuals, over a defined period of time (e.g., days, months or years), from derived data, and from data attributes.

For example, data can be aggregated, sorted, selected, sifted, clustered and segregated by means of the attributes associated with the data points. A number of data mining software exist which can be used to perform the desired manipulations.

Relationships in various data can be directly queried and/or the data analyzed by statistical methods to evaluate the information obtained from manipulating the database.

For example, a distribution curve can be established for a selected data set, and the mean, median and mode calculated therefor. Further, data spread characteristics, e.g., variability, quartiles, and standard deviations can be calculated.

The nature of the relationship between any variables of interest can be examined by calculating correlation coefficients. Useful methods for doing so include, but are not limited to: Pearson Product Moment Correlation and Spearman Rank Correlation. Analysis of variance permits testing of differences among sample groups to determine whether a selected variable has a discernible effect on the parameter being measured.

Non-parametric tests can be used as a means of testing whether variations between empirical data and experimental expectancies are attributable to chance or to the variable or variables being examined. These include the Chi Square test, the Chi Square Goodness of Fit, the 2×2 Contingency Table, the Sign Test and the Phi Correlation Coefficient. Other tests include z-scores, T-scores or lifetime risk for arthritis, cartilage loss or osteoporotic fracture.

There are numerous tools and analyses available in standard data mining software that can be applied to the analyses of the databases that can be created according to this invention. Such tools and analysis include, but are not limited to, cluster analysis, factor analysis, decision trees, neural networks, rule induction, data driven modeling, and data visualization. Some of the more complex methods of data mining techniques are used to discover relationships that are more empirical and data-driven, as opposed to theory driven, relationships.

Statistical significance can be readily determined by those of skill in the art. The use of reference databases in the analysis of images facilitates that diagnosis, treatment and monitoring of bone conditions such as osteoporosis.

For a general discussion of statistical methods applied to data analysis, see Applied Statistics for Science and Industry, by A. Romano, 1977, Allyn and Bacon, publisher.

The data is preferably stored and manipulated using one or more computer programs or computer systems. These systems will typically have data storage capability (e.g., disk drives, tape storage, optical disks, etc.). Further, the computer systems can be networked or can be stand-alone systems. If networked, the computer system would be able to transfer data to any device connected to the networked computer system for example a medical doctor or medical care facility using standard e-mail software, a central database using database query and update software (e.g., a data warehouse of data points, derived data, and data attributes obtained from a large number of subjects). Alternatively, a user could access from a doctor's office or medical facility, using any computer system with Internet access, to review historical data that can be useful for determining treatment.

If the networked computer system includes a World Wide Web application, the application includes the executable code required to generate database language statements, for example, SQL statements. Such executables typically include embedded SQL statements. The application further includes a configuration file that contains pointers and addresses to the various software entities that are located on the database server in addition to the different external and internal databases that are accessed in response to a user request. The configuration file also directs requests for database server resources to the appropriate hardware, as can be necessary if the database server is distributed over two or more different computers.

As a person of skill in the art will appreciate, one or more of the parameters specified in Table 1, Table and Table 3 can be used at an initial time point $T_1$ to assess the severity of a bone disease such as osteoporosis or arthritis. The patient can then serve as their own control at a later time point $T_2$, when a subsequent measurement using one or more of the same parameters used at $T_1$ is repeated.

A variety of data comparisons can be made that will facilitate drug discovery, efficacy, dosing, and comparisons. For example, one or more of the parameters specified in Table 1, Table 2 and Table 3 may be used to identify lead compounds during drug discovery. For example, different compounds can be tested in animal studies and the lead compounds with regard to highest therapeutic efficacy and lowest toxicity, e.g. to the bone or the cartilage, can be identified. Similar studies can be performed in human subjects, e.g. FDA phase I, II or III trials. Alternatively, or in addition, one or more of the parameters specified in Table 1, Table 2 and Table 3 can be used to establish optimal dosing of a new compound. It will be appreciated also that one or more of the parameters specified in Table 1, Table 2 and Table 3 can be used to compare a new drug against one or more established drugs or a placebo. The patient can then serve as their own control at a later time point $T_2$,

EXAMPLES

Example 1

Correlation of Macro-Anatomical and Structural Parameters to Fracture Load

Using 15 fresh cadaveric femurs, the following analyses were performed to determine the correlation of macro-anatomical and structural parameters to fracture load.

Standardization of Hip radiographs: Density and magnification calibration on the x-ray radiographs was achieved using a calibration phantom. The reference orientation of the hip x-rays was the average orientation of the femoral shaft.

Automatic Placement of Regions of Interest. An algorithm was developed and used to consistently and accurately place 7 regions of interest based on the geometric and position of proximal femur. FIG. 10. In brief, the algorithm involved the detection of femoral boundaries, estimation of shaft and neck axes, and construction of ROI based on axes and boundary intercept points. This approach ensured that the size and shape of ROIs placed conformed to the scale and shape of the femur, and thus were consistent relative to anatomic features on the femur.

Automatic Seqmentation of the proximal femur: A global gray level thresholding using bi-modal histogram segmentation algorithm(s) was performed on the hip images and a binary image of the proximal femur was generated. Edge-detection analysis was also performed on the hip x-rays, including edge detection of the outline of the proximal femur that involved breaking edges detected into segments and characterizing the orientation of each segment. Each edge segment was then referenced to a map of expected proximal femur edge orientation and to a map of the probability of edge location. Edge segments that did not conform to the expected orientation or which were in low probability regions were removed. Morphology operations were applied to the edge image(s) to connect any discontinuities. The edge image formed an enclosed boundary of the proximal femur. The region within the boundary was then combined with the binary image from global thresholding to form the final mask of the proximal femur.

Automatic Segmentation and Measurement of the Femoral Cortex: Within a region of interest (ROI), edge detection was applied. Morphology operations were applied to connect edge discontinuities. Segments were formed within enclosed edges. The area and the major axis length of each segment were then measured. The regions were also superimposed on the original gray level image and average gray level within each region was measured. The cortex was identified as those segments connected to the boundary of the proximal femur mask with the greatest area, longest major axis length and a mean gray level about the average gray level of all enclosed segments within the proximal femur mask.

The segment identified as cortex was then skeletonized. The orientation of the cortex skeleton was verified to conform to the orientation map of the proximal femur edge. Euclidean distance transform was applied to the binary image of the segment. The values of distance transform value along the skeleton were sampled and their average, standard deviation, minimum, maximum and mod determined.

Watershed Seqmentation for Characterizing Trabecular Structure: Marrow spacing was characterized by determining watershed segmentation of gray level trabecular structures on the hip images; essentially as described in Russ "The Image Processing Handbook," $3^{rd}$. ed. pp.494-501. This analysis take the gray level contrast between the marrow spacing and adjacent trabecular structures into account. The segments of marrow spacing generated using watershed segmentation were measured for the area, eccentricity, orientation, and the average gray level on the x-ray image within the segment. Mean, standard deviation, minimum, maximum and mod. were determined for each segment. In addition, various structural and/or macro-anatomical parameters were assessed for several ROIs (FIG. 10).

Measurement of Femoral Neck BMD: DXA analysis of bone mineral density was performed in the femoral neck region of the femurs.

Biomechanical Testing of Intact Femur Each cadaveric femur sample (n=15) was tested for fracture load as follows. First, the femur was placed at a 15° angle of tilt and an 8° external rotation in an Instron 1331 Instrument (Instron, Inc.) and a load vector at the femoral head simulating single-leg stance was generated, essentially as described in Cheal et al. (1992) J. Orthop. Res. 10(3):405-422. Second, varus/valgus and torsional resistive movements simulating passive knee ligaments restraints were applied. Next, forces and movement at failure were measured using a six-degree of freedom load cell. Subsequently, a single ramp, axial compressive load was applied to the femoral head of each sample at 100 mm/s until fracture. (FIG. 12). Fracture load and resultant equilibrium forces and moments at the distal end of the femur were measured continuously. FIG. 11 shows various results of biomechanical testing.

The correlation between (1) DXA femoral next BMD and facture load; (2) bone structure and fracture load; and (3) macro-anatomical analyses and fracture load was determined and shown in FIG. 13-15, respectively.

Multivariate linear regression analysis was also performed, combining several structural and macro-anatomical parameters, including local maximum marrow spacing (r=0.6 linearized); standard deviation of cortical thickness of ROI3 (r=0.57); maximum cortical thickness of ROI5 (r=0.56); and mean node-free end length for ROI3 (r=0.50). Results are shown in FIG. 16 and demonstrate that, using analyses, described herein there is a good correlation between predicted fracture load and actual fracture load (r=0.81, p<0.001). The mean fracture load was 5.4 kiloNewton with a standard deviation of 2.3 kiloNewton. These statistics and the coefficients of multivariate linear regression were stored as data of the fracture load reference database.

Example 2

Correlation of 2D and 3D Measurements

To demonstrate that methods using 2D x-ray technology to quantitatively assess trabecular architecture is as effective as 3D $\mu$CT, which serves as a gold standard for such measurements, the following experiments were performed. Bone cores (n=48) were harvested from cadaveric proximal femora. Specimen radiographs were obtained and 2D structural parameters were measured on the radiographs. Cores were then subjected to 3D $\mu$CT and biomechanical testing. The $\mu$CT images were analyzed to obtained 3D micro-structural measurements. Digitized 2D x-ray images of these cores were also analyzed as described herein to obtain comparative micro-structural measurements.

Results showed very good correlation among the numerous 2D parameters and 3D $\mu$CT measurements, including for example correlation between 2D Trabecular Perimeter/Trabecular Area (Tb.P/Tb.A) with 3D Bone Surface/Bone Volume (r=0.92, p<0.001), and 2D Trabecular Separation (Tb.Sp) with 3D Trabecular Separation (r=0.88, p<0.001). The 2D Tb.P/Tb.A and 2D Tb.Sp also function correlate very well as predictive parameters for the mechanical loads required to fracture the cores, with r=−0.84 (p<0.001) and r=−0.83 (p<0.001), respectively, when logarithmic and exponential transformations were used in the regression.

These results demonstrate that 2D micro-structural measurements of trabecular bone from digitized radiographs are highly correlated with 3D measurements obtained from $\mu$-CT images. Therefore, the mechanical characteristics of trabecular bone microstructure from digitized radiographic images can be accurately determined from 2D images.

Example 3

Prediction of Fracture Risk using Fracture Load Reference Database

A hip x-ray of cadaver pelvis was exposed using standard clinical procedure and equipment. The radiograph film was developed and digitized. The image was then analyzed to obtain micro-structure, and macro-anatomical parameters. The local maximum spacing, standard deviation of cortical thickness of ROI3, maximum cortical thickness of ROI5, and mean node-free end length for ROI3 were used to predict load required to fracture the cadaver hip using the coefficients of multivariate linear regression stored in the fracture load reference database. The predicted fracture load was 7.5 kiloNewton. This fracture load is 0.98 standard deviation above the average of the fracture load reference database (or z-score=0.98). This result may suggest that the subject had a relatively low risk of sustaining a hip fracture as compared to the population of the reference database.

The foregoing description of embodiments of the present invention has been provided for the purposes of illustration and description. It is not intended to be exhaustive or to limit the invention to the precise forms disclosed. Many modifications and variations will be apparent to the practitioner skilled in the art. The embodiments were chosen and described in order to best explain the principles of the invention and its practical application, thereby enabling others skilled in the art to understand the invention and the various embodiments and with various modifications that are suited to the particular use contemplated. It is intended that the scope of the invention be defined by the following claims and its equivalence.

What is claimed is:

1. A method of predicting bone or articular disease in a subject, the method comprising the steps of:
   determining one or more micro-structural parameters of at least a portion of a bone in said subject, wherein determining includes using a computer to extract trabecular micro-structure from electronic image data of at least a portion of said bone;
   determining electronically from the electronic image data a cortical bone thickness of the bone; and
   combining at least said determined cortical bone thickness with the one or more micro-structural parameters into an index and comparing said index to a reference database to predict the risk of bone or articular disease.

2. The method of claim 1, wherein said bone or articular disease is fracture risk.

3. The method of claim 1, wherein the parameters are obtained from one or more regions of interest in an image obtained from said subject.

4. The method of claim 3, wherein the electronic image is selected from the group consisting of an x-ray image, a CT image, an ultrasound image and an MRI.

5. The method of claim 1, further comprising determining one or more biomechanical parameters of at least a portion of said bone;
   wherein the step of combining further includes combining said one or more biomechanical parameters with said determined cortical bone thickness and said one or more micro-structural parameters into said index.

6. The method of claim 1, wherein said micro-structural parameters are selected from the group consisting of: stainless steel equivalent thickness wherein the stainless steel equivalent thickness is determined as the average gray value of the region of interest expressed as thickness of stainless steel with equivalent intensity; trabecular contrast wherein the trabecular contrast is determined as one of the trabecular equivalent thickness and marrow equivalent thickness; fractal dimension; Fourier spectral analysis wherein the Fourier spectral analysis is determined as one of a mean transform coefficient absolute value and a mean spatial first moment; predominant orientation of spatial energy spectrum; at least one of trabecular area and total area; trabecular perimeter; trabecular distance transform; marrow distance transform; trabecular distance transform regional maxima values; marrow distance transform regional maxima values; star volume; trabecular bone pattern factor; connected skeleton count or trees (T); node count (N); segment count (S); node-to-node segment count (NN); node-to-free-end segment count (NF); node-to-node segment length (NNL) node-to-free-end segment length (NFL); free-end-to-free-end segment length (N'F'L); node-to-node total struts length (NN.TSL); free-end-to-free-ends total struts length (FF.TSL); total struts length (TSL); FF.TSL/TSL; NN.TSL/TSL; loop count (Lo); loop area; mean distance transform values for each connected skeleton; mean distance transform values for each segment (Tb.Th); mean distance transform values for each node-to-node segment (Tb.Th.NN); mean distance transform values for each node-to-free-end segment (Tb.Th.NF); orientation of each segment; angle of each segment; angle between segments; length-thickness ratios (NNL/Tb.Th.NN) and (NFL/Tb.Th.NF); and interconnectivity index (ICI) ICI=(N*NN)/(T*(NF+1)).

7. The method of claim 1, wherein said combining comprises univariate, bivariate or multivariate statistical analysis.

8. The method of claim 1, further comprising comparing said parameters to data derived from a reference database of known disease parameters.

9. The method of claim 1, wherein the bone is in a region selected from the group consisting of leg, knee, hip, spine and arm.

10. The method of claim 1, further comprising administering a compound to the subject.

11. The method of claim 10, wherein determining and combining are repeated at two or more time points and further wherein one time point is prior to administration of the compound.

12. A method of determining the effect of a candidate agent on a subject's prognosis for musculoskeletal disease comprising: predicting a first risk of musculoskeletal disease in subject according to the method of claim 1; administering a candidate agent to said subject; predicting a second risk of said musculoskeletal disease in said subject according to the method of claim 1; and comparing said first and second risks, thereby determining the effect of the candidate on the subject's prognosis for said disease.

13. The method of claim 12, wherein said candidate agent is administered to the subject.

14. The method of claim 12, wherein said administration comprises ingestion or injection.

15. The method of claim 12, wherein said candidate agent is selected from the group consisting of molecules, pharmaceuticals, biopharmaceuticals, agropharmaceuticals and combinations thereof.

16. The method of claim 1 wherein said parameters are selected from the group consisting of: all microarchitecture parameters on structures parallel to stress lines; all microarchitecture parameters on structures perpendicular to stress lines; geometry; shaft angle; neck angle; average and minimum diameter of femur neck; hip axis length; CCD (caput-collum-diaphysis) angle; width of trochanteric region; largest cross-section of femur head; standard deviation of cortical bone thickness within ROI; minimum, maximum, mean and median thickness of cortical bone within ROI; hip joint space width; all microarchitecture parameters on vertical structures; all microarchitecture parameters on horizontal structures; superior endplate cortical thickness (anterior, center, posterior); inferior endplate cortical thickness (anterior, center, posterior); anterior vertebral wall cortical thickness (superior, center, inferior); posterior vertebral wall cortical thickness (superior, center, inferior); superior aspect of pedicle cortical thickness; inferior aspect of pedicle cortical thickness; vertebral height (anterior, center, posterior); vertebral diameter (superior, center, inferior); pedicle thickness (supero-inferior direction); maximum vertebral height; minimum vertebral height; average vertebral height; anterior vertebral height; medial vertebral height; posterior vertebral height; maximum inter-vertebral height; minimum inter-vertebral height; average inter-vertebral height; average medial joint space width; minimum medial joint space width; maximum medial joint space width; average lateral joint space width; minimum lateral joint space width; and maximum lateral joint space width.

* * * * *

UNITED STATES PATENT AND TRADEMARK OFFICE
Certificate

Patent No. 7,840,247 B2                                                  Patented: November 23, 2010

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Siau-Way Liew, Pinole, CA (US); Philipp Lang, Lexington, MA (US); Daniel Steines, Palo Alto, CA (US); Claude D. Arnaud, Mill Valley, CA (US); and Rene Vargas-Voracek, Sunnyvale, CA (US).

Signed and Sealed this Sixth Day of November 2012.

Tse Chen
*Supervisory Patent Examiner*
Art Unit 3777
Technology Center 3700